United States Patent
Abate et al.

(10) Patent No.: US 11,142,791 B2
(45) Date of Patent: Oct. 12, 2021

(54) COMBINED MULTIPLE-DISPLACEMENT AMPLIFICATION AND PCR IN AN EMULSION MICRODROPLET

(71) Applicant: The Regents of the University of California, Oakland, CA (US)

(72) Inventors: Adam R. Abate, Daly City, CA (US); David Sukovich, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 284 days.

(21) Appl. No.: 16/324,532

(22) PCT Filed: Aug. 9, 2017

(86) PCT No.: PCT/US2017/046159
§ 371 (c)(1),
(2) Date: Feb. 8, 2019

(87) PCT Pub. No.: WO2018/031691
PCT Pub. Date: Feb. 15, 2018

(65) Prior Publication Data
US 2019/0218594 A1    Jul. 18, 2019

Related U.S. Application Data

(60) Provisional application No. 62/373,317, filed on Aug. 10, 2016.

(51) Int. Cl.
| | |
|---|---|
| *C12Q 1/686* | (2018.01) |
| *C12P 19/34* | (2006.01) |
| *C12Q 1/6844* | (2018.01) |
| *C12Q 1/6806* | (2018.01) |
| *C12Q 1/6818* | (2018.01) |
| *C12Q 1/6886* | (2018.01) |
| *C12M 3/00* | (2006.01) |
| *C12Q 1/68* | (2018.01) |
| *B01L 7/00* | (2006.01) |
| *B01L 3/00* | (2006.01) |

(52) U.S. Cl.
CPC .............. *C12Q 1/686* (2013.01); *C12M 3/00* (2013.01); *C12P 19/34* (2013.01); *C12Q 1/68* (2013.01); *C12Q 1/6806* (2013.01); *C12Q 1/6818* (2013.01); *C12Q 1/6844* (2013.01); *C12Q 1/6886* (2013.01); *B01L 3/502784* (2013.01); *B01L 7/52* (2013.01); *C12Q 2600/112* (2013.01); *C12Q 2600/118* (2013.01); *C12Q 2600/156* (2013.01); *C12Q 2600/16* (2013.01)

(58) Field of Classification Search
CPC ................. C12Q 1/6844; C12Q 1/686; C12Q 2531/119; C12Q 2563/159
See application file for complete search history.

(56) References Cited

U.S. PATENT DOCUMENTS

| | | | |
|---|---|---|---|
| 7,638,276 B2 | 12/2009 | Griffiths et al. | |
| RE41,780 E | 9/2010 | Anderson et al. | |
| 8,067,159 B2 | 11/2011 | Brown et al. | |
| 8,257,925 B2 | 9/2012 | Brown et al. | |
| 8,765,485 B2 | 7/2014 | Link et al. | |
| 9,150,852 B2 | 10/2015 | Samuels et al. | |
| 10,161,007 B2 | 12/2018 | Abate et al. | |
| 10,745,762 B2 | 8/2020 | Abate et al. | |
| 2002/0086042 A1 | 7/2002 | Delrieu et al. | |
| 2003/0156993 A1 | 8/2003 | Staats | |
| 2003/0180737 A1* | 9/2003 | Gu .......................... | C12P 19/34 |
| | | | 435/6.1 |
| 2005/0019902 A1 | 1/2005 | Mathies et al. | |
| 2005/0112639 A1 | 5/2005 | Wang et al. | |
| 2005/0172476 A1 | 8/2005 | Stone et al. | |
| 2007/0039866 A1 | 2/2007 | Schroeder et al. | |
| 2007/0077572 A1 | 4/2007 | Tawfik et al. | |
| 2007/0141593 A1 | 6/2007 | Lee et al. | |
| 2007/0231880 A1 | 10/2007 | Chang-yen et al. | |
| 2008/0014589 A1 | 1/2008 | Link et al. | |
| 2009/0045064 A1 | 2/2009 | Simmons et al. | |
| 2009/0098555 A1 | 4/2009 | Roth et al. | |
| 2010/0015614 A1 | 1/2010 | Beer et al. | |
| 2010/0028915 A1 | 2/2010 | Gualberto et al. | |
| 2010/0055677 A1 | 3/2010 | Colston, Jr. et al. | |
| 2010/0137163 A1 | 6/2010 | Link et al. | |
| 2010/0173394 A1 | 7/2010 | Colston, Jr. et al. | |
| 2010/0285975 A1 | 11/2010 | Mathies et al. | |

(Continued)

FOREIGN PATENT DOCUMENTS

| | | |
|---|---|---|
| AU | 2013203624 A1 | 5/2013 |
| AU | 2013302867 A1 | 2/2015 |

(Continued)

OTHER PUBLICATIONS

Tamminen, M.. et al., Single gene-based distinction of individual microbial genomes from a mixed population of microbial cells, Front. Microbiol., vol. 6, 195, pp. 1-10 (Year: 2015).*

(Continued)

*Primary Examiner* — Teresa E Strzelecka
(74) *Attorney, Agent, or Firm* — Edward J. Baba; Michael J. Blessent; Bozicevic, Field & Francis LLP

(57) ABSTRACT

The methods and systems described herein provide an improved emulsion droplet based nucleic acid amplification method, which allows nucleic acids contained in biological systems to be detected, quantitated and/or sorted based on their sequence as detected with nucleic acid amplification techniques, e.g., polymerase chain reaction (PCR). The nucleic acids can be free floating or contained within living or nonliving structures, including particles, viruses, and cells. The nucleic acids can include, e.g., DNA or RNA.

20 Claims, 22 Drawing Sheets

Specification includes a Sequence Listing.

(56) References Cited

U.S. PATENT DOCUMENTS

| | | |
|---|---|---|
| 2011/0053798 A1 | 3/2011 | Hindson et al. |
| 2011/0056575 A1 | 3/2011 | Hong et al. |
| 2011/0059556 A1 | 3/2011 | Strey et al. |
| 2011/0086352 A1 | 4/2011 | Bashir et al. |
| 2011/0103176 A1 | 5/2011 | Van Dam et al. |
| 2011/0104816 A1 | 5/2011 | Pollack et al. |
| 2011/0118151 A1 | 5/2011 | Eshoo et al. |
| 2011/0160078 A1 | 6/2011 | Fodor et al. |
| 2011/0217736 A1 | 9/2011 | Hindson |
| 2011/0311978 A1 | 12/2011 | Makarewicz, Jr. et al. |
| 2012/0010086 A1 | 1/2012 | Froehlich et al. |
| 2012/0045765 A1 | 2/2012 | Curran et al. |
| 2012/0122714 A1 | 5/2012 | Samuels et al. |
| 2012/0190032 A1 | 7/2012 | Ness et al. |
| 2012/0190033 A1 | 7/2012 | Ness et al. |
| 2012/0196288 A1 | 8/2012 | Beer |
| 2012/0219947 A1 | 8/2012 | Yurkovetsky et al. |
| 2012/0220494 A1 | 8/2012 | Samuels et al. |
| 2012/0222748 A1 | 9/2012 | Weitz et al. |
| 2012/0258870 A1 | 10/2012 | Schwartz et al. |
| 2012/0264646 A1 | 10/2012 | Link et al. |
| 2012/0270739 A1 | 10/2012 | Rava et al. |
| 2012/0309002 A1 | 12/2012 | Link |
| 2012/0316074 A1 | 12/2012 | Saxonov |
| 2013/0032235 A1 | 2/2013 | Johnstone et al. |
| 2013/0046030 A1 | 2/2013 | Rotem et al. |
| 2013/0084572 A1 | 4/2013 | Hindson et al. |
| 2013/0095469 A1 | 4/2013 | Koltay et al. |
| 2013/0116130 A1 | 5/2013 | Fu et al. |
| 2013/0130919 A1 | 5/2013 | Chen et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0236901 A1 | 9/2013 | Potier et al. |
| 2013/0295567 A1 | 11/2013 | Link et al. |
| 2013/0295587 A1 | 11/2013 | Sjobom |
| 2014/0057799 A1 | 2/2014 | Johnson et al. |
| 2014/0154695 A1 | 6/2014 | Miller et al. |
| 2014/0155295 A1 | 6/2014 | Hindson et al. |
| 2014/0179544 A1 | 6/2014 | Steenblock et al. |
| 2014/0199730 A1 | 7/2014 | Agresti et al. |
| 2014/0199731 A1 | 7/2014 | Agresti et al. |
| 2014/0272988 A1 | 9/2014 | Zador et al. |
| 2014/0323316 A1 | 10/2014 | Drmanac et al. |
| 2014/0378349 A1 | 12/2014 | Hindson et al. |
| 2015/0232942 A1 | 8/2015 | Abate et al. |
| 2015/0298091 A1 | 10/2015 | Weitz et al. |
| 2016/0177375 A1 | 6/2016 | Abate et al. |
| 2016/0265043 A1 | 9/2016 | Geng et al. |
| 2017/0009274 A1 | 1/2017 | Abate et al. |
| 2017/0022538 A1 | 1/2017 | Abate et al. |
| 2017/0121756 A1 | 5/2017 | Abate et al. |
| 2018/0056288 A1 | 3/2018 | Abate et al. |
| 2018/0216160 A1 | 8/2018 | Abate et al. |
| 2018/0237836 A1 | 8/2018 | Abate et al. |
| 2019/0127789 A1 | 5/2019 | Weitz et al. |
| 2019/0169700 A1 | 6/2019 | Abate et al. |
| 2019/0218594 A1 | 7/2019 | Abate et al. |
| 2019/0241965 A1 | 8/2019 | Abate et al. |
| 2019/0330701 A1 | 10/2019 | Abate et al. |

FOREIGN PATENT DOCUMENTS

| | | |
|---|---|---|
| AU | 2016215298 A1 | 8/2017 |
| AU | 2016215304 A1 | 8/2017 |
| AU | 2017382905 A1 | 7/2019 |
| AU | 2019226236 A1 | 9/2019 |
| CA | 2881783 A1 | 2/2014 |
| CA | 3001986 A1 | 4/2016 |
| CA | 2974299 A1 | 8/2016 |
| CA | 2974306 A1 | 8/2016 |
| CA | 3047328 A1 | 6/2018 |
| CN | 1693478 A | 11/2005 |
| CN | 104736725 A | 6/2015 |
| CN | 107107058 A | 8/2017 |
| CN | 107429426 A | 12/2017 |
| CN | 107530654 A | 1/2018 |
| CN | 108350488 A | 7/2018 |
| CN | 110088290 A | 8/2019 |
| CN | 110462053 A | 11/2019 |
| DE | 10339452 A1 | 3/2005 |
| EP | 1547677 A1 | 6/2005 |
| EP | 2145955 B1 | 2/2012 |
| EP | 2565650 A1 | 3/2013 |
| EP | 2882872 A2 | 6/2015 |
| EP | 3160654 A2 | 5/2017 |
| EP | 3209419 A1 | 8/2017 |
| EP | 3253479 A2 | 12/2017 |
| EP | 3253910 A1 | 12/2017 |
| EP | 3337907 A1 | 6/2018 |
| EP | 3497228 A1 | 6/2019 |
| EP | 3571308 A1 | 11/2019 |
| GB | 2519906 A | 5/2015 |
| GB | 2539836 A | 12/2016 |
| JP | 2013503630 A | 2/2013 |
| JP | 2014521334 A | 8/2014 |
| JP | 2015533079 A | 11/2015 |
| JP | 2018505671 A | 3/2018 |
| JP | 2018508198 A | 3/2018 |
| JP | 2018525004 A | 9/2018 |
| WO | 9412216 A1 | 6/1994 |
| WO | 2007140015 A2 | 12/2007 |
| WO | 2009050512 A2 | 4/2009 |
| WO | 2009054870 A2 | 4/2009 |
| WO | 2009111014 A2 | 9/2009 |
| WO | 2010148039 A2 | 12/2010 |
| WO | 2011047307 A1 | 4/2011 |
| WO | 2012011091 A2 | 1/2012 |
| WO | 2012048341 A1 | 4/2012 |
| WO | 2012083225 A2 | 6/2012 |
| WO | 2012109600 A2 | 8/2012 |
| WO | 2012142213 A2 | 10/2012 |
| WO | 2012162267 A2 | 11/2012 |
| WO | 2013095469 A1 | 6/2013 |
| WO | 2013119753 A1 | 8/2013 |
| WO | 2013126741 A1 | 8/2013 |
| WO | 2013130512 A2 | 9/2013 |
| WO | 2013134261 A1 | 9/2013 |
| WO | 2013173394 A2 | 11/2013 |
| WO | 2014028378 A2 | 2/2014 |
| WO | 2014028537 A1 | 2/2014 |
| WO | 2014047556 A1 | 3/2014 |
| WO | 2014083435 A2 | 6/2014 |
| WO | 2014093676 A1 | 6/2014 |
| WO | 2014108323 A1 | 7/2014 |
| WO | 2014138132 A2 | 9/2014 |
| WO | 2014151658 A1 | 9/2014 |
| WO | 2014153071 A1 | 9/2014 |
| WO | 2015031691 A1 | 3/2015 |
| WO | 2015069798 A1 | 5/2015 |
| WO | 2015120398 A1 | 8/2015 |
| WO | 2015157369 A1 | 10/2015 |
| WO | WO2015179848 A1 | 11/2015 |
| WO | 2015189336 A1 | 12/2015 |
| WO | 2015200717 A2 | 12/2015 |
| WO | 2016064755 A2 | 4/2016 |
| WO | 2016065056 A1 | 4/2016 |
| WO | 2016126865 A1 | 8/2016 |
| WO | 2016126871 A2 | 8/2016 |
| WO | 2017031125 A1 | 2/2017 |
| WO | 2018031691 A1 | 2/2018 |
| WO | 2018119301 A1 | 6/2018 |
| WO | WO2019099908 A1 | 5/2019 |

OTHER PUBLICATIONS

Integrated DNA Technologies "Molecular Facts and Figures", pp. 1-9 (Year: 2011).*

Lage, J.M. et al., Whole Genome Analysis of Genetic Alterations in Small DNA Samples Using Hyperbranched Strand Displacement Amplification and Array-CGH, Genome Res., vol. 13, pp. 294-307 (Year: 2003).*

(56) References Cited

OTHER PUBLICATIONS

Teh, Shia-Yen, et al., "Droplet microfluidics", Lab on a chip, vol. 8, Issue 2, Jan. 11, 2008, 198-220.
Caruccio, et al., "Preparation of next-generation sequencing libraries using Nextera™ technology: simultaneous DNA fragmentation and adaptor tagging by in vitro transposition", Methods in Molecular Biology, 2011, vol. 733, pp. 241-255.
Demaree, Benjamin, et al., "An Ultrahigh-throughput Microfluidic Platform for Single-cell Genome Sequencing", Journal of Visualized Experiments 135 (e57598), 2018, 1-13.
Le Geoff, et al., "Hydrogel microparticles for biosensing", Eur Polym J., 2015, vol. 72,, 49 pages.
Gong, Jian, et al., "Characterization and Design of Digitizing Processes for Uniform and Controllable Droplet Volume in EWOD Digital Microfluidics", Solid-State Sensors, Actuators, and Microsystems Workshop, 2006, 159-162.
Ichii, Tetsuo, et al., "Amplification of RNA in Growing and Dividing Micro-Droplets", 14th International Conf on Miniaturized Systems for Chemistry and Life Sciences, 2010, 2089-2091.
Kumaresan, Palani, et al., "High-Throughput Single Copy DNA Amplification and Cell Analysis in Engineered Nanoliter Droplets", Anal. Chem. 80, 2008, 3522-3529.
Lan, Freeman, et al., "Single-cell genome sequencing at ultra-high-throughput with microfluidic droplet barcoding", Nature Biotechnology 35(7), 2017, 640-646.
Lim, Shaun W., et al., "Ultrahigh-throughput sorting of microfluidic drops with flow cytometry", Lab Chip, 2013, vol. 13, pp. 4563-4572.
Pekin, Deniz, et al., "Quantitative and sensitive detection of rare mutations using droplet-based microfluidics", Lab Chip 11, 2011, 2156-2166.
Rakszewska, Agata, et al., "One drop at a time: toward droplet microfluidics as a versatile tool for single-cell analysis", NPG Asia Materials 6(10), 2014, 1-11.
Shembekar, Nachiket, et al., "Droplet-based microfluidics in drug discovery, transcriptomics and high-throughput molecular genetics", Lab on a Chip 16(8), 2016, 1314-1331.
Hindson, et al., (2011) High-throughput droplet digital PCR system for Absolute Quatitation of DN a copy number. Analytical chemistry, 83(22), pp. 8604-8610.
Nakano, Michihiko, et al., "Single-molecule reverse transcription polymerase chain reaction using water-in-oil emulsion", vol. 99(3), Mar. 2005, pp. 293-295.
Nikolova, Albena N, et al., "Effect of grafted PEG-2000 on the size and permeability of vesicles", vol. 1304(2), Nov. 22, 1996, pp. 120-128.
Nishikawa, Yohei, et al., "Monodisperse Picoliter Droplets for Low-Bias and Contamination-Free Reactions in Single-Cell Whole Genome Amplification", PLoS One vol. 10(9), Sep. 2015, e0138733.
Novak, Richard, et al., "Single-cell multiplex gene detection and sequencing with microfluidically generated agarose emulsions", Angew Chem Int Ed Engl., vol. 50(2), Jan. 10, 2011, 390-395.
Nunes, J K, et al., "Dripping and jelling in microfluidic multiphase flows applied to particle and fibre synthesis", Journal of Physics D: Applied Physics, vol. 46(11), Feb. 22, 2013.
Oberholzer, Thomas, et al., "Polymerase chain reaction in liposomes", vol. 2(10), Oct. 1995, 677-682.
O'Donovan, Brian, et al., "Electrode-free picoinjection of microfluidic drops", Lab on a chip, vol. 12, Aug. 17, 2012, 4029-4032.
Okochi, Mina, et al., "Droplet-based gene expression analysis using a device with magnetic force-based-droplet-handling system", Journal of Bioscience and Bioengineering, vol. 109(2), Feb. 2010, 193-197.
Perry, David J, "Solid-Phase Sequencing of Biotinylated PCR Products with Streptavidin-Coated Magnetic Beads", Hemostasis and Thrombosis Protocols, vol. 31, 1999, 49-54.
Piatek, Amy S, et al., "Molecular beacon sequence analysis for detecting drug resistance in *Mycobacterium tuberculosis*", Nature Biotechnology, vol. 16(4), Apr. 1998, 359-363.

Priest, Craig, et al., "Controlled electrocoalescence in microfluidics: Targeting a single lamella", Appl Phys Lett, vol. 89, Sep. 25, 2006, 134101.
Roche, "emPCR Amplification Method Manual—Lib L LV for GS FLX+ Series—XL+", 454 Sequencing, Life Science Corp., May 2011, 1-12.
Rolando, Monica, et al., "Legionella pneumophila Effector RomA Uniquely Modifies Host Chromatin to Repress Gene Expression and Promote Intracellular Bacterial Replication", Cell Host & Microbe, vol. 13(4), Apr. 17, 2013, 395-405.
Sciambi, Adam, et al., "Adding reagent to droplets with controlled rupture of encapsulated double emulsions", Biomicrofluidics, vol. 7(4), Aug. 5, 2013, 044112-1-044112-6.
Sciambia, Adam, et al., "Accurate microfluidic sorting of droplets at 30 kHz", Lab Chip vol. 15(1), 2015, 47-51.
Seemann, Ralf, et al., "Droplet based microfluidics", IOP Science, vol. 75, Dec. 22, 2011, 016601.
Shui, Lingling, et al., "Microfluidic DNA fragmentation for on-chip genomic analysis", Nanotechnology, vol. 22(49), Dec. 9, 2011, 494013.
Sidore, Angus M, et al., "Enhanced sequencing coverage with digital droplet multiple displacement amplification", Nucleic Acids Res., vol. 44(7), Apr. 20, 2016, e66.
Siegel, Adam, et al., "Microsolidics: Fabrication of Three-Dimensional Metallic Microstructures in Poly (dimethylsiloxane)", Advanced Materials, vol. 19(5), Feb. 2007, 727-733.
Song, Helen, et al., "Reactions in droplets in microfluidic channels", Angew Chem Int Ed Engl, vol. 45(44), Nov. 6, 2006, 7336-7356.
Squires, Tom M, et al., "Microfluidics: Fluid physics at the nanoliter scale", Reviews of modern physics, vol. 77(3), Oct. 6, 2005, 977-1026.
Stone, H. A, et al., "Engineering flows in small devices: microfluidics toward a lab-on-achip", vol. 36, Jan. 21, 2004, pp. 381-411.
Stott, Shannon L, et al., "Isolation of circulating tumor cells using a microvortex-generating herringbone-chip", Proc Natl Acad Sci USA, vol. 107(43), Oct. 26, 2010, pp. 18392-18397.
Syed, F, et al., "Next-generation sequencing library preparation: simultaneous fragmentation and tagging using in vitro transposition", vol. 6, Nov. 2009, pp. 1-2.
Tadmorad, Arbel D, et al., "Probing individual environmental bacteria for viruses by using microfluidic digital PCR", vol. 333(6038), 2011, pp. 58-62.
Takagi, Junya, et al., "Continuous particle separation in a microchannel having asyuuuetrically arranged multiple branches", Lab on a Chip, vol. 5(7), May 19, 2005, pp. 778-784.
Tamminen, Manu V, et al., "Single gene-based distinction of individual microbial genomes from a mixed population of microbial cells", Front Microbiol., vol. 6(195), Mar. 11, 2015, 1-10.
Tewhey, Ryan, et al., "Microdroplet-based PCR enrichment for large-scale targeted sequencing", Nature Biotechnology, vol. 27, Nov. 1, 2009, 1025-1031.
Thomann, Yi, et al., "PMMA Gradient Materials and in situ Nanocoating via Self-Assembly of Semifluorinated Hyperbranched Amphiphiles", Macromolecular Chemistry and Physics, vol. 206(1), 2005, 135-141.
Thorsen, Todd, et al., "Dynamic pattern formation in a vesicle-generating microfluidic device", Physical Review Letter, vol. 86(18), Apr. 30, 2001, 4163-4166.
Tsai, Scott S H, et al., "Microfluidic immunomagnetic multi-target sorting—a model for controlling deflection of paramagnetic beads", Lab on a Chip, vol. 11(15), Aug. 7, 2011, 2577-2582.
Ullal, Adeeti V, et al., "Cancer cell profiling by barcoding allows multiplexed protein analysis in fine needle aspirates", Science Translation Medicine, vol. 6, Issue 219, Jan. 15, 2014, pp. 1-22.
Utada, Andrew S, et al., "Dripping to jetting transitions in co flowing liquid streams", Physical Review Letters, vol. 99(9), Aug. 31, 2007, pp. 094502-1-094502-4.
Vanapalli, Siva A, et al., "Hydrodynamic resistance of single confined moving drops in rectangnlar microchannels", Lab on a Chip, vol. 9, 2009, 982-990.

(56) References Cited

OTHER PUBLICATIONS

Vickers, Jonathan A, et al., "Generation of Hydrophilic Poly(dimethylsiloxane) for High-Performance Microchip Electrophoresis", Anal. Chem, vol. 78(21), Oct. 5, 2006, 7446-7452.
Wang, Chao , et al., "Amphiphilic building blocks for self-assembly: from amphiphiles to supra-amphiphiles", Accounts of Chemical Research, vol. 45(4), Jan. 13, 2012, 608-618.
Wheeler, Aaron R, et al., "Digital microfluidics with in-line sample purification for proteomics analyses with MALDI-MS", Anal Chem. vol. 77(2), 2005, 534-540.
Whitesides, George M, "The origins and the future of microfluidics", Nature vol. 442, 2006, 368-373.
Whitcombe, David , et al., "Detection of PCR products using self-probing amplicons and fluorescence", Nature biotechnology, vol. 17(8), Aug. 1999, 804-807.
Xia, Younan , et al., "Soft lithography", Annual Review of Materials Science, vol. 37, 1998, 551-575.
Yu, Zhenming , et al., "Mung bean nuclease treatment increases capture specificity of microdroplet-PCR based targeted DNA enrichment", PLoS One vol. 9(7), e103491, Jul. 24, 2014, 1-7.
Zeng, Yong , et al., "High-Performance Single Cell Genetic Analysis Using Microfluidic Emulsion Generator Arrays", Anal Chem, vol. 82(8), Mar. 1, 2010, 3183-3190.
Zheng, Bo , et al., "Formation of droplets of in microfluidic channels alternating composition and applications to indexing of concentrations in droplet-based assays", Anal Chem., vol. 76, Jul. 24, 2004, 4977-4982.
Zhong, Qun , et al., "Multiplex digital PCR: breaking the one target per color barrier of quantitative PCR", Lab on a Chip, vol. 11 (13), Jul. 7, 2011, 2167-2174.
Zhu, Zhi , et al., "Highly sensitive and quantitative detection of rare pathogens through agarose droplet microfluidic emulsion PCR at the single-cell level", Lab on a Chip, vol. 12(20), Jun. 18, 2012, 3907-3913.
Zhu, Y Y, et al., "Reverse transcriptase template switching: a SMART approach for full-length cDNA library Construction", BioTechniques, vol. 30(4), Apr. 2001, 892-897.
Zien, Tse-Fou , "Hydrodynamics of bolus flow—an analytical approach to blood flow in capillaries", Bull Math Biophys, vol. 31(4), Dec. 1969, 681-694.
Extended European Search Report received for European Patent Application Serial No. 13829925.0 dated Feb. 8, 2016, 7 pages.
Extended European Search Report received for European Patent Application Serial No. 15812857.9 dated Oct. 17, 2017, 7 pages.
Extended European Search Report received for European Patent Application Serial No. 15853268.9 dated Sep. 3, 2018, 12 pages.
Extended European Search Report received for European Patent Application Serial No. 16747224.0 dated May 24, 2018, 9 pages.
Extended European Search Report received for European Patent Application Serial No. 16747229.9 dated Sep. 10, 2019, 8 pages.
Extended European Search Report received for European Patent Application Serial No. 16837703.4 dated Nov. 29, 2018, 9 pages.
First search received for Chinese Patent Application Serial No. 2013800532581 dated Feb. 22, 2016, 2 pages.
First search received for Chinese Patent Application Serial No. 2015800704110 dated Dec. 13, 2018, 2 pages.
International Preliminary Report on Patentability received for PCT Application Serial No. PCT/US2013/054517 dated Feb. 26, 2015, 14 pages.
International Preliminary Report on Patentability received for PCT Application Serial No. PCT/US2015/037822 dated Jan. 5, 2017, 7 pages.
International Preliminary Report on Patentability received for PCT Application Serial No. PCT/US2015/056743 dated May 4, 2017, 9 pages.
International Preliminary Report on Patentability received for PCT Application Serial No. PCT/US2016/016438 dated Aug. 17, 2017, 10 pages.
International Preliminary Report on Patentability received for PCT Application Serial No. PCT/US2016/016444 dated Aug. 17, 2017, 40 pages.
International Preliminary Report on Patentability received for PCT Application Serial No. PCT/US2016/047199 dated Mar. 1, 2018, 8 pages.
International Preliminary Report on Patentability received for PCT Application Serial No. PCT/US2017/046159 dated Feb. 21, 2019, 9 pages.
International Preliminary Report on Patentability received for PCT Application Serial No. PCT/US2017/068006 dated Jul. 4, 2019, 7 pages.
International Search Report and Written Opinion received for PCT Application Serial No. PCT/US2013/054517 dated Feb. 21, 2014, 19 pages.
International Search Report and Written Opinion received for PCT Application Serial No. PCT/US2015/037822 dated Feb. 2, 2016, 9 pages.
International Search Report and Written Opinion received for PCT Application Serial No. PCT/US2015/056743 dated Mar. 3, 2016, 12 pages.
International Search Report and Written Opinion received for PCT Application Serial No. PCT/US2016/016438 dated Jun. 10, 2016, 14 pages.
International Search Report and Written Opinion received for PCT Application Serial No. PCT/US2016/016444 dated Jul. 27, 2016, 43 pages.
International Search Report and Written Opinion received for PCT Application Serial No. PCT/US2016/047199 dated Dec. 12, 2016, 10 pages.
International Search Report and Written Opinion received for PCT Application Serial No. PCT/US2017/046159 dated Nov. 21, 2017, 12 pages.
International Search Report and Written Opinion received for PCT Application Serial No. PCT/US2017/068006 dated Mar. 26, 2018, 9 pages.
Abate, Adam R, et al., "Efficient encapsulation with plug-triggered drop formation", vol. 84(3), Phys Rev E Stat Nonlin Soft Matter Phys., Sep. 22, 2011, 031502.
Abate, Adam R, et al., "Faster multiple emulsification with drop splitting", vol. 11(11), Lab Chip, Jun. 7, 2011, 1911-1915.
Abate, Adam R, et al., "High-throughput injection with microfluidics using picoinjectors", PNAS vol. 107(45), Nov. 9, 2010, 19163-19166.
Abate, Adam R, et al., "Microfluidic sorting with high-speed single-layer membrane valves", Applied Physics Letters 96, 2010, 03509-1-203509-3.
Abate, Adam R, et al., "One-step formation of multiple emulsions in microfluidics", vol. 11(2) Lab on a Chip, Oct. 2010, 253-258.
Abate, Adam R, et al., "Photoreactive coating for high-contrast spatial patterning of microfluidic device wettability", vol. 8(12), Lab on a Chip, Oct. 17, 2008, 2157-2160.
Agresti, Jeremy J, et al., "Ultrahigh-throughput screening in drop-based microfluidics for directed evolution", See Corrected Version —Proc Natl Acad Sci USA, 107, 2010, 4004-4009.
Agresti, Jeremy J, et al., "Ultrahigh-throughput screening in drop-based microftuidics for directed evolution", Corrected Version— Proc Natl Acad Sci USA, 107(14), 2010, 6550-6551.
Ahn, Keunho , et al., "Electrocoalescence of drops synchronized by size-dependent flow in microfluidic channels", vol. 88, Applied Physics Letters, Apr. 4, 2006, 264105-1-264105-3.
Ali, M Monsur, et al., "Rolling circle amplification: a versatile tool for chemical biology, materials science and medicine", vol. 43(10), Chem Soc Rev., Mar. 18, 2014, 3324-3341.
Allen, Lisa Z, et al., "Single virus genomics: a new tool for virus discovery", PLoS ONE vol. 6(3), Mar. 23, 2011, e17722.
Arriaga, Laura R, et al., "Ultrathin Shell Double Emulsion Templated Giant Unilamellar Lipid Vesicles with Controlled Microdomain Formation", vol. 10(5), Mar. 12, 2014, 950-956.
Atten, P , "Electrocoalescence of Water Droplets in an Insulating Liquid", vol. 30, May 1993, 259-269.

(56) References Cited

OTHER PUBLICATIONS

Barenholz, Y, et al., "A simple method for the preparation of homogeneous phospholipid vesicles", Biochemistry 16(12), Jun. 14, 1977, 2806-2810.

Baret, Jean C, et al., "Fluorescence-activated droplet sorting (FADS): efficient microfluidic cell sorting based on enzymatic activity", vol. 9(13), Lab on a Chip, Apr. 23, 2009, 1850-1858.

Battaglia, Giuseppe, et al., "Polymeric vesicle permeability: a facile chemical assay", vol. 22(11), Langmuir, Apr. 25, 2006, 4910-4913.

Beer, NR, et al., "On-chip single-copy real-time reverse-transcription PCR in isolated picoliter droplets", Anal Chem., vol. 80(6), Feb. 16, 2008, 1854-1858.

Bernath, K, et al., "In vitro compartmentalization by double emulsions: sorting and gene enrichment by fluorescence activated cell sorting", vol. 325(1), Analytical Biochemistry, Feb. 1, 2004, 151-157.

Bird, R E, et al., "Single-chain antigen-binding proteins", vol. 242 (4877), Science, Oct. 21, 1988, 423-426.

Blainey, Paul C, "The future is now: single-cell genomics of bacteria and archaea", FEMS microbiology reviews 37(3), May 2013, 407-427.

Brouzes, E, et al., "Droplet microfluidic technology for single-cell high-throughput screening", vol. 106(34), Proc Natl Acad Sci U S A., Aug. 25, 2009, 14195-14200.

Brown, Robert B, et al., "Current techniques for single-cell lysis", J R Soc Interface, 5 Suppl 2, Oct. 6, 2008, S131-S138.

Caron, G. Nebe-Von, et al., "Assessment of bacterial viability status by flow cytometry and single cell sorting", vol. 84(6), Journal of Applied Microbiology, Jul. 17, 1997, 988-998.

Chabert, M, et al., "Droplet fusion by alternating current (AC) field electrocoalescence in microchannels", Electrophoresis vol. 26(19), Oct. 19, 2005, 3706-3715.

Chaffer, Christine L, et al., "A Perspective on Cancer Cell Metastasis", Science vol. 331(6024), Mar. 25, 2011, 1559-1564.

Chen, Chin-Ming, et al., "Influence of pH on the stability of oil-in-water emulsions stabilized by a splittable surfactant", Colloids and Surfaces A: Physicochemical and Engineering Aspects, vol. 170 (2-3), Sep. 2000, 173-179.

Chung, Changkwon, et al., "Droplet dynamics passing through obstructions in confined microchannel flow", Microfluidics and Nanofluidics, vol. 9(6), May 17, 2010, 1151-1163.

Clausell-Tormos, J., et al., "Droplet-based microfluidic platforms for the encapsulation and screening of Mammalian cells and multicellular organisms", Chemistry and Biology, vol. 15(5), May 2008, 427-437.

Dejournette, Cheryl J, et al., "Creating Biocompatible Oil-Water Interfaces without Synthesis: Direct Interactions between Primary Amines and Carboxylated Perfluorocarbon Surfactants", Analytical chemistry, vol. 85 (21), Sep. 26, 2013, 10556-10564.

Dietrich, G J, et al., "Effects of UV irradiation and hydrogen peroxide on DNA fragmentation, motility and fertilizing ability of rainbow trout (*Oncorhynchus mykiss*) spermatozoa", Theriogenology vol. 64(8), Nov. 2005, 1809-1822.

Duffy, David C, et al., "Rapid Prototyping of Microfluidic Systems in Poly(dimethylsiloxane)", Anal. Chem., vol. 70(23), Oct. 24, 1998, 4974-4984.

Eastburn, Dennis J, et al., "Picoinjection enables digital detection of RNA with droplet rt-PCR", PLoS One vol. 8(4), Apr. 26, 2013, e62961.

Eastburn, Dennis J, et al., "Ultrahigh-Throughput Mammalian Single-Cell Reverse-Transcriptase Polymerase Chain Reaction in Microfluidic Drops", Anal. Chem. 85 (16), Jul. 26, 2013, 8016-8021.

Edd, Jon F, et al., "Controlled encapsulation of single-cells into monodisperse picolitre drops", Lab Chip, vol. 8(8), Aug. 2008, 1262-1264.

Frenz, Lucas, et al., "Reliable microfluidic on-chip incubation of droplets in delay-lines", Lab on a Chip vol. 9(10), May 21, 2009, 1344-1348.

Fu, Yusi, et al., "Uniform and accurate single-cell sequencing based on emulsion whole-genome amplification", Proc. Nall. Acad. Sci. USA, vol. 112(38), Sep. 22, 2015, 11923-11928.

Garstecki, Piotr, et al., "Formation of droplets and bubbles in a microfluidic T-junction-scaling and mechanism of break-up", Lab on a Chip, vol. 6(3), Apr. 2006, 437-446.

Gevensleben, Heidrun, et al., "Non-invasive Detection of HER2 Amplification with Plasma DNA Digital PCR", Clinical Cancer Research, vol. 19(12), May 2013, 3276-3284.

Gribskov, M, et al., "Sigma factors from *E. coli*, B. subtilis, phage SP01, and phage T4 are homologous proteins", Nucleic Acids Res., vol. 14(16), Aug. 26, 1986, 6745-6763.

Grover, Alka, et al., "Multiple displacement amplification as a pre-polymerase chain reaction (pre-PCR) to detect ultra low population of Ralstonia solanacearum (Smith 1896) Yabuchi et al. (1996)", Letters in Applied Microbiology, vol. 49(5), Jul. 2009, 539-543.

Hayward, Ryan C, et al., "Dewetting instability during the formation of polymersomes from block-copolymer-stabilized double emulsions", Langmuir, vol. 22(10), Apr. 11, 2006, 4457-4461.

Herminghaus, S, "Dynamical Instability of Thin Liquid Films Between Conducting Media", Physical Review Letter, vol. 83(12), Sep. 20, 1999, 2359-2361.

Holland, P M, et al., "Detection of specific polymerase chain reaction product by utilizing the 5'-3' exonuclease activity of Thermus aquaticus DNA polymerase", Proc Natl Acad Sci USA, 88 (16), Aug. 15, 1991, 7276-7280.

Holtze, C, et al., "Biocompatible surfactants for water-in-fluorocarbon emulsions", Lab Chip 8(10), Oct. 2008, 1632-1639.

Horton, Robert M, et al., "Gene splicing by overlap extension: tailor-made genes using the polymerase chain reaction", Biotechniques, vol. 54, Mar. 2013, 129-133.

Hu, Hoa, et al., "Mutation screening in 86 known X-linked mental retardation genes by droplet-based multiplex PCR and massive parallel sequencing", Hugo J., vol. 3 (1-4), Dec. 2009, 41-49.

Huebner, Ansgar, et al., "Microdroplets: A sea of applications?", Lab on a Chip, vol. 8(8), Aug. 2008, 1244-1254.

Hunkapiller, Tim, et al., "Immunology: The growing immunoglobulin gene superfamily", Nature vol. 323, Sep. 4, 1986, 15-16.

Hunt, Josephine A, et al., "Effect of pH on the stability and surface composition of emulsions made with whey protein isolate", Journal of Agricultural and Food Chemistry, vol. 42(10), Oct. 1, 1994, 2131-2135.

Huston, J S, et al., "Protein engineering of antibody binding sites: recovery of specific activity in an anti-digoxin single-chain Fv analogue produced in *Escherichia coli*", Proc. Natl. Acad. Sci. U.S.A. vol. 85(16), Aug. 1988, 5879-5883.

Kawasaki, Ernest S, "Sample Preparation From Blood, Cells, and Other Fluids", Chapter 18 of PCR Protocols: A guide to methods and Applications, 1990, 146-152.

Ki, Jang-Seu, et al., "Integrated Method for Single-Cell DNA Extraction, PCR Amplification, and Sequencing of Ribosomal DNA from Harmful Dinoflagellates Cochlodinium polykrikoides and Alexandrium catenella", Marine Biotechnology, vol. 6, 2004, 587-593.

Kiss, Margaret M, et al., "High-Throughput Quantitative Polymerase Chain Reaction in Picoliter Droplets", Anal Chem vol. 80(23), Dec. 1, 2008, 8975-8981.

Kritikou, Ekat, "It's cheaper in the Picolab", Nat Rev Genet, vol. 6, Sep. 2005, 668.

Küster, Simon K, et al., "Interfacing Droplet Microfluidics with Matrix-Assisted Laser Desorption/Ionization Mass Spectrometry: Label-Free Content Analysis of Single Droplets", Anal Chem vol. 85(3), Jan. 5, 2013, 1285-1289.

Lagally E T, et al., "Single-Molecule DNA Amplification and Analysis in an Integrated Microfluidic Device", Analytical Chemistry, vol. 73(3), Jan. 3, 2001, 565-570.

Lanzavecchia, Antonio, et al., "The use of hybrid hybridomas to target human cytotoxic T lymphocytes", Eur. J. Immunology, vol. 17(1), 1987, 105-111.

Leary, James F, "Strategies for rare cell detection and isolation", Methods Cell Biol., vol. 42, 1994, 331-358.

(56) References Cited

OTHER PUBLICATIONS

Lim, Shaun W, et al., "Ultrahigh-throughput sorting of microfluidic drops with flow cytometry", Lab on a Chip, vol. 13, Oct. 8, 2013, 4563-4572.
Link, D R, et al., "Geometrically mediated breakup of drops in microfluidic devices", Phys. Rev. Lett., vol. 92(5), Feb. 6, 2004, 054503.
Livak, K J, et al., "Analysis of Relative Gene Expression Data Using Real-Time Quantitative PCR and the 2(-Delta Delta C(T)) Method", Methods, vol. 25(4), Dec. 2001, 402-408.
Longo, M C, et al., "Use of uracil DNA glycosylase to control carry-over contamination in polymerase chain reactions", Gene, vol. 93(1), Sep. 1, 1990, 125-128.
Malloggi, Florent, et al., "Electrowetting-controlled droplet generation in a microfluidic flow-focusing device", Journal of Physics Condensed Matter, vol. 19(46), 462101, Oct. 2007, 1-7.
Marcus, Joshua S, et al., "Parallel Picoliter rt-PCR Assays Using Microfluidics", Analytical Chemistry, vol. 78(3), Feb. 1, 2006, 956-958.
Markou, Athina, et al., "Molecular Characterization of Circulating Tumor Cells in Breast Cancer by a Liquid Bead Array Hybridization Assay", Clinical Chemistry vol. 57(3), Mar. 2011, 421-430.
Mary, Pascaline, et al., "Controlling droplet incubation using close-packed plug flow", Biomicrofluidics, vol. 5(2), Apr. 4, 2011, 24101.
Mazutis, Linas, et al., "Single-cell analysis and sorting using droplet-based microfluidics", Nature protocols, vol. 8(5), Apr. 4, 2013, 870-891.
McDonald, J C, et al., "Fabrication of microfluidic systems in poly(dimethylsiloxane)", Electrophoresis, vol. 21(1), Jan. 2000, 27-40.
Medkov, Martina, et al., "Analyzing Cancer at Single Cell Resolution with Droplet Technology", American Association of Cancer Research (AACR), Apr. 19, 2010, 1 page.
Metzker, Michael L, "Sequencing technologies—the next generation", Nature Reviews Genetics, vol. 11, Jan. 2010, 31-46.
Miyazaki, Ryo, et al., "A new large-DNA-fragment delivery system based on integrase activity from an integrative and conjugative element", Appl Environ Microbiol vol. 79(14), Jul. 2013, 4440-4447.
Miyazaki, Kentaro, "Random DNA fragmentation with endonuclease V: application to DNA shuffling", vol. 30(24), Dec. 15, 2002, pp. 139.
Moon, Sangjun, et al., "Drop-on-Demand Single Cell Isolation and Total RNA Analysis", vol. 6 Issue 3, Mar. 2011, pp. 1-10.
Morton, Keith J, et al., "Crossing microfluidic streamlines to lyse, label and wash cells", Lab Chip vol. 8(9), Sep. 2008, 1448-1453.
Mui, B. L, et al., "Osmotic properties oflarge unilamellar vesicles prepared by extrusion", vol. 64(2), Feb. 1993, 443-453.
Nagrath, Sunitha, et al., "Isolation of rare circulating tumour cells in cancer patients by microchip technology", Nature, vol. 450, Dec. 20, 2007, 1235-1239.
Extended European Search Report received for European Patent Application Serial No. 17885180.4 dated Jul. 20, 2020, 11 pages.
Extended European Search Report received for European Patent Application Serial No. 17840230.1 dated Apr. 30, 2020, 12 pages.
Spencer, Sarah J., et al., "Massively parallel sequencing of single cells by epicPCR links functional genes with phylogenetic markers", The ISME Journal 10, 2016, 427-436.
Abate, Adam R., et al., (2013) "DNA sequence analysis with droplet-based microfluids", Lab Chip, vol. 13(24), pp. 4864-4869.
Abate, Adam R., et al., (2009) "Beating Poisson encapsulation statistics using close-packed ordering", Lab Chip, vol. 9, pp. 2628-2631.
Abbaspourrad, et al., (2015) "Label-free single-cell protein quantification using a dropbased mix-and-read system", Sci. Rep., 5, p. 12756.
Agargel, (2019) "Agar-Agar", retrieved on Jun. 6, 2019 from https://web.archive.org/web/20170527222040/http://www.agargel.com.br/agar-tecen. html, 3 pages.

Autour, et al., (2017) "Ultrahigh-throughput improvement and discovery of enzymes using droplet-based microfluidic screening" Micromachines, vol. 8(128), pp. 1-21.
Baker, (2012) "Digital PCR hits its stride", Nat. Methods, vol. 9(6), pp. 541-544.
Bjork, et al., (2012) "Metabolite profiling of microfluidic cell culture conditions for droplet based screening", Biomicrojluidics, vol. 9, p. 044128.
Blainey, et al., (2014) "Dissecting genomic diversity, one cell at a time" Nat. Methods, vol. 11(1), pp. 19-21.
Chang, et al., (2012) "Single Molecule Enzyme-Linked Immunosorbent Assays: Theoretical Considerations", J Immunol Methods, vol. 378(1-2), pp. 102-115.
Chen et al., (2017) "Centrifugal micro-channel array droplet generation for highly parallel digital PCR", Lab Chip, 17, pp. 235-240.
Chen et al., (2016) "Spinning micropipette liquid emulsion generator for single cell whole genome amplification", Lab Chip, 16, pp. 4512-4516.
Civelek et al., (2014) "Systems genetics approaches to understand complex traits", Nat. Rev. Genet., 15(1), pp. 34-48.
Collins et al., (2015) "The Poisson distribution and beyond: methods for microfluidic droplet production and single cell encapsulation", Lab on a Chip, 15, pp. 3439-3459.
Costa et al., (2008) "Complex networks: The key to systems biology", Genet. Mol. Biol., 31(3), pp. 591-601.
Elnifro, et al., (2000) "Multiplex PCR: Optimization and Application in Diagnostic Virology", Clin. Microbial. Rev., 13, pp. 559-570.
Fritzsch et al., (2012), "Single-Cell Analysis in Biotechnology, Systems Biology, and Biocatalysis", Annu. Rev. Chem. Biomol. Eng. 3, pp. 129-155.
Gielen, et al., (2016) "Ultrahigh-throughput-directed enzyme evolution by absorbance activated droplet sorting (AADS)", PNAS, pp. E7383-E7389.
Griffiths, et al., (2006) "Miniaturising the laboratory in emulsion droplets", Trends Biotechnol., 24, pp. 395-402.
Guo, et al., (2012) "Droplet microfluidics for highthroughput biological assays.", Lab Chip, pp. 2146-2155.
Halldorsson et al., (2015) "Advantages and challenges of microfluidic cell culture in polydimethylsiloxane devices", Biosens. Bioelectron., 63, pp. 218-231.
Huang, et al., (2017) "Collective generation of milliemulsions by step-emulsification", RSC Advances, 7, pp. 14932-14938.
Joanicot, et al., (2005) "Droplet control for microfluidics", Science, 309(5736), pp. 887-888.
Katepalli, et al., (2014) "Bose, A. Response of Surfactant Stabilized Oil-in-Water Emulsions to the Addition of Particles in an Aqueous Suspension", Langmuir, 30(43), pp. 12736-12742.
Kim, et al., (2017) "Measurement of copy number variation in single cancer cells using rapid-emulsification digital droplet MDA", Microsystems & Nanoengineering 3:17018, pp. 1-7.
Kim, et al., (2014) "Droplet Microfluidics for Producing Functional Microparticles", Langmuir, 30, pp. 1473-1488.
Kimmerling et al., (2016) "A microfluidic platform enabling single-cell RNA-seq of multigenerational lineages", Nature Commun., 7, p. 10220.
Kolodziejczyk, et al., (2015) "The Technology and Biology of Single-Cell RNA Sequencing", Mol. Cell, 58(4), pp. 610-620.
Lance, et al., (2016) "Peering below the diffraction limit: robust and specific sorting of viruses with flow cytometry", Viral J, 13, p. 201.
Macosko, et al., (2015) "Highly parallel genome-wide expression profiling of individual cells using nanoliter droplets" Cell, 161, pp. 1202-1214.
Margulies, et al., (2005) "Genome sequencing in microfabricated high-density picolitre reactors", Nature, 437, pp. 376-380.
Mashaghi, et al., (2016) "Droplet microfluidics: A tool for biology, chemistry and nanotechnology", TrAC—Trends Anal. Chem., 82, pp. 118-125.
Morimoto, et al.,(2013) "Three-dimensional cell culture based on microfluidic techniques to mimic living tissues", Biomaterials Science, vol. 1, No. 3, pp. 257-264.

(56) References Cited

OTHER PUBLICATIONS

Morimoto, et al., (2009) "Reconstruction of 3D Hierarchic Micro-Tissues using Monodisperse Collagen Microbeads", Micro Electro Mechanical Systems, IEEE 22nd International Conference, pp. 56-59.
Pinheiro, et al., (2012) Evaluation of a droplet digital polymerase chain reaction format for DNA copy number quantification, Anal. Chem., 84, pp. 1003-1011.
Romero, et al., (2015) "Dissecting enzyme function with microfluidic-based deep mutational scanning", PNAS, 112(23), pp. 7159-7164.
Sandberg, et al., (2009) "Flow cytometry for enrichment and titration in massively parallel DNA sequencing", Nucleic Acids Res, 37(8), p. e63.
Song, et al., (2006) "On-Chip Titration of an Anticoagulant Argatroban and Determination of the Clotting Time within Whole Blood or Plasma Using a Plug-Based Microfluidic System", Anal. Chem., 78(14), pp. 4839-4849.
Soon, et al., (2013) "High-throughput sequencing for biology and medicine", Mol. Syst. Biol., 9(64), pp. 1-14.
Spies, et al., (2017) "Genome-wide reconstruction of complex structural variants using read clouds", Nat. Methods, 14(9), pp. 915-920.
Sukovich, et al., (2017) "Sequence specific sorting of DNA molecules with FACS using 3dPCR", Sci. Rep., 7, p. 39385.
Taly, et al., (2013) "Multiplex picodroplet digital PCR to detect KRAS mutations in circulating DNA from the plasma of colorectal cancer patients", Clin. Chem., 59, pp. 1722-1731.
Tran, et al., (2013) "From tubes to drops: dropletbased biology microfluidics for ultrahigh-throughput", J Phys. D. Appl. Phys., 46, p. 114004.
Weaver, et al., (2014) "Advances in high-throughput single-cell microtechnologies", Curr. Opin. Biotechnol., 0, pp. 114-123.
Yan, et al., (2017) "Intestinal Enteroendocrine Lineage Cells Possess Homeostatic and Injury-Inducible Stem Cell Activity", Cell Stem Cell, 21, pp. 78-90.
Zhu, et al., (2017) "Hydrogel Droplet Microfluidics for High-Throughput Single Molecule/Cell Analysis", Acc. Chem. Res., 50(1), pp. 22-31.
Zilionis, et al., (2017) "Single-cell barcoding and sequencing using droplet microfluidics", Nat. Protoc., 12(1), pp. 44-73.

* cited by examiner

Robust double-emulsion device

COMBINED MULTIPLE-DISPLACEMENT AMPLIFICATION AND PCR IN AN EMULSION MICRODROPLET

CROSS-REFERENCE

This application claims priority to U.S. Provisional Application Ser. No. 62/373,317, filed Aug. 10, 2016, which application is incorporated by reference herein in its entirety. This application is related to, and incorporates by reference herein, the disclosure of U.S. Patent Application Publication No. 2015/0232942.

GOVERNMENT SUPPORT

This invention was made with government support under grant nos. AR068129, RO1 EB019453 and R21 HG007233, awarded by the National Institutes of Health. The government has certain rights in the invention.

INTRODUCTION

The quantitation and sequencing of nucleic acids is central to modern biology. New methods for detecting and quantitating nucleic acids, such as digital polymerase chain reaction (PCR), provide greater accuracy than traditional real-time quantitative PCR, and also provide an absolute count of the number of molecules present, obviating the need for an internal standard. Droplet PCR has emerged as a convenient high-throughput method for implementing digital PCR. However, a drawback to existing droplet digital PCR techniques is that in some cases subsequent sequencing steps will benefit from greater quantities of input DNA than is currently provided by such techniques. In addition, for methods which utilize FACS to sort microdroplets, such sorting may result in the introduction of contaminating DNA which overwhelms the amount of sorted DNAs of interest in the context of DNA library preparations. The present disclosure addresses the above issues and provides related advantages.

SUMMARY

The methods and systems described herein provide an improved emulsion droplet based nucleic acid amplification method, which allows nucleic acids contained in biological systems to be detected, quantitated and/or sorted based on their sequence as detected with nucleic acid amplification techniques, e.g., PCR. The nucleic acids can be free floating or contained within living or nonliving structures, including particles, viruses, and cells. The nucleic acids can include, e.g., DNA or RNA. The present disclosure is based in part on the surprising discovery that non-specific amplification techniques, such as Multiple Displacement Amplification (MDA), can be performed in the same emulsion microdroplet as Polymerase Chain Reaction (PCR). Systems and devices for use in practicing methods of the disclosure are also provided.

In exemplary embodiments, the disclosed methods include encapsulating a sample, which may include a heterogeneous population of cells, viruses, and/or nucleic acids, in a plurality of emulsion microdroplets, e.g., single emulsion microdroplets or multiple-emulsion microdroplets or Giant Unilamellar Vesicles (GUVs), wherein each multiple-emulsion microdroplet or GUV includes a first miscible phase fluid surrounded by an immiscible shell, wherein the multiple-emulsion microdroplet or GUV is positioned in a second miscible phase carrier fluid. In some embodiments, the sample may be diluted prior to encapsulation, e.g., so as to encapsulate a controlled number of cells, viruses, and/or nucleic acids in the multiple-emulsion microdroplets or GUVs. Nucleic acid amplification reagents, e.g., non-specific nucleic acid amplification reagents (e.g., MDA reagents) and PCR reagents, may be added to the single emulsion microdroplets or multiple-emulsion microdroplets or GUVs at the time of encapsulation or added to the single emulsion microdroplets or multiple-emulsion microdroplets or GUVs at a later time using one or more of the methods described herein. The single emulsion microdroplets or multiple-emulsion microdroplets or GUVs are then subjected to nucleic acid amplification conditions sufficient to result in both non-specific amplification and subsequent PCR amplification, such that if a single emulsion microdroplets or multiple-emulsion microdroplet or GUV contains a nucleic acid corresponding to a target of interest, e.g., a cell, virus, or nucleic acid of interest, the single emulsion microdroplets or multiple-emulsion microdroplet or GUV becomes detectably labeled, e.g., fluorescently labeled as a result of a fluorogenic assay, such as Sybr staining of amplified DNA or TaqMan® PCR. To recover the target nucleic acids or entities comprising the target nucleic acids, the detectably labeled single emulsion microdroplets or multiple-emulsion microdroplets or GUVs may be sorted using microfluidic (e.g., dielectrophoresis, membrane valves, etc.) or non-microfluidic techniques (e.g., FACS). The non-specific amplification step provides for an increased quantity of target nucleic acid for subsequent PCR amplification and detection.

Multiple-emulsion microdroplets according to the present disclosure may be formed, for example, by (1) flowing a miscible phase fluid, including, e.g., cells, viruses, and/or nucleic acids, along with nucleic acid amplification reagents in a channel of a microfluidic device; (2) contacting the miscible phase fluid with an immiscible phase fluid, e.g., using a single-emulsion droplet maker, wherein the contacting of the miscible phase fluid solution of nucleic acids and amplification reagents with the immiscible phase fluid results in the formation of miscible phase microdroplets (e.g., single emulsion microdroplets) surrounded by the immiscible phase fluid; (3) flowing the miscible phase microdroplets surrounded by the immiscible phase fluid in a channel of a microfluidic device; (4) contacting the miscible phase microdroplets surrounded by the immiscible phase fluid with a miscible phase carrier fluid, e.g., using a double-emulsion droplet maker, wherein the contacting of the miscible phase microdroplets surrounded by the immiscible phase fluid with the miscible phase carrier fluid results in the formation of multiple-emulsion microdroplets (e.g., double-emulsion microdroplets), each multiple-emulsion microdroplet including a miscible phase microdroplet surrounded by the immiscible phase fluid, wherein the immiscible phase fluid is surrounded by the miscible phase carrier fluid. GUVs may be generated from multiple-emulsion microdroplets by inducing the multiple-emulsion microdroplets to undergo dewetting, wherein the immiscible phase fluid is expunged, leaving behind a membrane of surfactant with a small immiscible phase droplet adhered to the outside of the membrane. One or more steps of the method may be performed under microfluidic control.

In some embodiments, a sample including viruses is encapsulated in single emulsion microdroplets or multiple-emulsion microdroplets or GUVs and subjected to nucleic acid amplification conditions as described herein. In some embodiments, the encapsulated viruses are subjected to one or more virus lysing techniques, such as proteinase k digestion or thermal lysis. Nucleic acid amplification assays specific to the viruses of interest can cause single emulsion microdroplets or multiple-emulsion microdroplets or GUVs containing the viruses of interest, or nucleic acids originating from the viruses of interest, to become detectably labeled, e.g., fluorescently labeled. The viruses and/or the viral nucleic acids, may then be recovered by sorting the single emulsion microdroplets or multiple-emulsion microdroplets or GUVs and recovering their contents via microdroplet rupture, e.g., through chemical or electrical means.

In some embodiments, a sample, e.g., a sample including cells, is encapsulated in single emulsion microdroplets or multiple-emulsion microdroplets or GUVs and subjected to nucleic acid amplification conditions as described herein. In some embodiments, the sample, e.g., a sample including encapsulated cells, is subjected to one or more cell lysing techniques, such as proteinase k digestion or thermal lysis. For example, cell-containing microdroplets may be contacted with a protease to digest cellular proteins. Suitable proteases for use in methods of the present disclosure include those that are well known in the art, e.g., a serine protease, a subtilisin-type protease, e.g., proteinase K, brofasin, and the like. In some embodiments, microdroplets are incubated with proteinase K under conditions sufficient to digest cellular proteins, e.g., at 50° C. for 30 minutes or any other suitable temperature and time sufficient to digest cellular proteins contained within the microdroplets.

Nucleic acid amplification assays specific to the cells of interest can cause single emulsion microdroplets or multiple-emulsion microdroplets or GUVs containing the cells of interest, or nucleic acids originating from the cells of interest, to become detectably labeled, e.g., fluorescently labeled. The cells and/or the cellular nucleic acids may then be recovered by sorting the single emulsion microdroplets or multiple-emulsion microdroplets or GUVs and recovering their contents via microdroplet rupture, e.g., through chemical or electrical means.

Additional nucleic acid amplification reactions which may be performed in single emulsion microdroplets or multiple-emulsion microdroplets or GUVs as described herein, include, e.g., strand displacement amplification (SDA), and rolling circle amplification (RCA).

In one aspect of a method according to the present disclosure, a method for enriching for a target nucleic acid sequence is provided, wherein the method includes encapsulating a sample including nucleic acids in a plurality of single emulsion microdroplets or multiple-emulsion microdroplets or GUVs; introducing Multiple Displacement Amplification (MDA) reagents and polymerase chain reaction (PCR) reagents, including appropriate primers, into the single emulsion microdroplets or multiple-emulsion microdroplets or GUVs; incubating the single emulsion microdroplets or multiple-emulsion microdroplets or GUVs under conditions sufficient for MDA amplification followed by conditions sufficient for PCR amplification to produce PCR amplification products, wherein suitable PCR primers may include one or more primers that each hybridize to one or more oligonucleotides comprised by the target nucleic acid sequence, and wherein the PCR amplification products do not include the entire target nucleic acid sequence; introducing a detection component into the single emulsion microdroplets or multiple-emulsion microdroplets or GUVs either before or after the incubating; detecting the presence or absence of the PCR amplification products by detection of the detection component, wherein detection of the detection component indicates the presence of PCR amplification products and the target nucleic acid sequence; and sorting the single emulsion microdroplets or multiple-emulsion microdroplets or GUVs based on detection of the detection component, wherein the sorting separates single emulsion microdroplets or multiple-emulsion microdroplets or GUVs including the PCR amplification products and the target nucleic acid sequence, when present, from single emulsion microdroplets or multiple-emulsion microdroplets or GUVs which do not include the PCR amplification products and the target nucleic acid sequence; and pooling the nucleic acid sequences from the sorted single emulsion microdroplets or multiple-emulsion microdroplets or GUVs to provide an enriched pool of target nucleic acid sequences, when present. One or more of these steps may be performed under microfluidic control. The above steps may be followed by one or more sequencing steps, e.g., one or more next generation sequencing techniques.

As described herein, the term "next-generation sequencing" generally refers to advancements over standard DNA sequencing (e.g., Sanger sequencing). Although standard DNA sequencing enables the practitioner to determine the precise order of nucleotides in the DNA sequence, next-generation sequencing also provides parallel sequencing, during which millions of base pair fragments of DNA can be sequenced in unison. Standard DNA sequencing generally requires a single-stranded DNA template molecule, a DNA primer, and a DNA polymerase in order to amplify the DNA template molecule. Next-generation sequencing facilitates high-throughput sequencing, which allows for an entire genome to be sequenced in a significantly shorter period of time relative to standard DNA sequencing. Next-generation sequencing may also facilitate in identification of disease-causing mutations for diagnosis of pathological conditions. Next-generation sequencing may also provide information on the entire transcriptome of a sample in a single analysis without requiring prior knowledge of the genetic sequence.

Any suitable non-specific nucleic acid amplification methods and reagents, e.g., MDA methods and reagents, may be utilized in connection with the disclosed methods provided that such methods and reagents are compatible with any additional, e.g., subsequent, amplification steps and or reagents of the method, e.g., PCR amplification steps and reagents. An example of a suitable MDA polymerase, which may be used in combination with a Taq DNA polymerase is a Bst polymerase. Bst polymerase may have advantages over other MDA polymerases, such as phi29 polymerase, since Bst polymerase is efficient over a wider temperature range and is active under similar buffer conditions to Taq DNA polymerase.

In practicing the subject methods, a wide range of different PCR-based assays may be employed, such as quantitative PCR (qPCR). The number and nature of primers used in such assays may vary, based at least in part on the type of assay being performed, the nature of the biological sample, and/or other factors. In certain aspects, the number of primers that may be added to a microdroplet, e.g., a multiple-emulsion microdroplet, or a GUV may be 1 to 100 or more, and/or may include primers to detect from about 1 to 100 or more different genes (e.g., oncogenes). In addition to, or instead of, such primers, one or more probes (e.g., TaqMan® probes) may be employed in practicing the subject methods.

As used herein, the terms "drop," "droplet," and "microdroplet" may be used interchangeably to refer to tiny, generally spherical, microcompartments containing at least a first fluid phase, e.g., an aqueous phase (e.g., water), bounded by a second fluid phase (e.g., oil) which is immiscible with the first fluid phase. In some embodiments, the second fluid phase will be an immiscible phase carrier fluid. Droplets as used or generated in connection with the subject methods, devices, and/or systems may be sphere shaped or they may have any other suitable shape, e.g., an ovular or oblong shape. Microdroplets, including, e.g., multiple-emulsion microdroplets, generally have a dimension, e.g., diameter, which ranges from about 0.1 to about 1000 µm, and may be used to encapsulate cells, DNA, enzymes, and other components. In some embodiments, microdroplets, e.g., multiple emulsion microdroplets, have a dimension, e.g., diameter of about 1.0 µm to 1000 µm, inclusive, such as 1.0 µm to 750 µm, 1.0 µm to 500 µm, 1.0 µm to 100 µm, 1.0 µm to 10 µm, or 1.0 µm to 5 µm, inclusive. In some embodiments, droplets as described herein have a dimension, e.g., diameter, of about 1.0 µm to 5 µm, 5 µm to 10 µm, 10 µm to 100 µm, 100 µm to 500 µm, 500 µm to 750 µm, or 750 µm to 1000 µm, inclusive. Accordingly, the above terms may be used to refer to a microdroplet, e.g., a multiple emulsion microdroplet, produced in, on, or by a microfluidics device.

GUVs, which may be formed from double emulsion microdroplets, are generally of a similar size as the double emulsion microdroplets from which they originate. Accordingly, GUVs according to the present disclosure may have a dimension, e.g., diameter which ranges from about 0.1 to about 1000 µm.

The microdroplets, e.g., multiple-emulsion microdroplets, or GUVs themselves may vary, including in size, composition, contents, and the like. Microdroplets or GUVs may generally have an internal volume of from about 0.001 to 1000 picoliters or more, e.g., from about 0.001 picoliters to about 0.01 picoliters, from about 0.01 picoliters to about 0.1 picoliters, from about 0.1 picoliters to about 1 picoliter, from about 1 picoliter to about 10 picoliters, from about 10 picoliters to about 100 picoliters, or from about 100 picoliters to about 1000 picoliters or more. Further, microdroplets may or may not be stabilized by surfactants and/or particles.

As used herein, the term "carrier fluid" refers to a fluid configured or selected to contain one or more droplets, as described herein. A carrier fluid may include one or more substances and may have one or more properties, e.g., viscosity, which allows it to be flowed through a microfluidic device or a portion thereof. In some embodiments, carrier fluids include, for example: oil or water, and may be in a liquid or gas phase.

The means by which reagents are added to a microdroplet, e.g., a multiple-emulsion microdroplet, or GUV may vary greatly. Reagents may be added in one step or in multiple steps, such as 2 or more steps, 4 or more steps, or 10 or more steps. In certain aspects, reagents may be added to multiple-emulsion microdroplets or GUVs via one or more encapsulation and rupture steps. For example, in some embodiments, the disclosed method may include a step of encapsulating a suitable sample, e.g., a virus, cell or nucleic acid, in a first multiple-emulsion microdroplet or GUV, encapsulating one or more reagents and the first multiple-emulsion microdroplet or GUV in a second multiple-emulsion microdroplet or GUV, and rupturing the first multiple-emulsion microdroplet or GUV thereby bringing the sample into contact with the one or more reagents.

In one such embodiment, cells are encapsulated into double emulsions or GUVs along with a suitable lysis buffer, incubated under conditions sufficient for cell lysis and/or protein digestion, and heated to inactivate proteases. The double emulsions or GUVs may then be encapsulated into double emulsions or GUVs containing suitable nucleic acid amplification reagents and ruptured so as to release their contents into the encapsulating double emulsions or GUVs, thereby mixing the cell lysate with the nucleic acid amplification reagents. The remaining double emulsions or GUVs may then be incubated under conditions suitable for nucleic acid amplification.

As a variation on the above method, cells may be encapsulated into single emulsions with a suitable lysis buffer. Following an optional protease inactivation step, single emulsions may then be merged via droplet merger with single emulsions containing suitable nucleic acid amplification reagents. The merged single emulsion microdroplets may then be encapsulated into double emulsions or GUVs for subsequent nucleic acid amplification. Alternatively, cells may be encapsulated into single emulsions with a suitable lysis buffer and then, following an optional protease inactivation step, encapsulated into nucleic acid amplification reagent-containing double emulsions or GUVs. It should be noted that steps of encapsulation into single emulsions and steps of encapsulation into double emulsions may be performed on the same microfluidic device or using two or more different microfluidic devices, which may or may not be fluidically connected.

In some embodiments, the disclosed methods may include a step of encapsulating one or more reagents in a first multiple-emulsion microdroplet or GUV, encapsulating a suitable sample, e.g., a virus, cell or nucleic acid, and the first multiple-emulsion microdroplet or GUV in a second multiple-emulsion microdroplet or GUV, and rupturing the first multiple-emulsion microdroplet or GUV thereby bringing the sample into contact with the one or more reagents.

In some embodiments, the disclosed methods may include a step of adding a reagent to the second multiple-emulsion microdroplet or GUV, wherein the adding comprises encapsulating a first multiple-emulsion microdroplet or GUV comprising the reagent in the second multiple-emulsion microdroplet or GUV and rupturing the first multiple-emulsion microdroplet or GUV within the second multiple-emulsion microdroplet or GUV to bring the reagent into contact with the contents of the second multiple-emulsion microdroplet or GUV.

As mentioned above, where single emulsion droplets are utilized as part of the disclosed methods, a variety of techniques applicable to single emulsion droplets may be utilized, including, e.g., droplet coalescence, picoinjection, multiple droplet coalescence, and the like, as shall be described more fully herein. In certain embodiments, reagents are added by a method in which the injection fluid itself acts as an electrode. The injection fluid may contain one or more types of dissolved electrolytes that permit it to be used as such. Where the injection fluid itself acts as the electrode, the need for metal electrodes in the microfluidic chip for the purpose of adding reagents to a droplet may be obviated. In certain embodiments, the injection fluid does not act as an electrode, but one or more liquid electrodes are utilized in place of metal electrodes.

Various ways of detecting the absence or presence of nucleic acid amplification products may be employed, using a variety of different detection components. Detection components of interest include, but are not limited to, fluorescein and its derivatives; rhodamine and its derivatives; cyanine and its derivatives; coumarin and its derivatives; Cascade Blue and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like. Detection components may include beads (e.g., magnetic or fluorescent beads, such as Luminex beads) and the like. In certain aspects, detection may involve holding a microdroplet at a fixed position during thermal cycling so it can be repeatedly imaged. Such repeated imaging may involve the use of a Megadroplet Array, as shall be described more fully herein. In certain aspects, detection may involve fixing and/or permeabilizing one or more cells in one or more microdroplets, e.g., one or more multiple-emulsion microdroplets, or GUVs.

Suitable subjects for the methods disclosed herein include mammals, e.g., humans. The subject may be one that exhibits clinical presentations of a disease condition, or has been diagnosed with a disease. In certain aspects, the subject may be one that has been diagnosed with cancer, exhibits clinical presentations of cancer, or is determined to be at risk of developing cancer due to one or more factors such as family history, environmental exposure, genetic mutation(s), lifestyle (e.g., diet and/or smoking), the presence of one or more other disease conditions, and the like. In certain aspects, the subject may be one that has been diagnosed with a microbial infection, exhibits clinical presentations of a microbial infection, or is determined to be at risk of developing a microbial infection due to one or more factors such as family history, environmental exposure, genetic mutation(s), lifestyle (e.g., diet and/or travel), the presence of one or more other disease conditions, and the like. In certain aspects, the subject may be one that has been diagnosed with a viral infection, exhibits clinical presentations of a viral infection, or is determined to be at risk of developing a viral infection due to one or more factors such as family history, environmental exposure, genetic mutation(s), lifestyle (e.g., diet and/or travel), the presence of one or more other disease conditions, and the like.

Microfluidic systems and devices are also provided by the present disclosure. In certain aspects, a microfluidic system according to the present disclosure includes a sample loading region, e.g., a cell loading region; a single emulsion droplet maker in fluid communication with the sample loading region, a double-emulsion droplet maker; a nucleic acid amplification region, and a detection region. In some embodiments, the double emulsion droplet maker is in fluid communication with the single emulsion droplet maker. In other embodiments, it may be provided as a distinct system component which is not connected fluidically to the single emulsion droplet maker. In some embodiments, the nucleic acid amplification region may include a thermal cycler. In some embodiments, the nucleic acid amplification region is fluidically connected to the double emulsion droplet maker. In some embodiments, the system includes a detection region, which detects the presence or absence of reaction products from the nucleic acid amplification region, and which may be fluidically connected to the nucleic acid amplification region. In some embodiments, the system includes one or more chambers fluidically connected to the single-emulsion droplet maker. Such chambers may include, e.g., means for adding a first reagent to a single emulsion microdroplet, and/or a heating element. In some embodiments, the system includes a sorting region or a combination detection/sorting region fluidically connected to the nucleic acid amplification region. In some embodiments, alternatively or in addition to an "on-chip" sorting region, sorting of the microdroplets may occur "off-chip". For example, in the case of aqueous phase-in immiscible phase-in aqueous phase double emulsions, an off chip flow cytometry device, e.g., a FACS device, may be utilized for sorting. In some embodiments, a system including one or more elements as described above is embodied in one or more microfluidic devices.

BRIEF DESCRIPTION OF THE DRAWINGS

The invention may be best understood from the following detailed description when read in conjunction with the accompanying drawings. Included in the drawings are the following figures:

FIG. 2, Panel A, shows an embodiment in which PCR reagents and nucleic acids are introduced into a flow channel of a microfluidic device in an aqueous fluid. A single emulsion droplet maker introduces a fluid which is immiscible with the aqueous fluid, e.g., oil, to form single emulsion microdroplets containing the PCR reagents and nucleic acids. The single emulsion microdroplets are then reinjected into a second flow channel of a microfluidic device (Panel B). A double emulsion droplet maker introduces a fluid which is miscible with the aqueous fluid, e.g., water, along with a suitable surfactant, e.g., a detergent, to form double emulsion microdroplets containing the PCR reagents and nucleic acids. While depicted as separate components in FIG. 2, it should be noted that a single emulsion droplet maker and a double emulsion droplet maker may be provided as fluidically connected components in a single microfluidic device in some embodiments of the disclosed devices, methods and systems. Following formation of the double emulsion microdroplets, the double emulsion microdroplets are collected for subsequent PCR amplification. Such PCR amplification may occur in a thermalcycler integrated into a microfluidic device, e.g., a microfluidic device including one or more of the single and double emulsion droplet makers, or "off chip" in a separate thermalcycler.

FIG. 4 also provides an image (bottom right) of an "M-junction" portion of a microfluidic device which can be used to prepare double emulsions in accordance with the present disclosure.

FIG. 4 shows a bright field image (left) of the PCR amplified double emulsions, a FITC readout (center), and a merged bright field-FITC readout (right).

Top panel shows the side scatter versus forward scatter of the double emulsions shown a clear population of large entities, corresponding to the double emulsions. Lower panels show the side scatter versus the fluorescence channel (FITC) for the gated population of "large" events on the upper right of the SSC×FSC plot. As the concentration of Lambda virus increases, more double emulsions are detected as being fluorescent as shown by comparing from left to right in the lower panel.

Figure 18:
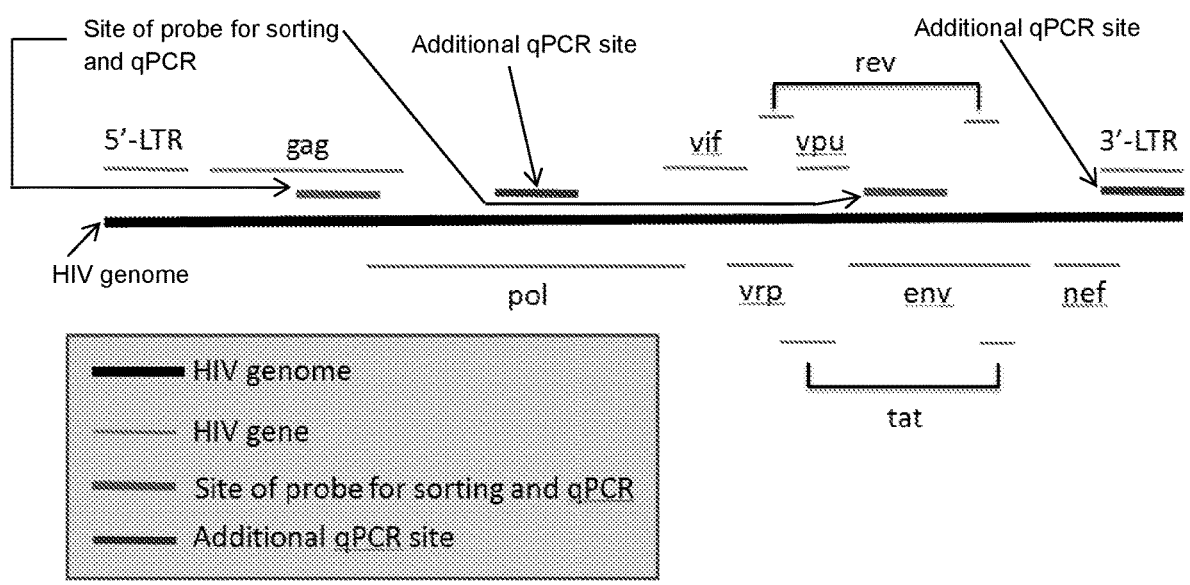

FIG. 18 provides a diagram of the HIV provirus genome, genes, and locations of primers used for genomic detection in droplets and qPCR analysis of sorted molecules. The provirus is embedded within the human genome at a location that can vary from cell to cell. The sample is fragmented into ~100 kb molecules and the molecules sorted based on whether they contain a provirus genome. The gag primer set is used in the first sort, the collected nucleic acids are diluted and then sorted a second time using the env primer set.

Figure 19:
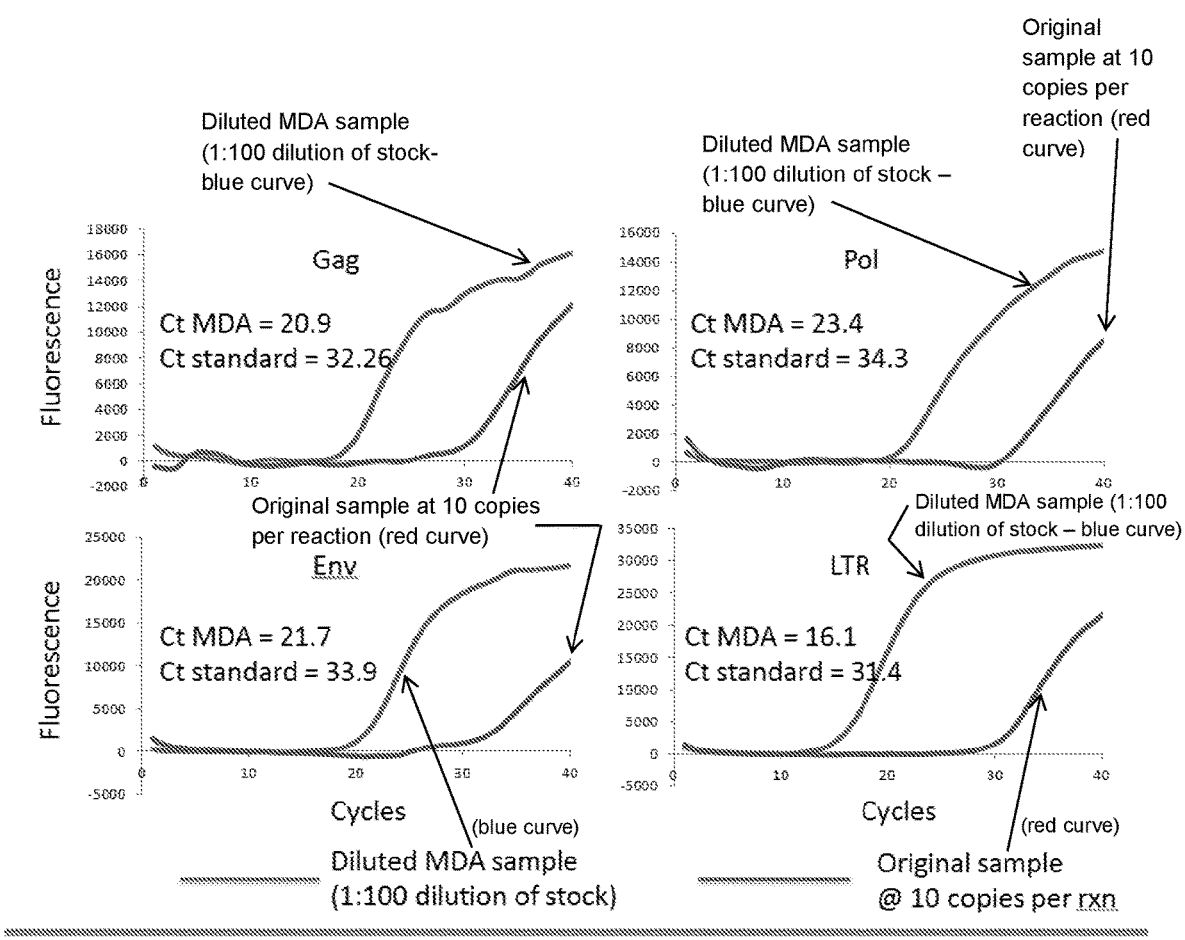

FIG. 19 provides graphs showing quantitative PCR (par) measurements of enrichment of HIV provirus out of human genomic DNA using MESA. The four panels correspond to par measurements for the gag, pol, env, and LTR primer sets. The red curves corresponds to the original sample of human genomic DNA in which HIV provirus is estimated to be present at a rate of 10 copies per sample, which is used as a standard. The blue curves correspond to measurements of the sorted samples after droplet MDA and a 100-fold dilution in buffer, so that the concentration of DNA in the samples corresponding to the blue and red curves are equal as measured with a UV-spectrometer. The blue and red curves are shifted by ~12 Ct curves, on average, corresponding to a ~4000× difference in target concentration. When correcting for the 100× of the sorted materiel, this leads to a ~400,000× estimated increase of the provirus in the MESA enriched sample. The sample was sorted using two consecutive rounds of MESA.

Figure 20:
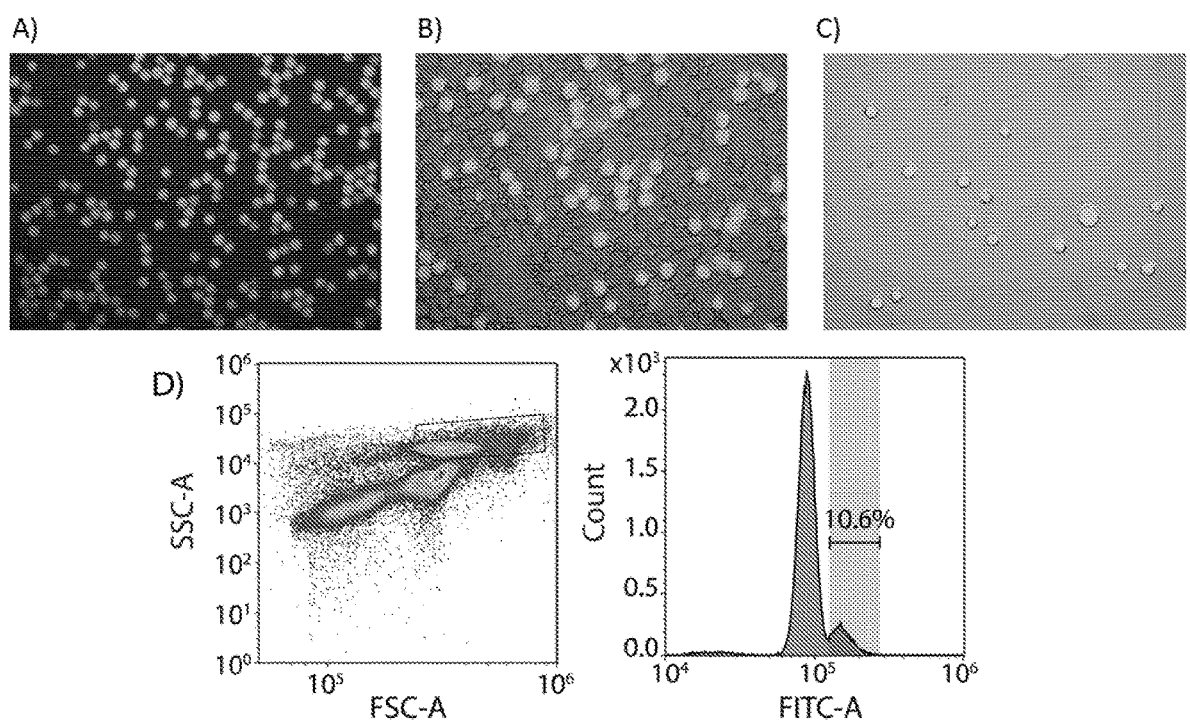

FIG. 20 provides images of TaqMan® PCR for T4 as single emulsions Panel (A) and double emulsions Panel (B). Panel (C) provides an image showing fluorescent double emulsions containing T4 recovered from FACS sort. Panel (D) shows FSC-A (front scatter-area) against SSC-A (side scatter-area) log-log plots and FITC channel fluorescence frequency histograms for double emulsions. Fluorescence plots are derived by gating events in defined areas on the FSC-A/SSC-A plots. The percentage of fluorescent droplets sorted is indicated.

Figure 21:
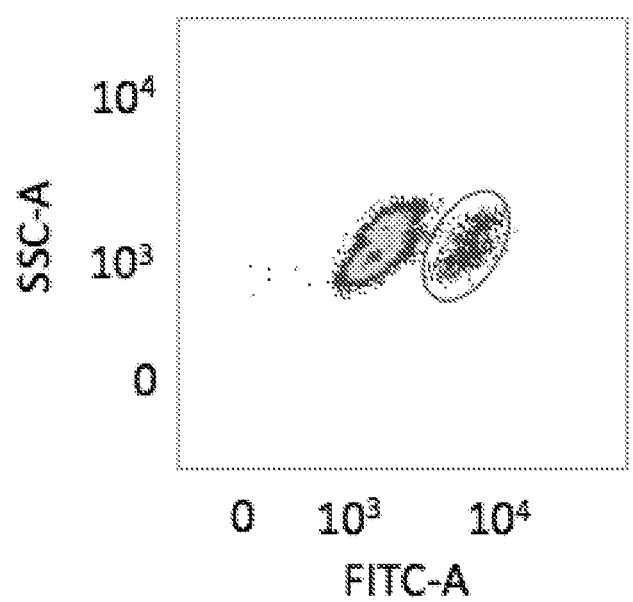

FIG. 21 provides a gated scatter plot showing the results of flow cytometer sorting based upon the absolute FITC fluorescence of the emulsions in Example 9.

Figure 22:
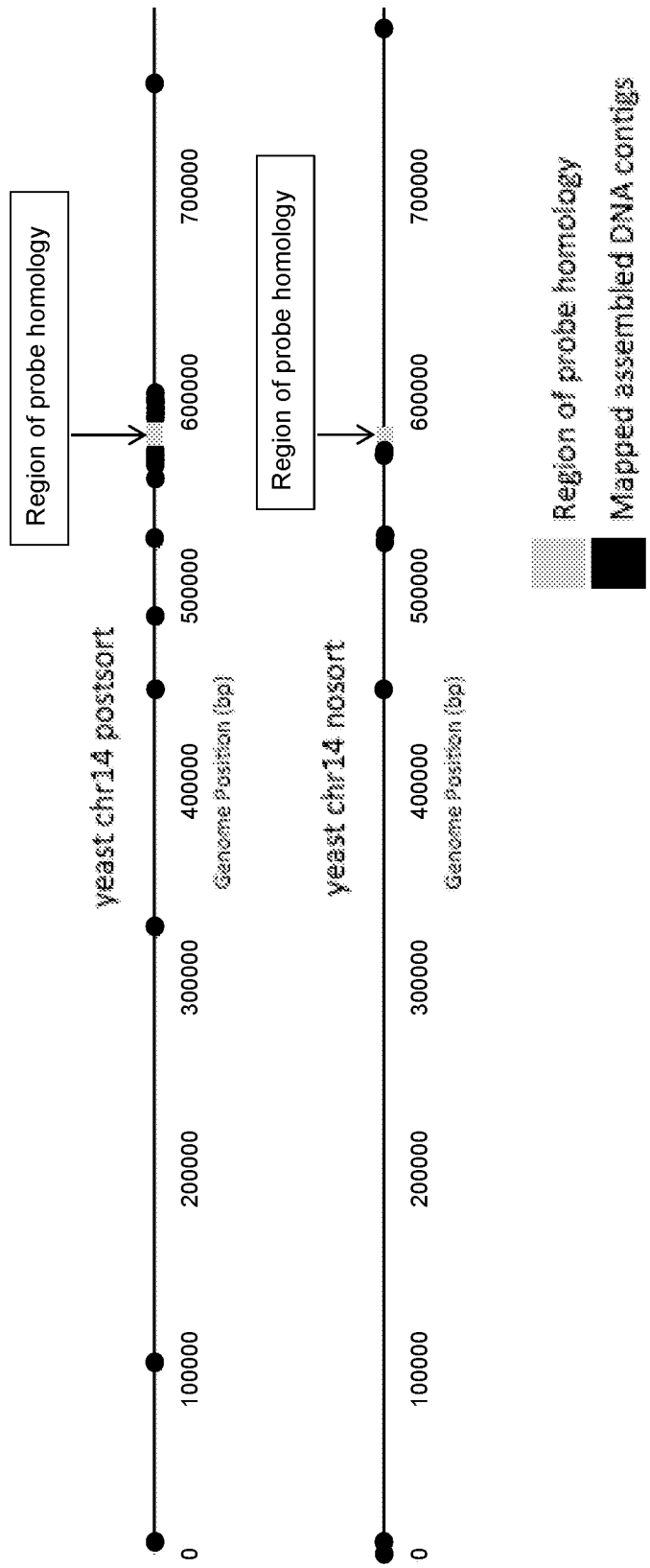

FIG. 22 shows the mapped assembled DNA contigs for Example 9. The top map corresponds to the sorted positive emulsions while the bottom map corresponds to the unsorted emulsions.

DETAILED DESCRIPTION

The methods and systems described herein provide an improved emulsion droplet-based nucleic acid amplification method, which allows nucleic acids contained in biological systems to be detected, quantitated and/or sorted based on their sequence as detected with nucleic acid amplification techniques, e.g., PCR. The nucleic acids can be free floating or contained within living or nonliving structures, including particles, viruses, and cells. The nucleic acids can include, e.g., DNA or RNA. The present disclosure is based in part on the surprising discovery that non-specific amplification techniques, such as Multiple Displacement Amplification (MDA), can be performed in the same emulsion microdroplet as Polymerase Chain Reaction (PCR). Systems and devices for use in practicing methods of the disclosure are also provided.

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a microdroplet" includes a plurality of such microdroplets and reference to "the multiple-emulsion microdroplet" includes reference to one or more multiple-emulsion microdroplets, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Further, the dates of publication provided may be different from the actual publication dates which may need to be independently confirmed. To the extent such publications may set out a definition or disclosure that conflicts with the explicit or implicit definition or disclosure of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the present disclosure include methods for the detection and/or sorting of components from biological samples using single emulsion microdroplets and/or multiple-emulsion microdroplets and/or GUVs. Aspects include methods for the detection, quantification, and/or genotyping of cells, e.g. normal mammalian cells (e.g., non-tumor cells), tumor cells, e.g., circulating tumor cells (CTCs), or microbial cells. Additional embodiments of interest include PCR-based detection and/or sorting of cells, PCR-based detection and/or sorting of viral particles and PCR-based detection and/or sorting of nucleic acids from a heterogeneous population of nucleic acids.

As used herein, the term "biological sample" encompasses a variety of sample types obtained from a variety of sources, which sample types contain biological material. For example, the term includes biological samples obtained from a mammalian subject, e.g., a human subject, and biological samples obtained from a food, water, or other environmental source, etc. The definition encompasses blood and other liquid samples of biological origin, as well as solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, cells, serum, plasma, biological fluid, and tissue samples. "Biological sample" includes cells, e.g., bacterial cells or eukaryotic cells; biological fluids such as blood, cerebrospinal fluid, semen, saliva, and the like; bile; bone marrow; skin (e.g., skin biopsy); and antibodies obtained from an individual.

As used herein the term "isolated," when used in the context of an isolated cell, refers to a cell of interest that is in an environment different from that in which the cell naturally occurs. "Isolated" is meant to include cells that are within samples that are substantially enriched for the cell of interest and/or in which the cell of interest is partially or substantially purified.

As described more fully herein, in various aspects the subject methods may be used to detect a variety of components from such biological samples. Components of interest include, but are not necessarily limited to, cells (e.g., circulating cells and/or circulating tumor cells), viruses, polynucleotides (e.g., DNA and/or RNA), polypeptides (e.g., peptides and/or proteins), and many other components that may be present in a biological sample.

The terms "nucleic acid", "nucleic acid molecule", "oligonucleotide" and "polynucleotide" are used interchangeably and refer to a polymeric form of nucleotides of any length, either deoxyribonucleotides or ribonucleotides, or analogs thereof. The terms encompass, e.g., DNA, RNA and modified forms thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

"Polynucleotides" or "oligonucleotides" as used herein refer to linear polymers of nucleotide monomers, and may be used interchangeably. Polynucleotides and oligonucleotides can have any of a variety of structural configurations, e.g., be single stranded, double stranded, or a combination of both, as well as having higher order intra- or intermolecular secondary/tertiary structures, e.g., hairpins, loops, triple stranded regions, etc. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, *Human Molecular Genetics* 2 (Wiley-Liss, New York, 1999).

The terms "polypeptide," "peptide," and "protein," used interchangeably herein, refer to a polymeric form of amino acids of any length. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-3559 is used.

In certain aspects, methods are provided for counting and/or genotyping cells, including normal cells or tumor cells, such as CTCs. A feature of such methods is the use of microfluidics.

Figure 1:
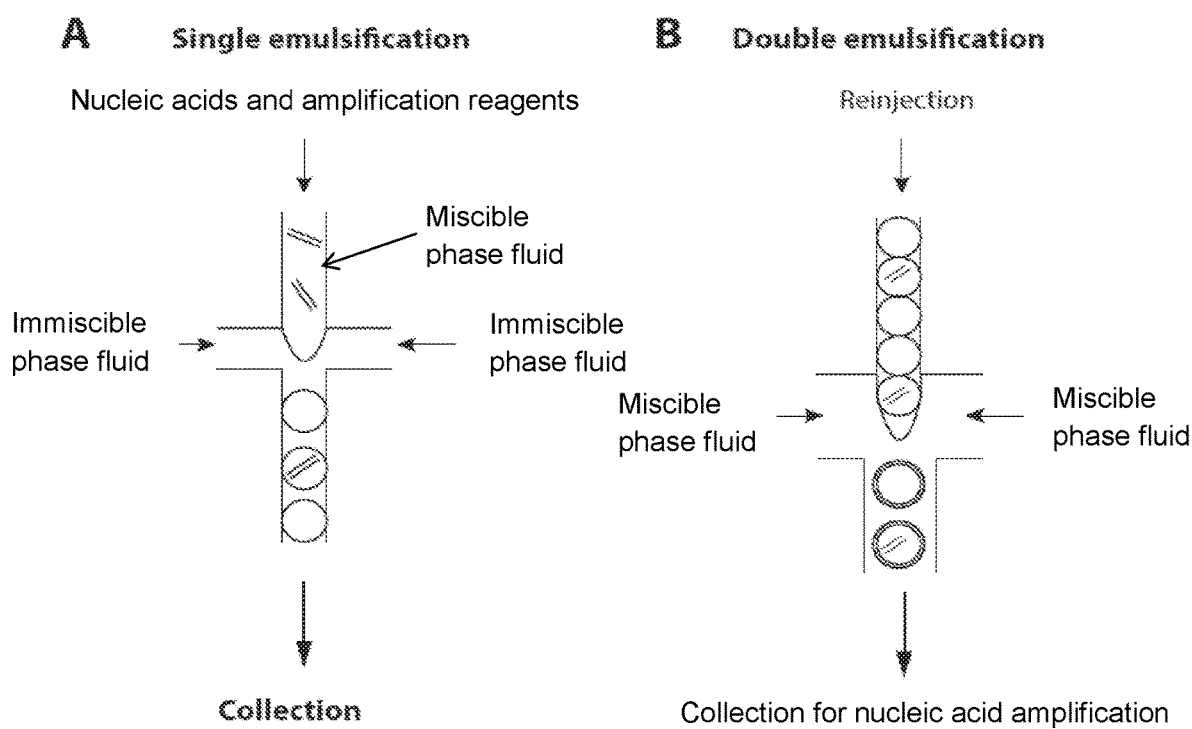
FIG. 1 is a schematic showing double emulsion formation via two-step emulsification according to some embodiments of the present disclosure. Panel A depicts schematically the formation of a miscible phase-in-immiscible phase single emulsion, e.g., a water-in-oil or oil-in-water single emulsion. Panel B depicts schematically the formation of a miscible phase-in-immiscible phase-in-miscible phase double emulsion, e.g., a water-in-oil-in-water double emulsion or an oil-in-water-in-oil double emulsion, after reinjection of the miscible phase-in-immiscible phase single emulsion. While depicted as separate components in FIG. 1, it should be noted that a single emulsion droplet maker and a double emulsion droplet maker may be provided as fluidically connected components in a single microfluidic device in some embodiments of the disclosed devices, methods and systems. Following formation of the double emulsion microdroplets, the double emulsion microdroplets are collected for subsequent nucleic acid amplification. Such nucleic acid amplification may occur in a nucleic acid amplification region of a microfluidic device, e.g., a microfluidic device including one or more of the single and double emulsion droplet makers, or "off chip" in a separate nucleic acid amplification apparatus.

As summarized above, the methods of the present disclosure generally involve nucleic acid amplification in single emulsion droplets or multiple-emulsion microdroplets and/or GUVs followed by detection and/or sorting of the single emulsion droplets or multiple-emulsion microdroplets and/or GUVs. FIG. 1 presents a schematic showing double emulsion formation via two-step emulsification according to some embodiments of the present disclosure. Panel A depicts schematically the formation of a miscible phase-in-immiscible phase single emulsion, e.g., a water-in-oil or oil-in-water single emulsion. Panel B depicts schematically the formation of a miscible phase-in-immiscible phase-in-immiscible phase double emulsion, e.g., a water-in-oil-in-water double emulsion or an oil-in-water-in-oil double emulsion, after reinjection of the miscible phase-in-immiscible phase single emulsion. While depicted as separate components in FIG. 1, it should be noted that a single emulsion droplet maker and a double emulsion droplet maker may be provided as fluidically connected components in a single microfluidic device in some embodiments of the disclosed devices, methods and systems. Following formation of the double emulsion microdroplets, the double emulsion microdroplets are collected for subsequent nucleic acid amplification. Such nucleic acid amplification may occur in a nucleic acid amplification region of a microfluidic device, e.g., a microfluidic device including one or more of the single and double emulsion droplet makers, or "off chip" in a separate nucleic acid amplification apparatus.

Alternatively, following formation of the double emulsion microdroplets, the double emulsion microdroplets may be subjected to dewetting conditions, forming GUVs, in which the immiscible phase fluid of the double emulsion is expunged from the shell, leaving behind a membrane of surfactant, with a small immiscible phase droplet adhered to the outside of the membrane.

Figure 2:
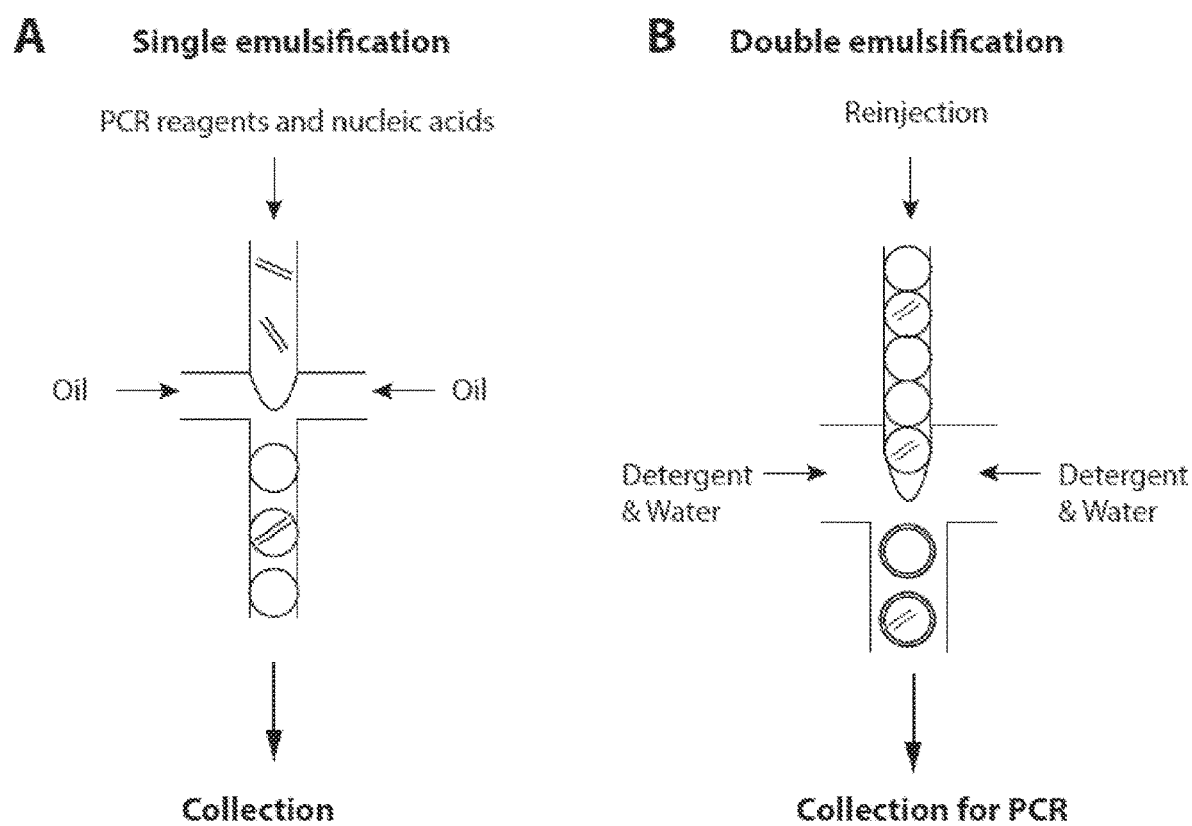
FIG. 2 is a schematic showing a more detailed embodiment of the double emulsion formation via two-step emulsification shown in FIG. 1.

FIG. 2 presents a schematic showing a more detailed embodiment of the double emulsion formation via two-step emulsification shown in FIG. 1. FIG. 2, Panel A, shows an embodiment in which PCR reagents and nucleic acids are introduced into a flow channel of a microfluidic device in an aqueous fluid. A single emulsion droplet maker introduces a fluid which is immiscible with the aqueous fluid, e.g., oil, to form single emulsion microdroplets containing the PCR reagents and nucleic acids. The single emulsion microdroplets are then reinjected into a second flow channel of a microfluidic device (Panel B). A double emulsion droplet maker introduces a fluid which is miscible with the aqueous fluid, e.g., water, along with a suitable surfactant, e.g., a detergent, to form double emulsion microdroplets containing the PCR reagents and nucleic acids. While depicted as separate components in FIG. 2, it should be noted that a single emulsion droplet maker and a double emulsion droplet maker may be provided as fluidically connected components in a single microfluidic device in some embodiments of the disclosed devices, methods and systems. Following formation of the double emulsion microdroplets, the double emulsion microdroplets are collected for subsequent PCR amplification. Such PCR amplification may occur in a thermalcycler integrated into a microfluidic device, e.g., a microfluidic device including one or more of the single and double emulsion droplet makers, or "off chip" in a separate thermalcycler.

Alternatively, following formation of the double emulsion microdroplets, the double emulsion microdroplets may be subjected to dewetting conditions, in which the immiscible phase fluid of the double emulsion is expunged from the shell, leaving behind a membrane of surfactant, with a small immiscible phase droplet adhered to the outside of the membrane.

For embodiments in which a thermalcycler is integrated into a microfluidic device single emulsion droplets or multiple-emulsion microdroplets or GUVs containing MDA reagents and PCR reagents may be flowed through a channel that incubates the droplets under conditions effective for MDA and PCR. By way of example, for MDA the appropriate conditions may be achieved by exposing the single emulsion droplets or multiple-emulsion microdroplets or GUVs to multiple cycles of MDA incubation (e.g., 1 to 10, 2 to 9, 3 to 8, 4 to 7, or 5 to 6 cycles), where a cycle includes incubation at, e.g., 25° C. for 5 min, followed by incubation at 42° C. for 25 min. For PCR the appropriate conditions may be achieved by flowing the single emulsion droplets or multiple-emulsion microdroplets and/or GUVs through a channel that snakes over various zones maintained at 65° C. and 95° C. or 86° C., 60° C. and 20° C. As the single emulsion droplets or multiple-emulsion microdroplets and/or GUVs move through the zones, their temperature cycles, as needed for PCR. During the PCR reaction, if a single emulsion droplet or multiple-emulsion microdroplet and/or GUV contains a nucleic acid which the selected primer(s) are designed to detect, amplification is initiated. The presence of these particular PCR products may be detected by, for example, a fluorescent output that turns the single emulsion droplets or multiple-emulsion microdroplets and/or GUVs fluorescent. The single emulsion droplets or multiple-emulsion microdroplets and/or GUVs may thus be scanned, such as by using flow cytometry, to detect the presence of fluorescent drops. In certain aspects, the single emulsion droplets or multiple-emulsion microdroplets and/or GUVs may also be sorted using, for example, droplet sorting to recover drops of interest Using the nomenclature of the current disclosure, the steps described above are thus performed "under microfluidic control." That is, the steps are performed on one or more microfluidics devices, or at least in part on one or more microfluidic devices.

Initial encapsulation of a component from a biological sample in a single emulsion microdroplet in accordance with the methods described herein may be achieved by any convenient means. Encapsulation approaches of interest also include, but are not limited to, hydrodynamically-triggered drop formation and those described by Link, et al., Phys. Rev. Lett. 92, 054503 (2004), the disclosure of which is incorporated herein by reference.

A feature of certain methods of the present disclosure is the use of a polymerase chain reaction (PCR)-based assay to detect the presence of certain oligonucleotides and/or genes, e.g., oncogene(s) present in cells. Examples of PCR-based assays of interest include, but are not limited to, quantitative PCR (qPCR), quantitative fluorescent PCR (QF-PCR), multiplex fluorescent PCR (MF-PCR), single cell PCR, PCR-RFLP/real time-PCR-RFLP, hot start PCR, nested PCR, in situ polony PCR, in situ rolling circle amplification (RCA), bridge PCR, picotiter PCR, emulsion PCR and reverse transcriptase PCR (RT-PCR). Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA).

A PCR-based assay may be used to detect the presence of certain gene(s), such as certain oncogene(s). In such assays, one or more primers specific to each gene of interest are reacted with the genome of each cell. These primers have sequences specific to the particular gene, so that they will only hybridize and initiate PCR when they are complementary to the genome of the cell. If the gene of interest is present and the primer is a match, many copies of the gene are created. To determine whether a particular gene is present, the PCR products may be detected through an assay probing the liquid of the single emulsion microdroplet or multiple-emulsion microdroplet and/or GUV, such as by staining the solution with an intercalating dye, like Sybr-Green or ethidium bromide, hybridizing the PCR products to a solid substrate, such as a bead (e.g., magnetic or fluorescent beads, such as Luminex beads), or detecting them through an intermolecular reaction, such as FRET. These dyes, beads, and the like are each examples of a "detection component," a term that is used broadly and generically herein to refer to any component that is used to detect the presence or absence of nucleic acid amplification products, e.g., PCR products.

A number of variations of these basic approaches will now be outlined in greater detail below.

Detecting Cells (e.g., Tumor Cells) in Multiple-Emulsion Microdroplets and/or GUVs Aspects of the subject methods involve detecting the presence of one or more cells or subsets of cells (e.g., tumor cells) in a biological sample. Such methods may include, for example, steps of encapsulating a cell in a multiple-emulsion microdroplet and/or GUV, the multiple-emulsion microdroplet and/or GUV including a first miscible phase fluid surrounded by an immiscible shell, wherein the multiple-emulsion microdroplet and/or GUV is positioned in a second miscible phase carrier fluid; subjecting the multiple-emulsion microdroplet and/or GUV to conditions sufficient to effect lysis of the cell in the multiple-emulsion microdroplet and/or GUV; subjecting the multiple-emulsion microdroplet and/or GUV to conditions sufficient to deactivate or remove one or more materials which have an inhibitory effect on nucleic acid amplification; introducing nucleic acid amplification reagents (e.g., MDA amplification reagents and/or PCR amplification reagents) into the multiple-emulsion microdroplet and/or GUV; subjecting the multiple-emulsion microdroplet and/or GUV to amplification conditions sufficient to result in amplification of a target nucleic acid when present; and detecting an amplification product resulting from the amplification of the target nucleic acid when present.

A biological sample (e.g., whole blood) may be recovered from a subject using any convenient means. The biological sample may be processed to remove components other than cells using, for example, processing steps such as centrifugation, filtration, and the like. Where desired, the cells may be stained with one or more antibodies and/or probes prior to encapsulating them into multiple-emulsion microdroplets and/or GUVs.

One or more lysing agents may also be added to the multiple-emulsion microdroplets and/or GUVs containing a cell, under conditions in which the cell(s) may be caused to burst, thereby releasing their genomes. The lysing agents may be added after the cells are encapsulated into multiple-emulsion microdroplets and/or GUVs. Any convenient lysing agent may be employed, such as proteinase K or cytotoxins. In particular embodiments, cells may be co-encapsulated in multiple-emulsion microdroplets and/or GUVs with lysis buffer containing detergents such as Triton X100 and/or proteinase K. The specific conditions in which the cell(s) may be caused to burst will vary depending on the specific lysing agent used. For example, if proteinase K is incorporated as a lysing agent, the multiple-emulsion microdroplets and/or GUVs may be heated to about 37-60° C. for about 20 min to lyse the cells and to allow the proteinase K to digest cellular proteins, after which they may be heated to about 95° C. for about 5-10 min to deactivate the proteinase K.

In certain aspects, cell lysis may also, or instead, rely on techniques that do not involve addition of lysing agent. For example, lysis may be achieved by mechanical techniques that may employ various geometric features to effect piercing, shearing, abrading, etc. of cells. Other types of mechanical breakage such as acoustic techniques may also be used. Further, thermal energy can also be used to lyse cells. Any convenient means of effecting cell lysis may be employed in the methods described herein.

Primers may be introduced into the multiple-emulsion microdroplets and/or GUVs for each of the genes and/or genetic markers, e.g., oncogenes, to be detected. Hence, in certain aspects, primers for a variety of genes and/or genetic markers, e.g., all oncogenes may be present in the multiple-emulsion microdroplets and/or GUVs at the same time, thereby providing a multiplexed assay. The multiple emulsion microdroplets and/or GUVs may be temperature-cycled so that multiple emulsion microdroplets and/or GUVs containing target cells, e.g., cancerous cells, will undergo PCR. Alternatively, or in addition, MDA or other isothermal nucleic acid amplification methods may be utilized, e.g., loop-mediated isothermal amplification (LAMP), strand displacement amplification (SDA), helicase-dependent amplification (HDA), and nicking enzyme amplification reaction (NEAR). Only the primers corresponding to oncogenes and/or genetic markers present in the genome will induce amplification, creating many copies of these oncogenes and/or genetic markers in the multiple emulsion microdroplets and/or GUVs. Detecting the presence of these amplification products may be achieved by a variety of ways, such as by using FRET, staining with an intercalating dye, or attaching them to a bead. The multiple emulsion microdroplets and/or GUVs may be optically probed to detect the amplification products. In some embodiments, optically probing the multiple emulsion microdroplets and/or GUVs may involve counting the number of tumor cells present in the initial population, and/or allowing for the identification of the oncogenes present in each tumor cell.

The subject methods may be used to determine whether a biological sample contains particular cells of interest, e.g., tumor cells, or not. In certain aspects, the subject methods may include quantifying the number of cells of interest, e.g., tumor cells, present in a biological sample. Quantifying the number of cells of interest, e.g., tumor cells, present in a biological sample may be based at least in part on the number of multiple emulsion microdroplets and/or GUVs in which amplification products were detected. For example, multiple emulsion microdroplets and/or GUVs may be produced under conditions in which the majority of microdroplets are expected to contain zero or one cell. Those multiple emulsion microdroplets and/or GUVs that do not contain any cells may be removed, using techniques described more fully herein. After performing the PCR steps outlined above, the total number of multiple emulsion microdroplets and/or GUVs that are detected to contain amplification products may be counted, so as to quantify the number of cells of interest, e.g., tumor cells, in the biological sample. In certain aspects, the methods may also include counting the total number of multiple emulsion microdroplets and/or GUVs so as to determine the fraction or percentage of cells from the biological sample that are cells of interest, e.g., tumor cells.

In some embodiments, the introduction of amplification reagents (e.g., MDA amplification reagents and/or PCR amplification reagents) into the multiple-emulsion microdroplets and/or GUVs includes introducing the amplification reagents into the second miscible phase carrier fluid, wherein the amplification reagents diffuse from the second miscible phase carrier fluid, through the immiscible shell, and into the first miscible phase fluid of the multiple-emulsion microdroplets and/or GUVs.

The cells and/or cellular material of interest may be recovered by sorting the multiple-emulsion microdroplets and/or GUVs and recovering their contents via microdroplet rupture, e.g., through chemical, electrical, or mechanical means as described in greater detail herein. A variety of suitable sorting techniques and related devices may be utilized to sort and separate the multiple-emulsion microdroplets and/or GUVs containing amplification products including those described herein. The above method could also be performed in single emulsions.

Nucleic Acid Detection in Multiple-Emulsion Micodroplets and/or GUVs

As discussed herein, the disclosed methods find use in the detection of nucleic acids, e.g., DNA or RNA, of interest from a variety of biological samples. Such methods may include, for example, steps of encapsulating a nucleic acid and amplification reagents (e.g., MDA amplification reagents and/or PCR amplification reagents) in a multiple-emulsion microdroplet and/or GUV, the multiple-emulsion microdroplet and/or GUV including a first miscible phase fluid surrounded by an immiscible shell, wherein the multiple-emulsion microdroplet and/or GUV is positioned in a second miscible phase carrier fluid; and subjecting the multiple-emulsion microdroplet and/or GUV to amplification conditions sufficient to result in amplification of the nucleic acid; and detecting an amplification product resulting from the amplification of the nucleic acid. In some embodiments, the second miscible phase carrier fluid is a buffered aqueous phase carrier fluid, and in some embodiments the first and second miscible phase fluids are the same. The amplification conditions may be MDA conditions and PCR conditions e.g., RT-PCR conditions, and/or additional isothermal amplification conditions, e.g., loop-mediated isothermal amplification (LAMP), strand displacement amplification (SDA), helicase-dependent amplification (HDA), and nicking enzyme amplification reaction (NEAR).

The nucleic acids of interest may be recovered by sorting the multiple-emulsion microdroplets and/or GUVs and recovering their contents via microdroplet rupture, e.g., through chemical, electrical, or mechanical means as described in greater detail herein. A variety of suitable sorting techniques and related devices may be utilized to sort and separate the multiple-emulsion microdroplets and/or GUVs containing amplification products including those described herein. The above method could also be performed in single emulsions.

In one aspect, a method for enriching for a target nucleic acid sequence is provided, wherein the method includes encapsulating a sample including nucleic acids in a plurality of multiple-emulsion microdroplets and/or GUVs; introducing MDA reagents and polymerase chain reaction (PCR) reagents and a plurality of suitable primers into the multiple-emulsion microdroplets and/or GUVs; incubating the multiple-emulsion microdroplets and/or GUVs under conditions sufficient for MDA amplification and conditions sufficient for PCR amplification to produce MDA amplification products and PCR amplification products, respectively, wherein suitable PCR primers may include one or more primers that each hybridize to one or more oligonucleotides comprised by the target nucleic acid sequence, and wherein the PCR amplification products do not include the entire target nucleic acid sequence; introducing a detection component into the multiple-emulsion microdroplets and/or GUVs either before or after the incubating; detecting the presence or absence of the PCR amplification products by detection of the detection component, wherein detection of the detection component indicates the presence of PCR amplification products and the target nucleic acid sequence; and sorting the multiple-emulsion microdroplets and/or GUVs based on detection of the detection component, wherein the sorting separates multiple-emulsion microdroplets and/or GUVs including the PCR amplification products and the target nucleic acid sequence, when present, from multiple-emulsion microdroplets and/or GUVs which do not include the PCR amplification products and the target nucleic acid sequence; and pooling the nucleic acid sequences from the sorted multiple-emulsion microdroplets and/or GUVs to provide an enriched pool of target nucleic acid sequences, when present. One or more of these steps may be performed under microfluidic control. The above method could also be performed in single emulsions.

The above method allows, for example, for the enrichment of DNA molecules out of a heterogeneous system based on the presence of PCR-detectable subsequences. The DNA molecules can be short (e.g., hundreds of bases) or long (e.g., megabases or longer). The sample may be encapsulated in microdroplets such that target molecules are detected in the microdroplets digitally—i.e., each microdroplet contains 0 or 1 target molecule. The microdroplets may then be sorted based on, e.g., fluorescence, to recover the target molecules. This method can be used to enrich for a large genomic region, e.g., on the order of megabases in length, in a heterogeneous sample of DNA fragments.

The above method enables a sufficient amount of DNA to be recovered without the need to perform PCR to amplify the DNA for sequencing. Amplification-free DNA sample prep is valuable, for example, where PCR does not preserve the sequences or epigenetic factors of interest, or cannot recover sequences that are of the needed length (e.g., > about 10 kb, the practical limit of long-range PCR).

Another application of the above method is to enrich DNA for epigenetic sequencing. Epigenetic marks on DNA are not preserved by PCR, so sequencing them requires unamplified DNA from the host nucleic acids. With the above method, a sufficient amount of DNA can be obtained for sequencing without needing to perform PCR, and thus preserving the epigenetic marks.

The above methods have particular utility where the length of the target nucleic acid exceeds the practical limits of long-range PCR, e.g., where the nucleic acid is greater than about 10 kb, and/or where it is desirable to preserve epigenetic marks on the DNA. In some embodiments, the target nucleic acid to be enriched is greater than about 100 kb in length, e.g., greater than about 1 megabase in length. In some embodiments, the target nucleic acid to be enriched is from about 10 kb to about 100 kb, from about 100 kb to about 500 kb, or from about 500 kb to about 1 megabase in length.

Post-amplification and/or purification, emulsions can be broken using both chemical and osmotic means for future analysis. For example, an equal volume of 1H, 1H, 2H, 2H-Perfluoro-1-octanol can be added to a purified sample and mixed either through pipetting or vortexing. The resulting mixture can then be allowed to equilibrate, and the aqueous layer can be eluted off for further analysis. Similarly, a large excess of purified water can be added to the sample post-sort, mixed, and allowed to incubate at room temperature for several hours. The resulting mixture can then be analyzed directly for purified sample of interest.

Multiple Displacement Amplification

As summarized above, in practicing methods of the invention MDA may be used to amplify nucleic acids, e.g., genomic DNA, in a generally unbiased and non-specific manner for downstream analysis, e.g., via next generation sequencing. For clarity, MDA may be used as appropriate in connection with any of the methods described herein.

An exemplary embodiment of a method according to the present disclosure includes encapsulating in a microdroplet (e.g., single emulsion microdroplet or multiple emulsion microdroplet) a nucleic acid template molecule obtained from a biological sample, introducing MDA reagents and a plurality of MDA primers into the microdroplet, and incubating the microdroplet under conditions effective for the production of MDA amplification products, wherein the incubating is effective to produce MDA amplification products from the nucleic acid template molecule. In some embodiments the encapsulating and introducing steps occur as a single step, e.g., where the nucleic acid template molecule is mixed with MDA reagents and a plurality of MDA primers and emulsified, e.g., using a flow focusing element of a microfluidic device.

The conditions of MDA-based assays described herein may vary in one or more ways. For instance, the number of MDA primers that may be added to (or encapsulated in) a microdroplet may vary. The term "primer" refers to one or more primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as a suitable DNA polymerase (e.g., Φ29 DNA polymerase or Bst DNA polymerase), in a suitable buffer ("buffer" includes substituents which are cofactors, or which affect pH, ionic strength, etc.), and at a suitable temperature. The primer is preferably single-stranded for maximum efficiency in amplification. In the context of MDA, random hexamer primers are regularly utilized.

The complement of a nucleic acid sequence as used herein refers to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

The number of MDA primers that may be added to (or encapsulated in) a microdroplet may range from about 1 to about 500 or more, e.g., about 2 to 100 primers, about 2 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

Such primers and/or reagents may be added to a microdroplet in one step, or in more than one step. For instance, the primers may be added in two or more steps, three or more steps, four or more steps, or five or more steps. Where a lysing agent is utilized, regardless of whether the primers are added in one step or in more than one step, they may be added after the addition of a lysing agent, prior to the addition of a lysing agent, or concomitantly with the addition of a lysing agent. When added before or after the addition of a lysing agent, the MDA primers may be added in a separate step from the addition of a lysing agent.

Once primers have been added to a microdroplet, the microdroplet may be incubated under conditions sufficient for MDA. The microdroplet may be incubated on the same microfluidic device as was used to add the primer(s), or may be incubated on a separate device. In certain embodiments, incubating the microdroplet under conditions sufficient for MDA amplification is performed on the same microfluidic device used for cell lysis. Incubating the microdroplets may take a variety of forms, for example microdroplets may be incubated at a constant temperature, e.g., 30 deg. C., e.g., for about 8 to about 16 hours. Alternatively, cycles of 25° C. for 5 minutes followed by 42° C. for 25 minutes may be utilized.

Although the methods described herein for producing MDA amplification products do not require the use of specific probes, the methods of the invention may also include introducing one or more probes to the microdroplet. As used herein with respect to nucleic acids, the term "probe" generally refers to a labeled oligonucleotide which forms a duplex structure with a sequence in the target nucleic acid, due to complementarity of at least one sequence in the probe with a sequence in the target region. The probe, preferably, does not contain a sequence complementary to sequence(s) used to prime the MDA reaction. The number of probes that are added may be from about one to 500, e.g., about 1 to 10 probes, about 10 to 20 probes, about 20 to 30 probes, about 30 to 40 probes, about 40 to 50 probes, about 50 to 60 probes, about 60 to 70 probes, about 70 to 80 probes, about 80 to 90 probes, about 90 to 100 probes, about 100 to 150 probes, about 150 to 200 probes, about 200 to 250 probes, about 250 to 300 probes, about 300 to 350 probes, about 350 to 400 probes, about 400 to 450 probes, about 450 to 500 probes, or about 500 probes or more. The probe(s) may be introduced into the microdroplet prior to, subsequent with, or after the addition of the one or more primer(s).

In certain embodiments, an MDA based assay may be used to detect the presence of certain RNA transcripts present in cells or to sequence the genome of one or more RNA viruses. In such embodiments, MDA reagents may be added to the microdroplet using any of the methods described herein. Prior to or after addition (or encapsulation) of the MDA reagents, the microdroplet may be incubated under conditions allowing for reverse transcription followed by conditions allowing for MDA as described herein. The microdroplet may be incubated on the same microfluidic device as is used to add the MDA reagents, or may be incubated on a separate device. In certain embodiments, incubating the microdroplet under conditions allowing for MDA is performed on the same microfluidic device used to encapsulate and/or lyse one or more cells.

In certain embodiments, the reagents added to the microdroplet for MDA further includes a fluorescent DNA probe capable of detecting MDA amplification products. Any suitable fluorescent DNA probe can be used including, but not limited to SYBR Green, TaqMan®, Molecular Beacons and Scorpion probes. In certain embodiments, the reagents added to the microdroplet include more than one DNA probe, e.g., two fluorescent DNA probes, three fluorescent DNA probes, or four fluorescent DNA probes. The use of multiple fluorescent DNA probes allows for the concurrent measurement of MDA amplification products in a single reaction.

PCR

As summarized above, in practicing methods of the invention a PCR-based assay may be used to detect the presence of certain nucleic acids of interest, e.g., genes of interest and/or genetic markers, e.g., oncogene(s), present in cells or a heterogeneous sample of nucleic acids. Such PCR based assays may be performed in the same microdroplet, e.g., single emulsion microdroplet or multiple emulsion microdroplet as a previous or subsequent MDA amplification step. The conditions of such PCR-based assays may vary in one or more ways.

For instance, the number of PCR primers that may be added to a single emulsion microdroplet or multiple-emulsion microdroplet and/or GUV may vary. The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

The complement of a nucleic acid sequence as used herein refers to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

The number of PCR primers that may be added to a single emulsion microdroplet or multiple-emulsion microdroplet and/or GUV may range from about 1 to about 500 or more, e.g., about 2 to 100 primers, about 2 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

These primers may contain primers for one or more gene of interest, e.g. oncogenes. The number of primers for genes of interest that are added may be from about one to 500, e.g., about 1 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more. Genes and oncogenes of interest include, but are not limited to, BAX, BCL2L1, CASP8, CDK4, ELK1, ETS1, HGF, JAK2, JUNB, JUND, KIT, KITLG, MCL1, MET, MOS, MYB, NFKBIA, EGFR, Myc, EpCAM, NRAS, PIK3CA, PML, PRKCA, RAF1, RARA, REL, ROS1, RUNX1, SRC, STAT3, CD45, cytokeratins, CEA, CD133, HER2, CD44, CD49f, CD146, MUC1/2, and ZHX2.

Such primers and/or reagents may be added to a single emulsion microdroplet or multiple-emulsion microdroplet and/or GUV in one step, or in more than one step. For instance, the primers may be added in two or more steps, three or more steps, four or more steps, or five or more steps. Regardless of whether the primers are added in one step or in more than one step, they may be added after the addition of a lysing agent, prior to the addition of a lysing agent, or concomitantly with the addition of a lysing agent. When added before or after the addition of a lysing agent, the PCR primers may be added in a separate step from the addition of a lysing agent.

Once primers have been added to a single emulsion microdroplet or multiple-emulsion microdroplet and/or GUV the single emulsion microdroplet or multiple-emulsion microdroplet and/or GUV may be incubated under conditions allowing for PCR. The single emulsion microdroplet or multiple-emulsion microdroplet and/or GUV may be incubated on the same microfluidic device as was used to add the primer(s), or may be incubated on a separate device. In certain embodiments, incubating the single emulsion microdroplet or multiple-emulsion microdroplet and/or GUV under conditions allowing for PCR amplification is performed on the same microfluidic device used to encapsulate and lyse cells. Incubating the single emulsion microdroplet or multiple-emulsion microdroplet and/or GUV may take a variety of forms. In certain aspects, the single emulsion microdroplet or multiple-emulsion microdroplet and/or GUV containing the PCR mix may be flowed through a channel that incubates the microdroplets under conditions effective for PCR. Flowing the single emulsion microdroplet or multiple-emulsion microdroplet and/or GUV through a channel may involve a channel that snakes over various temperature zones maintained at temperatures effective for PCR. Such channels may, for example, cycle over two or more temperature zones, wherein at least one zone is maintained at about 65° C. and at least one zone is maintained at about 95° C. Alternatively, zones for 86° C., 60° C. and 20° C. may be utilized. As the single emulsion microdroplets or multiple-emulsion microdroplets and/or GUVs move through such zones, their temperature cycles, as needed for PCR. The precise number of zones, and the respective temperature of each zone, may be readily determined by those of skill in the art to achieve the desired PCR amplification.

In other embodiments, incubating the single emulsion microdroplets or multiple-emulsion microdroplets and/or GUVs may involve the use of a Megadroplet Array. In such a device, an array of hundreds, thousands, or millions of traps indented into a channel (e.g., a PDMS channel) sit above a thermal system. The channel may be pressurized, thereby preventing gas from escaping. The height of the microfluidic channel is smaller than the diameter of the single emulsion microdroplets or multiple-emulsion microdroplets and/or GUVs, causing single emulsion microdroplets or multiple-emulsion microdroplets and/or GUVs to adopt a flattened pancake shape. When a single emulsion microdroplets or multiple-emulsion microdroplet and/or GUV flows over an unoccupied indentation, it adopts a lower, more energetically favorable, radius of curvature, leading to a force that pulls the single emulsion microdroplets or multiple-emulsion microdroplet and/or GUV entirely into the trap. By flowing single emulsion microdroplets or multiple-emulsion microdroplets and/or GUVs as a close pack, it is ensured that all traps on the array are occupied. The entire device may be thermal cycled using a heater.

In certain aspects, the heater includes a Peltier plate, heat sink, and control computer. The Peltier plate allows for the heating or cooling of the chip above or below room temperature by controlling the applied current. To ensure controlled and reproducible temperature, a computer may monitor the temperature of the array using integrated temperature probes, and may adjust the applied current to heat and cool as needed. A metallic (e.g. copper) plate allows for uniform application of heat and dissipation of excess heat during cooling cycles, enabling cooling from about 95° C. to about 60° C. in under about one minute.

Methods of the invention may also include introducing one or more probes to the single emulsion microdroplets or multiple-emulsion microdroplets and/or GUVs. As used herein with respect to nucleic acids, the term "probe" refers to a labeled oligonucleotide which forms a duplex structure with a sequence in the target nucleic acid, due to complementarity of at least one sequence in the probe with a sequence in the target region. In some embodiments, the probe does not contain a sequence complementary to sequence(s) used to prime the polymerase chain reaction. The number of probes that are added may be from about one to 500, e.g., about 1 to 10 probes, about 10 to 20 probes, about 20 to 30 probes, about 30 to 40 probes, about 40 to 50 probes, about 50 to 60 probes, about 60 to 70 probes, about 70 to 80 probes, about 80 to 90 probes, about 90 to 100 probes, about 100 to 150 probes, about 150 to 200 probes, about 200 to 250 probes, about 250 to 300 probes, about 300 to 350 probes, about 350 to 400 probes, about 400 to 450 probes, about 450 to 500 probes, or about 500 probes or more. The probe(s) may be introduced into the multiple-emulsion microdroplets and/or GUVs prior to, subsequent with, or after the addition of the one or more primer(s). Probes of interest include, but are not limited to, TaqMan® probes (e.g., as described in Holland, P. M.; Abramson, R. D.; Watson, R.; Gelfand, D. H. (1991). "Detection of specific polymerase chain reaction product by utilizing the 5'----3' exonuclease activity of *Thermus aquaticus* DNA polymerase". PNAS, 88 (16): 7276-7280).

In certain embodiments, an RT-PCR based assay may be used to detect the presence of certain transcripts of interest, e.g., oncogene(s), present in cells. In such embodiments, reverse transcriptase and any other reagents necessary for cDNA synthesis are added to the single emulsion microdroplets or multiple-emulsion microdroplets and/or GUVs in addition to the reagents used to carry out PCR described herein (collectively referred to as the "RT-PCR reagents"). The RT-PCR reagents are added to the single emulsion microdroplets or multiple-emulsion microdroplets and/or GUVs using any of the suitable methods described herein. Once reagents for RT-PCR have been added to a single emulsion microdroplet or multiple-emulsion microdroplet and/or GUV, the single emulsion microdroplet or multiple-emulsion microdroplet and/or GUV may be incubated under conditions allowing for reverse transcription followed by conditions allowing for PCR as described herein. The single emulsion microdroplet or multiple-emulsion microdroplet and/or GUV may be incubated on the same microfluidic device as was used to add the RT-PCR reagents, or may be incubated on a separate device. In certain embodiments, incubating the single emulsion microdroplet or multiple-emulsion microdroplet and/or GUV under conditions allowing for RT-PCR is performed on the same microfluidic device used to encapsulate and lyse cells.

In certain embodiments, the reagents added to the single emulsion microdroplet or multiple-emulsion microdroplet and/or GUV for RT-PCR or PCR further includes a fluorescent DNA probe capable of detecting RT-PCR or PCR products. Any suitable fluorescent DNA probe can be used including, but not limited to SYBR Green, TaqMan®, Molecular Beacons and Scorpion probes. In certain embodiments, the reagents added to the single emulsion microdroplets or multiple-emulsion microdroplet and/or GUV include more than one DNA probe, e.g., two fluorescent DNA probes, three fluorescent DNA probes, or four fluorescent DNA probes. The use of multiple fluorescent DNA probes allows for the concurrent measurement of RT-PCR or PCR products in a single reaction.

Double PCR

To amplify rare transcripts, a multiple-emulsion microdroplet and/or GUV that has undergone a first-step RT-PCR or PCR reaction as described herein may be further subjected to a second step PCR reaction. In some embodiments, a first multiple-emulsion microdroplet and/or GUV that has undergone a first-step RT-PCR or PCR reaction is encapsulated in a second multiple-emulsion microdroplet and/or GUV containing additional PCR reagents, including, but not limited to enzymes (e.g. DNA polymerase), DNA probes (e.g. fluorescent DNA probes) and primers, followed by rupture of the first multiple-emulsion microdroplet and/or GUV. In certain embodiments, the second multiple-emulsion microdroplet and/or GUV containing the additional PCR reagents is larger than the microdroplet that has undergone the first step RT-PCR or PCR reaction. This may be beneficial, for example, because it allows for the dilution of cellular components that may be inhibitory to the second step PCR. The second step PCR reaction may be carried out on the same microfluidic device used to carry out the first-step reaction or on a different microfluidic device. The above method may also be performed using single emulsion microdroplets in place of multiple-emulsion microdroplets.

In some embodiments, the primers used in the second step PCR reaction are the same primers used in the first step RT-PCR or PCR reaction. In other embodiments, the primers used in the second step PCR reaction are different than the primers used in the first step reaction.

Digital PCR

The methods and devices described herein can be used to quantitate nucleic acids using, for example, digital PCR. In digital PCR, target nucleic acids from a solution are diluted such that, when the sample is isolated in compartments, most compartments encapsulate either zero or one target molecule, although higher loading rates can often be used, provided they can be modeled. Reagents sufficient for amplification of the target nucleic acids are also included in the compartments, and the compartments subjected to conditions suitable for amplification. The compartments can have a variety of structures, including fabricated microwells in a substrate or single emulsion droplets. They may also be formed as, for example, the multiple-emulsion microdroplets, e.g., double emulsions, and/or GUVs of the present disclosure. In some such embodiments, the sample is compartmentalized in double emulsions and the double emulsions subjected to amplification. Droplets that contain a target undergo amplification, while those that do not, do not and therefore do not yield nucleic acid amplification products. If a detection component is included, double emulsions that comprise the target may fill with a detectable signal, allowing them to be identified by, for example, imaging or flow dropometry. A powerful advantage of using double emulsions to perform such digital PCR is that the double emulsions can be suspended in an aqueous carrier phase that is miscible with the partitioned sample, and can therefore readily be detected and/or sorted using commercially available flow cytometers and fluorescence activated cell sorters (FACS).

As described herein, this allows for enrichments of target entities out of a sample that is not possible with other methods in which sorting is not easily accomplished. The disclosed methods can be used to quantitate nucleic acids in solution by counting the fraction of double emulsions that are fluorescent and underwent amplification and thus contained at least a single target nucleic acid, in most instances; false amplification may occur for stochastic reasons or, for example, the encapsulation of dust or other contaminants that interfere with the specificity of the amplification reaction. TaqMan® probes, molecular beacons, SYBR, and other kinds of detection components can also be included, allowing the use of multiple optical spectra for simultaneously detecting the amplification of different nucleic acid sequences in the target or due to multiple targets being encapsulated in the same double emulsions, which may be advantageous in some instances.

Measuring Lengths of Nucleic Acids

The methods and devices described herein can be used to measure the length distributions of nucleic acids in solution.

This may be accomplished by designing probe sequences that anneal to the target nucleic acids at different regions of known distance along their lengths. The probes can then be mixed with the target nucleic acids and compartmentalized in multiple-emulsion microdroplets, e.g., double emulsions, and/or GUVs. Each multiple-emulsion microdroplet and/or GUV may contain, for example, two primer and probe sets that signal the presence of two different regions on the target a known distance apart. This can be repeated for different combinations of probes such that different pairs probe different distances and different regions of the target. The samples can be subjected to amplification, analysis, and sorting, if desired. In the analysis, one will find that some multiple-emulsion microdroplets and/or GUVs undergo amplification only with one of the probes while others, for example, amplify with only the other probe. This suggests that in these multiple-emulsion microdroplets and/or GUVs, one type contains the region just for one of the probes, while the other type contains the region of the other probe. In this population, may also be multiple-emulsion microdroplets and/or GUVs that undergo amplification with both probes, indicating that the target nucleic acid therein contained both regions. In this same suspension will be a large number of multiple-emulsion microdroplets and/or GUVs comprising a measurable fraction of each of the three types of droplets—in addition to ones that, of course, undergo no amplification and, thus, presumably, do not contain the targeted regions. This data can be used to infer the lengths of the nucleic acids in solution.

For example, if the nucleic acids in solution are largely intact as whole molecules, than the majority of droplets undergoing amplification will exhibit amplification with both probe and primer sets and will thus show mixed signal. By contrast, if the nucleic acid targets are highly fragmented, most of the detection events will be one or the other probe, with only rare instances of both probes. Since the distances between the probes may be known, this allows one to estimate the lengths and fragmentation of the molecules in the solution. This process can be repeated with different probe sets targeting different regions and/or having different distances between them, to more fully characterize the fragmentation of the target nucleic acids. The above method may also be performed using single emulsion microdroplets in place of multiple-emulsion microdroplets.

MESA in Multiple-Emulsion Microdroplets and/or GUVs

The methods described herein can be used to perform microfluidic enrichment for sequence analysis (MESA) of target nucleic acids. This is accomplished by using the method to encapsulate target nucleic acids in multiple-emulsion microdroplets and/or GUVs and perform amplification in those droplets, yielding fluorescent signals when the droplets contain a target sequence. These droplets can then be sorted, thereby enriching the nucleic acids in the sorted pool. The reaction may also be multiplexed, if desired, to differentiate between molecules that contain multiple, distinct subsequences. Amplification may also be used to amplify the sorted nucleic acids either prior to, simultaneous with, or post sorting, so as to enable sequencing.

A key advantage of this approach is that the region that is amplified in the multiple-emulsion microdroplets and/or GUVs can be used simply as a "detection region"—the amplicons need not comprise the molecules that are subjected to sequencing. Instead, they signal when a target molecule is present in a multiple-emulsion microdroplet and/or GUV so that the whole molecule can be recovered for downstream analysis. This is powerful because it allows a large nucleic acid, even one that is far too large to be efficiently amplified, to be recovered for downstream analysis. For example, suppose that there exists a gene that is thought to be part of an important biological pathway, e.g., signaling cascade, in a microorganism that is as yet still undiscovered. The goal is to recover the genes encoding the proteins involved in this pathway so that they can be sequenced and studied. This cannot easily be accomplished using existing enrichment methods since the microbe, being unknown may not be specifically cultivable and, in addition, the pathway, being largely of unknown sequence, cannot be purified using hybridization probes, since sequences for the probes to hybridize to are not known aside from the individual gene, which may be too small to pull out the entire pathway. However, this can be accomplished using the MESA method described herein.

In some embodiments, the nucleic acids from the target may be fragmented to a size large enough to encapsulate the entire pathway, such as, for example tens or hundreds of kilobases, or even megabases or longer fragments. If the pathway exists within a fragment, it may contain the known gene. The fragmented nucleic acids, most of which do not contain the target, are subjected to the techniques described herein resulting in multiple-emulsion microdroplets, e.g., double emulsions, and/or GUVs that, for the most part, do not contain a pathway and thus exhibit no amplification, while rare drops do contain the pathway and undergo amplification. The positive droplets can then be recovered by, for example, FACS sorting double emulsions that are fluorescently bright. These can then be subjected to further manipulations such as, if necessary, specific and non-specific amplification, quantitation through digital or quantitative PCR, and DNA sequencing. A powerful advantage of MESA over other enrichment strategies is that it allows very large nucleic acids, even up to the size of an entire genome, to be detected and recovered based on a short, known sequence of only tens of hundreds of base pairs. Few other enrichment methodologies have the ability to enrich such large nucleic acid sequences out of a heterogeneous pool using such limited amounts of information about the sequence.

The method can also be used to identify the DNA sequences of individual genomes. In this embodiment, nucleic acids from a target can be fragmented and encapsulated in multiple-emulsion microdroplets, e.g., double emulsions, and/or GUVs, with PCR reagents and primers specific to the DNA sequence of interest. After amplification, the positive multiple-emulsion microdroplets and/or GUVs can be sorted into individual compartments, such as well plate arrays, using FACS. Individual compartments can then be subjected to further manipulation, such as either specific or non-specific amplification. The resulting amplicons can then be used to make libraries for next generation sequencing techniques, or as material used directly in Sanger sequencing. This technique would be useful, for example, in a method designed to identify genetic differences in a retroviral population, such as HIV, found in an individual patient.

As discussed above, methods described herein can be used for digital PCR and, related, microfluidic enrichment for sequencing analysis (MESA). In some embodiments, a sample comprising nucleic acids, viruses, cells, particles, etc., is partitioned in double emulsions using microfluidic double emulsification. The double emulsion droplets are collected into a reservoir, such as a PCR tube, and incubated under conditions suitable for amplification such as thermal cycling. Isothermal methods can also be used, such as MDA, MALBAC, LAMP, etc. A fluorescent reporter can be included in the droplets or added to the carrier phase to induce a difference in fluorescence between droplets containing the target nucleic acids and droplets which do not contain the target nucleic acids.

For example Sybr green can be added to the carrier phase such that it partitions into the double emulsion. Since Sybr becomes much more fluorescent in the presence of double stranded DNA, droplets that undergo amplification will be fluorescently brighter than those that do not. To quantitate the number of target molecules in the sample, the droplets can be subjected to flow cytometric analysis, or even fluorescence activated cell sorting (FACS), FIG. 14.

Figure 14:
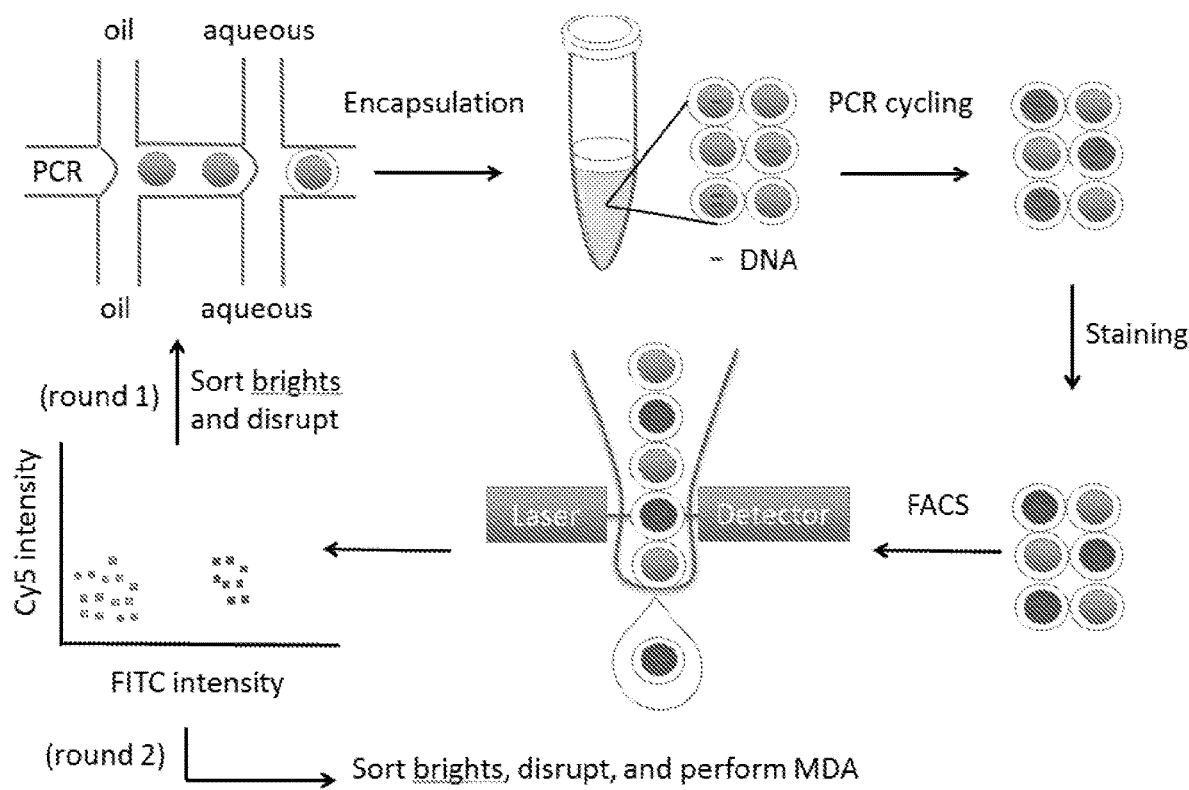
FIG. 14. provides a schematic of double emulsion digital PCR and MESA workflow. A sample comprising nucleic acids or cells is partitioned into double emulsions using two-step (shown) or one-step (not shown) double emulsification. The double emulsions are collected in a tube and thermocycled, resulting in, in the case of single target molecule encapsulation, digital amplification in double emulsions containing targets. The double emulsions are then subjected to FACS analysis and sorting.

As the droplets flow through the flow cytometer, information about their size and fluorescence can be recorded. In the instance that the target molecules are loaded at limiting dilution, some droplets will be detected as fluorescent, because they contained a target molecule, and others will be detected as dim, because they do not, as shown in FIG. 14, lower left. The fraction of bright-to-dim droplets can be used, in accordance with a Poisson distribution to estimate the starting concentration of the target molecule in the original sample. By using a FACS to sort the droplets based on fluorescence, it is possible to recover the double emulsions that contain target molecules and, by breaking the double emulsions, to retrieve the target molecules. This can be used to screen large, heterogeneous populations of nucleic acids to selectively recover target sequences. The above method may also be performed using single emulsion microdroplets, where suitable, in place of multiple-emulsion microdroplets.

PCR Activated Cell Sorting (PACS) in Multiple-Emulsion Microdroplets and/or GUVs The MESA technology enables the enrichment of naked nucleic acids out of a solution, but a similar approach can be applied to nucleic acids contained within entities, such as within cells, viruses, spores, particles etc., wherein the process is largely the same. For example, the entities comprising the target nucleic acids can be encapsulated in multiple-emulsion microdroplets, e.g., double emulsions, and/or GUVs, and subjected to conditions sufficient to amplify the target nucleic acids, as described above. The multiple-emulsion microdroplets and/or GUVs can then be sorted based on amplification, to recover entities that have the target.

An important consideration when applying this technique to entities, especially ones that have a membrane or protective shell, is that the nucleic acids must be accessible to amplification for specific detection to occur, which may necessitate specialized procedures. For example the entities can be encapsulated in the multiple-emulsion microdroplets and/or GUVs with agents that release nucleic acids, such as proteases, lysozyme, detergents, strong bases, etc. They may also be encapsulated in multiple-emulsion microdroplets and/or GUVs and then soaked in solution that contain the lysing agent, which may partition through the multiple-emulsion microdroplets and/or GUVs shell to induce lysis. They may also be encapsulated for example in gel particles that can be soaked in lysing agent. Then, these gel particles which will contain the nucleic acids of the entities, can be encapsulated in the multiple-emulsion microdroplets and/or GUVs for the detection via amplification procedure. The gel can be selected such that, it does not inhibit the lysis or amplification reaction such as, for example, by ensuring that its pore size is sufficiently large so as to enable reagent to diffuse through the gel while trapping nucleic acids, or by enabling it to melt upon heating of the multiple-emulsion microdroplets and/or GUVs, as when using agarose. The gel may also be functionalized, if desired, to attach desired cell compounds, such as RNA molecules that may otherwise leak out of the gels and be undetectable. Yet another procedure that can be implemented to enable access of amplification reagents to target nucleic acids is to use electric current to lyse cells, viruses, particles, etc., as they are being encapsulated into the multiple-emulsion microdroplets and/or GUVs. This can be achieved, for instance, by flowing the cells through a channel in which an electric current flows, which can create pores in a cell membrane, for example, and facilitate cell lysis. The above method may also be performed using single emulsion microdroplets, where suitable, in place of multiple-emulsion microdroplets.

Live-Cell PCR Activated Cell Sorting (PACS)

The application of multiple emulsion, e.g., double emulsion, PCR and sorting to cells described so far has included the lysis and, in most instances, death of the organism. However, by modifying the approach and using the methods described herein, it is also possible to recover live, intact cells. This can be accomplished by, for example, encapsulating living cells in multiple-emulsion microdroplets and/or GUVs under conditions such that cell contents leak into the encapsulating multiple-emulsion microdroplet and/or GUV while maintaining the viability of the cell. This is possible by, for instance, flowing the cell through a channel in which an electric current also flows, which can induce pore formation in the cell membrane and allow cell lysate to leak out. When the cell passes out of this channel, its membrane may seal back up, while the lysate that leaked out still exists around the cell. For laminar flow conditions, this can be performed such that the lysate around the cell flows with the cell and is encapsulated in the same compartment, such as a multiple-emulsion microdroplet and/or GUV. Reagents suitable for amplification of the cell nucleic acids or detection of other cellular components can also be included such that the lysate around the cell can interact with the reagents when in the droplet. The reaction can be designed such that a fluorescent signal is produced, enabling droplets that contain the target cell to be recovered via sorting, and allowing live recovery of the cells. This is a powerful use of the technology because it provides the benefits of PACS—the ability to differentiate between cells based on sequence biomarkers, such as molecules and RNA—while preserving cell life so that other reactions and analyses can be performed. The above method may also be performed using single emulsion microdroplets, where suitable, in place of multiple-emulsion microdroplets.

Mass Spectrometry Activated Cell Sorting (MS-ACS)

The methods described herein rely, in some embodiments, on the ability to compartmentalize reactions in multiple-emulsion microdroplets, e.g., double emulsions, and/or GUVs, detect reaction products within the multiple-emulsion microdroplets and/or GUVs, and sort the multiple-emulsion microdroplets and/or GUVs to recover specific entities based on those products and perform suitable analyses. Many types of assays can be performed, such as enzymatic assays, e.g., PCR, to differentiate between different entities, such as cells and viruses. However, in some cases, enzymatic techniques may not be able to detect the analyte of interest. In these instances, other methods can be implemented, such as spectrographic methods. A very powerful detection method is mass spectrometry, because it is sensitive and general. However, a limitation of mass spectrometry is that it is a destructive technology, destroying the sample that it analyzes. If the goal is the recovery of information only, this may be acceptable, but in some instances it is desirable to additionally recover material from the system which, normally, would be destroyed by the mass spectrometer.

Using the methods described herein, mass spectrometry can be used to analyze a sample while still allowing recovery of the sample. For example, suppose that the objective is to identify cells expressing proteins involved in a pathway. The cells can be loaded into multiple-emulsion microdroplets, e.g., double emulsions, and/or GUVs and cultured, so that there are many in each multiple-emulsion microdroplet and/or GUV, and/or so that they are allowed to produce the products of the pathways, e.g., molecules, compounds, etc., which will fill the multiple-emulsion microdroplet and/or GUV. The multiple-emulsion microdroplets and/or GUVs can then be flowed into a device that will split off a portion of the multiple-emulsion microdroplets and/or GUVs, capturing some of the material from the cells or cell secretions, which can be subjected to destructive mass spectrometry. The other portion can then be sorted. The mass spectrometer can be used to analyze the compounds in the sampled portion and this information can be used to determine how to sort the sister portion of the droplet. Using this method, it is possible to use very sensitive and general mass spectrometry to specifically sort cells, while allowing recover of whole cells or cell lysates. The above method may also be performed using single emulsion microdroplets, where suitable, in place of multiple-emulsion microdroplets.

Colony Growth and Lysis

The ability to encapsulate cells in multiple-emulsion microdroplets, e.g., double emulsions, and/or GUVs, is valuable for culturing organisms, such as cells and viruses. For example, if cells are grown in a single, shared volume, competition between cells may result in certain cells taking over the population, such that they comprise the majority of cells after some culture time. By compartmentalizing the cells in multiple-emulsion microdroplets and/or GUVs and culturing them, competition can be controlled and/or mitigated. Moreover, the permeability of the multiple-emulsion microdroplets and/or GUVs can be set such that certain molecules are able to pass through while others are not. This allows, for example, signaling molecules or other molecules important for growth to pass freely through the multiple-emulsion microdroplet and/or GUV shells, to better control culture conditions. The above method may also be performed using single emulsion microdroplets, where suitable, in place of multiple-emulsion microdroplets.

Digital ELISA

In some embodiments, the disclosed methods and devices can be used to quantitate epitopes in a sample using a digital ELISA procedure. In some embodiments, for example, epitopes bound to a solid substrate, such as a planer substrate surface or the surfaces of beads, can be additionally bound with an affinity reagent labeled with an enzyme catalyst. The sample can be washed to remove unbound affinity reagent and enzyme. The labeled epitopes or a portion thereof can then be released in solution in a variety of ways. For ease, the enzyme catalyst may be bound to the affinity reagent through a bond that can be degraded chemically or with the application, for example, of heat or light. Alternatively, the interaction between the affinity reagent and the epitope can be broken, or the interaction between the epitope and the substrate can be broken. If the binding occurs on beads, then the beads can be suspended in solution after the washing step, thereby suspending the enzyme catalysts. The suspended enzyme catalysts can then be encapsulated in multiple-emulsion microdroplets, e.g., double emulsions, and/or GUVs, with reagents sufficient to detect the enzyme catalyst, such as a substrate that the enzyme catalyst can convert into a fluorescent product. The multiple-emulsion microdroplets and/or GUVs can then be incubated under conditions suitable for catalysis, resulting in multiple-emulsion microdroplets and/or GUVs containing a large amount of reaction product when the catalyst is present and a low amount when it is not. The number of fluorescent multiple-emulsion microdroplets and/or GUVs can then be quantitated compared to the dim multiple-emulsion microdroplets and/or GUVs, providing a measure of the number of catalyst molecules present in the sample. This information can then be used to infer the concentration of epitopes in the original sample.

Using the multiplexing methods described herein, this can also be accomplished without the need to wash the sample after binding. For example, two antibodies detecting the same target can be introduced into the sample, each labeled with a different catalyst. The sample can then be encapsulated in multiple-emulsion microdroplets, e.g., double emulsions, and/or GUVs. In the event that a target is present, it should be bound, in many instances, by both antibodies, as occurs in a typical "sandwich" ELISA, except in this case the molecules are free to diffuse in solution rather than being bound to a substrate. The results will be, as in the previous examples, multiple-emulsion microdroplets and/or GUVs that, sometimes, contain just one of the antibodies or that contain both antibodies, which can be detected by monitoring the presence of the catalyst reactions in the droplets. Provided the dilutions are properly controlled so that most droplets are empty, it should be possible to ascribe the presence of both catalyst products to a target being present in the droplet, while the presence of just one of the catalyst products likely corresponds to an unbound antibody. By quantitating the fraction of double-positive droplets, it is possible to estimate the fraction of targets in solution without having to perform washing procedures. The above method may also be performed using single emulsion microdroplets, where suitable, in place of multiple-emulsion microdroplets.

Multiplexing

In certain embodiments of the subject methods, multiple biomarkers may be detected and analyzed for a particular cell. Biomarkers detected may include, but are not limited to, one or more proteins, transcripts and/or genetic signatures in the cell's genome or combinations thereof. With standard fluorescence based detection, the number of biomarkers that can be simultaneously interrogated may be limited to the number of fluorescent dyes that can be independently visualized within each a multiple-emulsion microdroplet and/or GUV. In certain embodiments, the number of biomarkers that can be individually detected within a particular a multiple-emulsion microdroplet and/or GUV can be increased. For example, this may be accomplished by segregation of dyes to different parts of a multiple-emulsion microdroplet and/or GUV. In particular embodiments, beads (e.g. LUMINEX® beads) conjugated with dyes and probes (e.g., nucleic acid or antibody probes) may be encapsulated in a multiple-emulsion microdroplet and/or GUV to increase the number of biomarkers analyzed. In another embodiment, fluorescence polarization may be used to achieve a greater number of detectable signals for different biomarkers for a single cell. For example, fluorescent dyes may be attached to various probes and a multiple-emulsion microdroplet and/or GUV may be visualized under different polarization conditions. In this way, the same colored dye can be utilized to provide a signal for different probe targets for a single cell. The use of fixed and/or permeabilized cells (as discussed in greater detail below) also allows for increased levels of multiplexing. For example, labeled antibodies may be used to target protein targets localized to cellular components while labeled PCR and/or RT-PCR products are free within a multiple-emulsion microdroplet and/or GUV. This allows for dyes of the same color to be used for antibodies and for amplicons produced by RT-PCR. The above method may also be performed using single emulsion microdroplets, where suitable, in place of multiple-emulsion microdroplets.

Microdroplets, Including Multiple-Emulsion Microdroplets, and Generation Thereof In practicing the methods of the present disclosure, the composition and nature of the microdroplets, e.g., multiple-emulsion microdroplets, may vary. For instance, in certain aspects, a surfactant may be used to stabilize the microdroplets. Accordingly, a microdroplet may involve a surfactant stabilized emulsion, e.g., a surfactant stabilized single emulsion or a surfactant stabilized double emulsion. Any convenient surfactant that allows for the desired reactions to be performed in the microdroplets may be used. In other aspects, a microdroplet is not stabilized by surfactants or particles.

The surfactant used depends on a number of factors such as the oil and aqueous phases (or other suitable immiscible phases, e.g., any suitable hydrophobic and hydrophilic phases) used for the emulsions. For example, when using aqueous droplets in a fluorocarbon oil, the surfactant may have a hydrophilic block (PEG-PPO) and a hydrophobic fluorinated block (Krytox® FSH). If, however, the oil was switched to be a hydrocarbon oil, for example, the surfactant would instead be chosen so that it had a hydrophobic hydrocarbon block, like the surfactant ABIL EM90. In selecting a surfactant, desirable properties that may be considered in choosing the surfactant may include one or more of the following: (1) the surfactant has low viscosity; (2) the surfactant is immiscible with the polymer used to construct the device, and thus it doesn't swell the device; (3) biocompatibility; (4) the assay reagents are not soluble in the surfactant; (5) the surfactant exhibits favorable gas solubility, in that it allows gases to come in and out; (6) the surfactant has a boiling point higher than the temperature used for MDA and PCR (e.g., 95° C.); (7) the emulsion stability; (8) that the surfactant stabilizes drops of the desired size; (9) that the surfactant is soluble in the carrier phase and not in the droplet phase; (10) that the surfactant has limited fluorescence properties; and (11) that the surfactant remains soluble in the carrier phase over a range of temperatures.

Other surfactants can also be envisioned, including ionic surfactants. Other additives can also be included in the oil to stabilize the microdroplets, including polymers that increase droplet stability at temperatures above 35° C.

The microdroplets described herein may be prepared as emulsions, e.g., as an aqueous phase fluid dispersed in an immiscible phase carrier fluid (e.g., a fluorocarbon oil or a hydrocarbon oil) or vice versa. In particular, multiple-emulsion microdroplets of the present disclosure may be provided as double-emulsions, e.g., as an aqueous phase fluid in an immiscible phase fluid, dispersed in an aqueous phase carrier fluid; quadruple emulsions, e.g., an aqueous phase fluid in an immiscible phase fluid, in an aqueous phase fluid, in an immiscible phase fluid, dispersed in an aqueous phase carrier fluid; and so on. The nature of the microfluidic channel (or a coating thereon), e.g., hydrophilic or hydrophobic, may be selected so as to be compatible with the type of emulsion being utilized at a particular point in a microfluidic work flow. For example, a hydrophilic channel may be utilized in connection with a double emulsion stage whereas a hydrophobic channel may be utilized in single emulsion stage.

Single emulsions may be generated using microfluidic devices as described in greater detail below. Microfluidic devices can form emulsions consisting of droplets that are extremely uniform in size. The microdroplet generation process may be accomplished by pumping two immiscible fluids, such as oil and water, into a junction. The junction shape, fluid properties (viscosity, interfacial tension, etc.), and flow rates influence the properties of the microdroplets generated but, for a relatively wide range of properties, microdroplets of controlled, uniform size can be generated using methods like T-junctions and flow focusing. To vary microdroplet size, the flow rates of the immiscible liquids may be varied since, for T-junction and flow focus methodologies over a certain range of properties, microdroplet size depends on total flow rate and the ratio of the two fluid flow rates. To generate an emulsion with microfluidic methods, the two fluids are normally loaded into two inlet reservoirs (syringes, pressure tubes) and then pressurized as needed to generate the desired flow rates (using syringe pumps, pressure regulators, gravity, etc.). This pumps the fluids through the device at the desired flow rates, thus generating microdroplet of the desired size and rate.

Double emulsions may be generated using microfluidic devices as described in greater detail below. A double emulsion includes droplets contained within droplets. A particularly useful kind of double emulsion includes an aqueous droplet encapsulated within a slightly larger oil droplet, itself dispersed in a carrier aqueous phase. Double emulsions are valuable because the inner "core" of the structure can be used to contain active compounds, like dissolved solutes or biological materials, where they are shielded from the external environment by the surrounding oil shell. Double emulsions can be generated using a number of microfluidic techniques, including ones that generate them in two-step and one-step processes. The benefit of microfluidic generation of double emulsions is the same as microfluidic generation of single emulsions, which is that the double emulsion dimensions (inner and outer droplet sizes) can be controlled over a wide range and the microdroplets can be formed with a high degree of uniformity.

Generating double emulsions in microfluidics is more difficult than generating single emulsions because, at the relevant length scale (10-100 μm) interfacial and wetting properties dominate over inertial properties. Accordingly, the fluid utilized for the encapsulating phase depends on the wetting properties of the channels. For example, if the channels are hydrophilic, then the aqueous phase will tend to wet the channel walls and displace the oil, thereby encapsulating the oil phase and generating an oil-in-water emulsion. If, on the other hand, the channels are hydrophobic, the water will avoid the walls and be encapsulated by the oil, generating a water-in-oil emulsion. Overcoming this natural proclivity of the device to form a specific emulsion polarity based on its wetting can be challenging. Generating a water-in-oil-in-water emulsion can be accomplished using devices that either have two wetting regions (hydrophobic in one region to form water-in-oil droplets and hydrophilic in another to generate oil-in-water droplets) or are designed to overcome the natural wetting properties of the device in at least one of the regions.

Double emulsions may be formed with the use of spatially-pattered wetting. To generate double emulsions using wetting-controlled droplet formation, a device with spatially patterned wetting is utilized, or two devices with different wetting are utilized sequentially. This is because, for W/O/W double emulsions, a W/O emulsion is generally generated first, and then the emulsion encapsulated into an O/W emulsion. To accomplish this, a first flow focus droplet generator can be functionalized to have hydrophobic wetting so that, when water and oil are introduced, W/O droplets will naturally be generated. This device can then empty into a second flow focus device functionalized to be hydrophilic, and in which a second aqueous phase can be introduced. This will encapsulate the oil phase encapsulating the inner aqueous droplets in the second aqueous phase, generating oil droplets encapsulating the first aqueous droplets, which are double emulsions. To form the inverse polarity, O/W/O double emulsions, the first flow focus device would be functionalized to be hydrophilic (to form O/W) and the second hydrophobic (to form W/O). Higher order multiple emulsions, such as triple and quadruple emulsions, can also be generated by adding additional droplet generators with alternating wetting. Different droplet generation geometries, like T-junctions, can also be used.

Double emulsions may be formed with coaxial flow focusing. Wetting-based double emulsification is robust and effective for forming multiple emulsions of many different compositions, but a drawback to it is that spatially-patterning wettability requires additional fabrication steps that can be challenging and with reduced reproducibility. Methods for forming double emulsions in devices with uniform wettability are thus valuable, because they simplify fabrication. One method for accomplishing this is to utilize a three-dimensional coaxial flow-focusing geometry that shears wetting phases from the channel walls so that they are encapsulated, even if it is their natural tendency to be the encapsulating phase. For example, this can be accomplished by injecting a wetting phase into a junction through a small opening and, simultaneously, injecting a carrier phase that would not normally encapsulate the first phase because of the wettability such that it surrounds the first phase and encapsulates it. Hence, in contrast to wetting-based droplet generation, in which the encapsulating phase is determined by the wettability of the channels, in this modality the encapsulating phase is determined by the geometry of the junction and the orientation in which the fluids are injected.

A two-step double emulsification with geometrical control method may be utilized to form double emulsions. In geometrically-controlled two step double emulsification, a first droplet generation junction is used, via its wetting (e.g., hydrophobic) to form a single emulsion (e.g., W/O). This device then empties into a coaxial flow focusing junction in which the wetting phase encapsulating the droplets is itself encapsulated in a third phase (e.g., W) using the geometrical control effect, generating double emulsions (e.g., W/O/W).

Encapsulation of sample materials and/or reagents, e.g., nucleic acids and/or amplification reagents (e.g., PCR amplification reagents), can be achieved via a number of methods, including microfluidic and non-microfluidic methods. In the context of microfluidic methods, there are a number of techniques that can be applied, including glass microcapillary double emulsification or double emulsification using sequential droplet generation in wettability patterned devices. Microcapillary techniques form droplets by generating coaxial jets of the immiscible phases that are induced to break into droplets via coaxial flow focusing through a nozzle. However, a potential disadvantage of this approach is that the devices are generally fabricated from microcapillary tubes that are aligned and glued together. Since the drop formation nozzle is on the scale of tens of microns, even small inaccuracies in the alignment of the capillaries can lead to a device failure. By contrast, sequential drop formation in spatially patterned droplet generation junctions can be achieved in devices fabricated lithographically, making them simpler to build and to create in large numbers while maintaining uniformity over dimensions. Examples of such devices are described herein. However, in some cases the planar nature of these devices may not be ideal for generating double emulsions, since the separate phases all enter the device while in contact with the channel walls, necessitating that wettability be carefully patterned to enable engulfment of the appropriate phases at the appropriate locations. This may make the devices more difficult to fabricate, and in some cases, may prevent emulsification of liquids whose wetting properties are not optimized for the device. Accordingly, in some embodiments, the present disclosure provides methods and related devices that combine the best attributes of the capillary and lithographically fabricated devices.

For example, in some embodiments a simultaneous double emulsification with geometrical control method may be utilized. Such a method may be referred to herein as an "M-junction double emulsification" method. This methodology is similar to the two-step geometrical control method, except that there is only one junction into which all three phases are introduced and the inner and outer droplets form at approximately or exactly the same time. In this method, the inner phase (e.g., W) is injected into the geometrically-controlled droplet generator through a small channel and the second phase (e.g., O) is injected via two other channels flanking it that are either the same height or taller than the first channel. Because the channel walls prefer the second phase (hydrophobic), this will cause the inner phase to be surrounded by and encapsulated in the second phase, although it need not yet have broken to form a droplet. The third phase (e.g., W) is also simultaneously introduced into the junction so that, via geometrical control, it encapsulates the second phase. This produces a double-jet structure, in which the first phase (e.g., W) is encapsulated in the second phase (e.g., O), which is itself encapsulated in the third phase (e.g., W). The double jet can then be broken into double emulsions via several methods, including co-flow droplet generation and coaxial flow-focusing. Flow rates, channel dimensions, wettability, and fluid properties can all be adjusted to control the encapsulations of the phases and adjust double emulsion droplet size.

In some embodiments, a device including five input channels which join at a junction can be fabricated using lithographic methods. The device is designed so that the inner channel between the two flanking (middle) channels is of a shorter height than the channels on either side. In addition, the inner and two middle channels join two outer channels at the junction that are taller than each of the inner and two middle channels and, from which, the carrier fluid for the double emulsion is introduced. The three phases to be formed into double emulsions are then introduced into the device such that the inner encapsulated phase is introduced from the central, shortest inlet, and the middle shell fluid is introduced from the two flanking (middle) channels. The carrier fluid is introduced from the two outer channels at the junction in which all channels are joined. Due to the geometry of the channels, the inner fluid will be enveloped within the middle fluid which, itself, will be enveloped within the carrier fluid. This will generate a double jet similar to observed in microcapillary devices. The composition of the double jet can be of any phases that can form double emulsions, such as water/oil/water, oil/oil/water, oil/water/oil, etc. Moreover, the orientation of the fluids and, thus, the structure of the double emulsions does not depend strongly on the intrinsic wetting properties of the fluid against the channel walls but, rather, on the orientation in which they are ordered in the device. The inner fluid will, in general, form the inner droplet of the double emulsion, while the fluid in the flanking side channels will form the shell and the fluid in the outer channel will form the carrier.

In exemplary devices, the middle fluid channels can be of the same height or shorter or taller than the inner fluid channels. In general, it is preferable to have the middle channels be taller than the inner channel, which facilitates envelopment of the inner fluid by the middle fluid in the intersection junction, since the inner fluid is more surrounded by side channels that are taller. After the coaxial get is formed, it can be induced to break into droplets using a variety of methods such as, for example, plugging based droplet generation, coaxial flow forcing through a constriction, or air-bubble triggered droplet generation. In addition, the droplets can be split into portions using geometrical breakup of double emulsions, to make smaller droplets.

Figure 3:
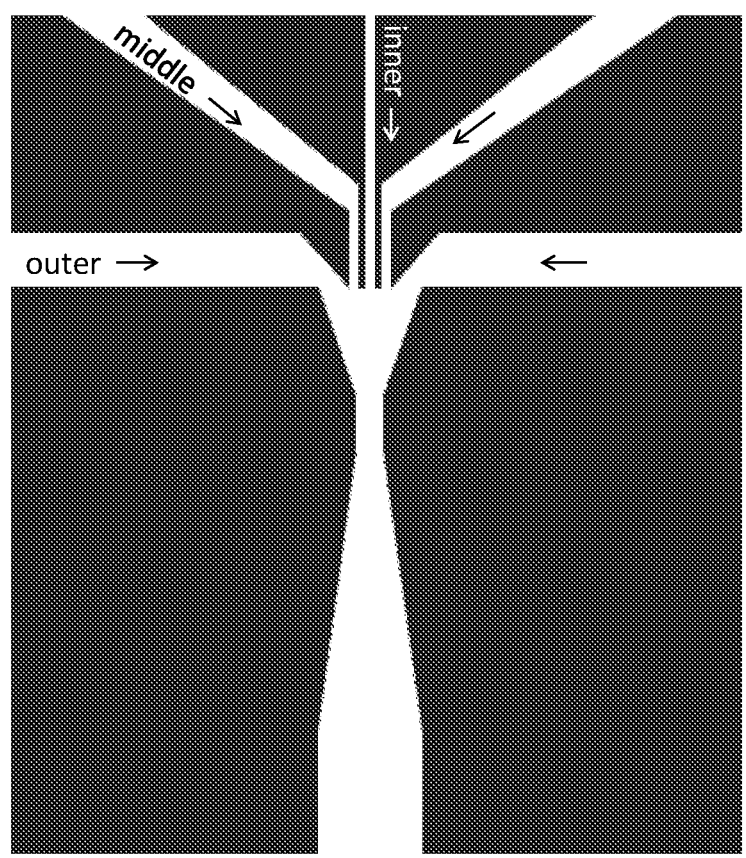
FIG. 3 provides a schematic of an "M-junction" portion of a microfluidic device which can be used to prepare double emulsions in accordance with the present disclosure.
Figure 4:
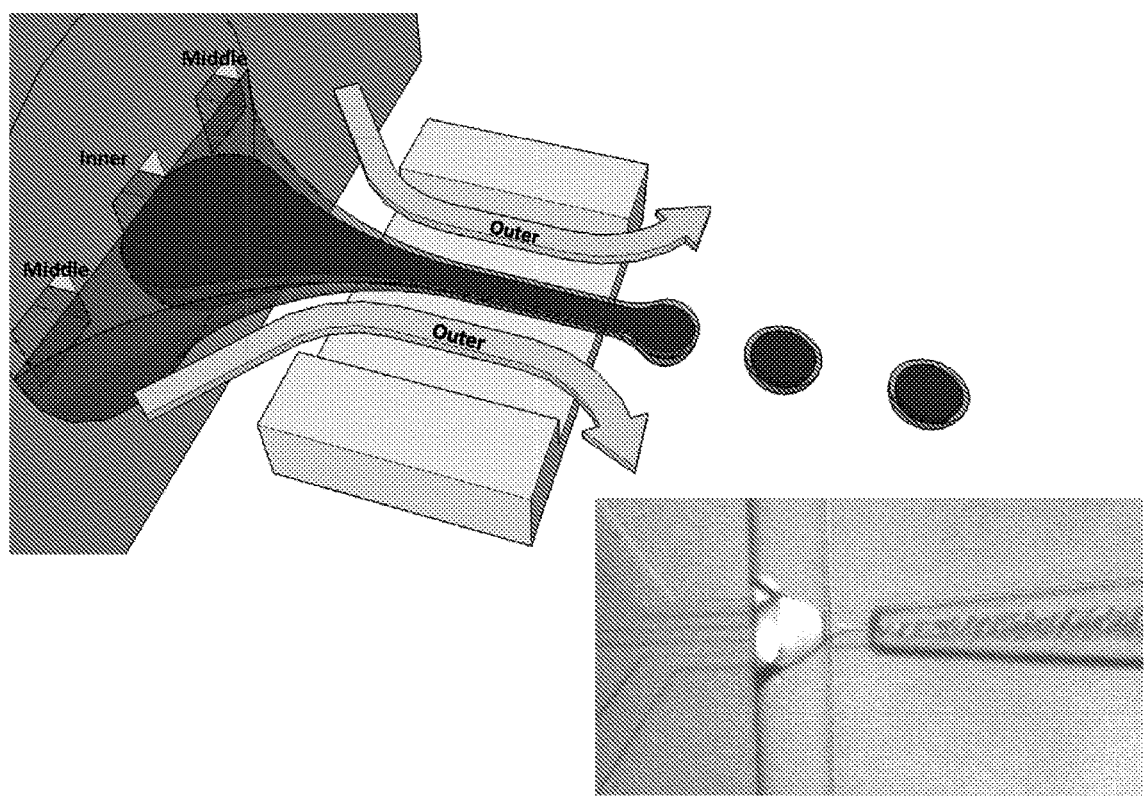
FIG. 4 provides another schematic (top left) of an "M-junction" portion of a microfluidic device which can be used to prepare double emulsions in accordance with the present disclosure.
Figure 5:
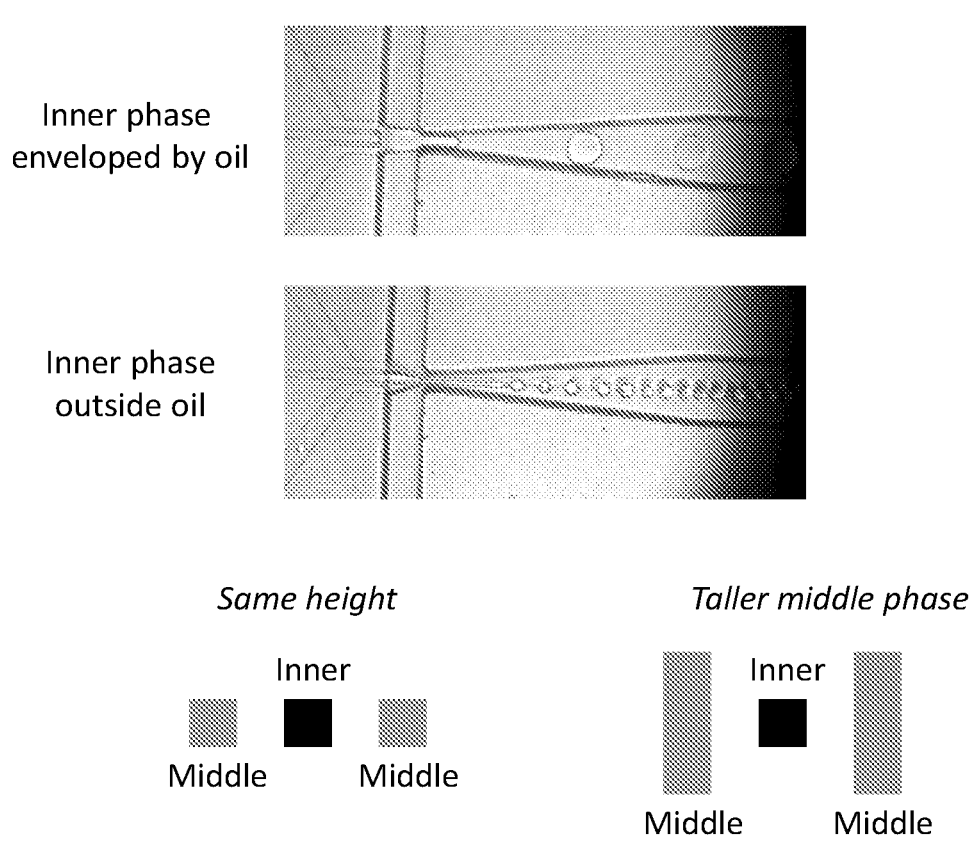
FIG. 5 provides two images of "M junction" portions of microfluidic devices. The top image shows the inner phase enveloped by oil in the formation of a double emulsion for the configuration shown at the bottom right, wherein the two middle channels are taller than the inner channel. The bottom image shows incomplete double emulsion formation, wherein the inner phase is outside the oil, for the configuration shown at the bottom left having inner and middle channels of the same height.
Figure 6:
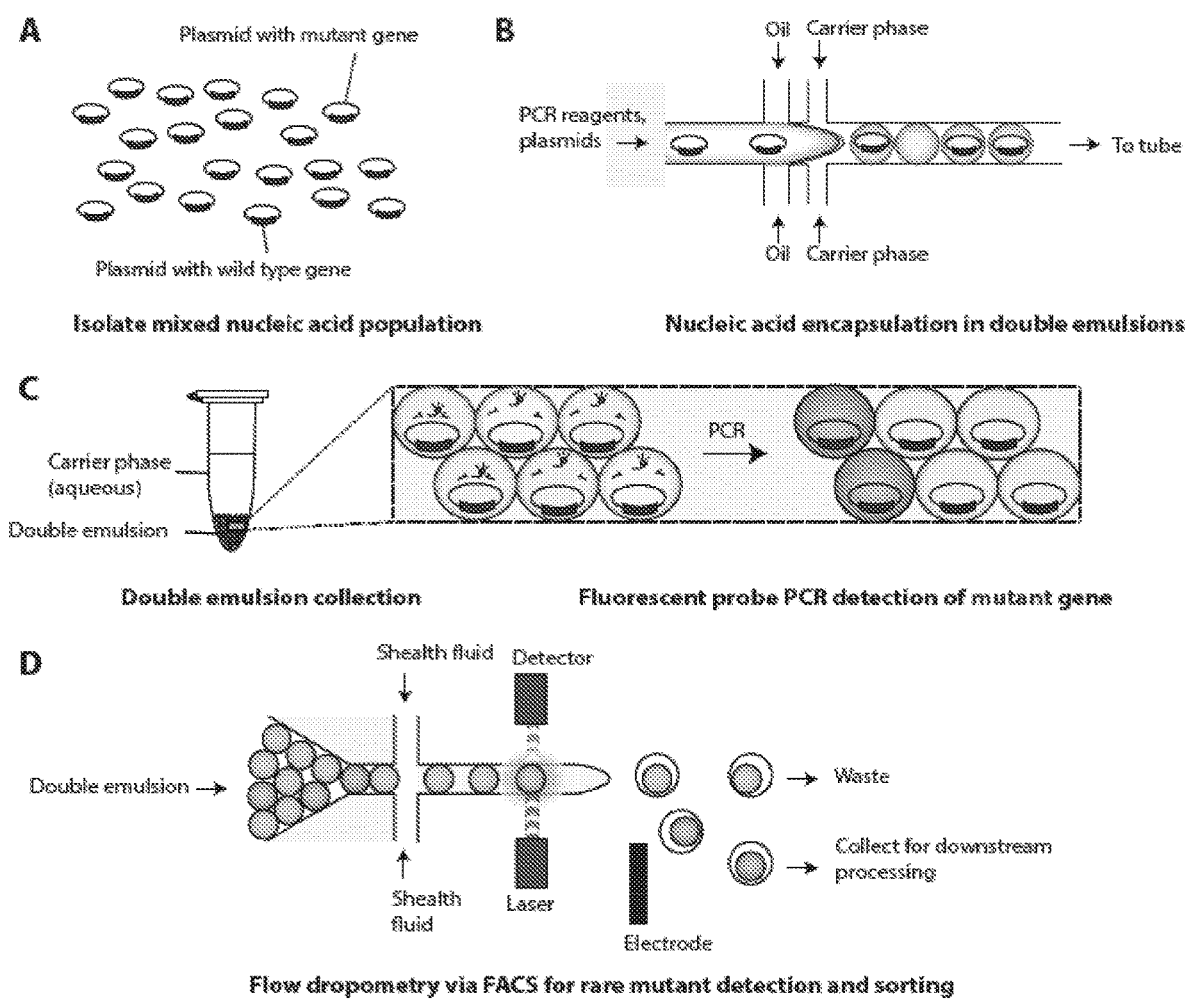
FIG. 6 is a schematic showing an exemplary double emulsion or GUV PCR workflow according to embodiments of the present disclosure. Generally, a mixed population of wild-type and mutant DNA is encapsulated into double emulsions or GUVs and thermalcycled. Double emulsions or GUVs containing the mutant DNA sequence are identified via DNA dyes that fluoresce when bound to the PCR product resulting from amplification of the mutant DNA. Using either one or a few microfluidic devices, nucleic acid molecules (Panel A) are dispersed into double emulsion microdroplets or GUVs together with PCR reagents (Panel B). After thermalcycling in a standard PCR machine, double emulsions or GUVs that contain single templates (or more than one) of interest will undergo amplification, whereas empty double emulsions or GUVs that have none will have no amplification. These double emulsions or GUVs can then be stained with an intercalating DNA dye that can diffuse into the cores of the double emulsions or GUVs and stain the amplicons (Panel C). These double emulsions or GUVs can then be subjected to "flow dropometry" (Panel D), whereby the double emulsions or GUVs are quantified on a flow cytometer. The percentage of bright drops or GUVs in a sample can indicate the absolute number of templates of interest, based on Poisson statistics. These bright drops or GUVs can be sorted using Fluorescence activated cell sorting (FACS) machine for subsequent applications such as sequencing.

Schematics of an "M-junction" portion of a microfluidic device which can be used to generate double emulsions as described herein are provided in FIGS. 3-5. Inner, middle, and outer fluid channels are shown.

After multiple emulsions, e.g., double emulsions, are formed, additional manipulations can be performed on them to modify their properties. For example, in many double emulsion formulations, the shells of the double emulsions are permeable to certain molecules, allowing these molecules to be passively diffused into or out of the double emulsions. This can be used for example, to modulate the environment in the double emulsions. Similarly, the inner droplets of the double emulsions can be shrunk or grown by, for example, allowing a solvent to diffuse into or out of them. For example, by dispersing double emulsions in a buffer comprising a high concentration of salt, aqueous phase fluid can be induced to diffuse out of the double emulsions until the osmolarities on the inner droplet and outside carrier phase are matched, at which point the droplet size will remain constant. This can be used to change the size of the inner droplet or, alternatively to concentrate or dilute reagents contained within the double emulsion by adding or removing excess solvent.

The shells of the double emulsions can also be modified using techniques such as solvent extraction to, for example, in the case of a water-in-oil-in water double emulsion, remove excess hydrophobic phase from the shell. This can induce other changes in double emulsions such as, for example, their transition into lipid vesicles, polymersomes, or colloidosomes via dewetting or other phenomena. Air bubbles may also be introduced into the double emulsions, for example, in the inner droplet or in the middle, encapsulating phase. The ability to expand and compress air can also be exploited, if desired, to, for example, increase or reduce the size of the double emulsion or the thickness of the double emulsion shell, in some embodiments. Air bubbles in the middle phase can, for example, be expanded by reducing the pressure of the system, which will exert forces on the inner droplet that, for instance, can be used to induce a transition into another structure, such as a polymersome or vesicle.

Giant Unilamellar Vesicles (GUVs)

Double emulsions generally refer to emulsions within emulsions—i.e., liquid droplets that are contained within liquid droplets of a second immiscible phase. They can be stabilized by surfactant but, importantly, the middle phase "shell" includes a liquid phase in addition to the optional surfactant. As the volume of the shell is reduced, double emulsions resemble less droplets-within-droplets than vesicle-like structures, with a core fluid encapsulated in a thin membrane of surfactant molecules. Double emulsions can be used to form such "vesicles" by allowing them to undergo a de-wetting transition, in which the middle liquid phase fluid is expunged from the shell but a surfactant layer is maintained, generating a vesicle including the aqueous core with a thin layer of surfactant molecules surrounding it, and a small oil droplet that was originally the shell adhering to it.

The tendency of a double emulsion to de-wet depends on the properties of the different solutions and surfactants, especially the interfacial tensions of the different phases with respect to one another. An aqueous formulation including fluorinated oil, PEG-Krytox® surfactant, Jeffamine® (polyetheramine)-Krytox® surfactant, and pluronic, when added to the carrier phase, appears capable of forming double emulsions and vesicles, both of which are thermostable to above 95° C. Krytox® fluids are fluorinated synthetic oils based on hexfluoropropylene oxide combined with a functional end-group. Other surfactants such as Tween® 20 (Polysorbate 20) and Span® 80 (Sorbitane monooleate) may be utilized with or without thickening agents such as PEG, alginate, glycerol, etc., to induce GUV formation from double emulsions.

Surfactants and Thermostable Double Emulsions and GUVs

Without intending to be bound by any particular theory, it is proposed that the preparation of a thermostable double emulsion and/or GUV relies on the use of a surfactant that is able to form membranes or double emulsion interfaces that can withstand high temperatures, such as those associated with standard PCR reactions. One way to accomplish this may be to use a surfactant with a relatively high molecular weight so that when assembled at the interface of a droplet or in a membrane configuration, the energy required to remove the surfactant from the interface (or break the membrane) is higher than can be provided by kT.

Exemplary surfactants which may be utilized to provide thermostable double emulsions and/or GUVs are the "biocompatible" surfactants that include PEG-PFPE (polyethyleneglycol-perflouropolyether) block copolymers, e.g., PEG-Krytox® (see, e.g., Holtze et al., "Biocompatible surfactants for water-in-fluorocarbon emulsions," *Lab Chip,* 2008, 8, 1632-1639, the disclosure of which is incorporated by reference herein), and surfactants that include ionic Krytox® in the oil phase and Jeffamine® (polyetheramine) in the aqueous phase (see, e.g., DeJournette et al., "Creating Biocompatible Oil-Water Interfaces without Synthesis: Direct Interactions between Primary Amines and Carboxylated Perfluorocarbon Surfactants", *Anal. Chem.* 2013, 85(21):10556-10564, the disclosure of which is incorporated by reference herein). Additional and/or alternative surfactants may be used provided they form stable interfaces. Many suitable surfactants will thus be block copolymer surfactants (like PEG-Krytox®) that have a high molecular weight. These examples include fluorinated molecules and solvents, but it is likely that non-fluorinated molecules can be utilized as well.

Accordingly, in some embodiments, the present disclosure provides thermostable double emulsions, including, e.g., a miscible liquid (e.g., nucleic acids and PCR reagents) encapsulated by an immiscible liquid (e.g., oil and surfactant), which is in turn encapsulated in a second miscible liquid (e.g., 1% Pluronic F-56 and 10% PEG35K). These double emulsions are suitable for use in performing biological reactions, such as PCR, RT-PCR, protein-protein interaction studies, etc.

A consideration when forming emulsions, particularly double emulsions, is making them stable so that they remain double emulsions and do not rupture or coalesce. This is often accomplished using stabilizing agents, such as surfactants. However, in some instances, it may be advantageous to create extremely stable double emulsions. In the methods described herein, this can be accomplished, for example, by using a middle phase (enveloping phase) that can be cross linked, such as a polymer gel phase like polydimethylsiloxane. Alternatively, the surfactants themselves can be made to cross-link with one another by, for example, creating a cross linking group. This group can exist on the hydrophobic tail of the surfactant or, alternatively, on the hydrophilic head. It may crosslink the surfactants to each other or, alternatively, crosslinking may be induced by the addition of a reagent from the aqueous phase, such as a molecule that induces polymerization, covalent bond linkage, etc. Biomolecules like antibodies or biotin-streptavidin can also be used to generate surfactant-surfactant crosslinks.

Crosslinking the interface is another way to render the double emulsion shell thermostable. For example, such crosslinking may be achieved by cross-linking the oil phase or by cross-linking the membrane vesicle. As discussed above, one method for crosslinking the interface uses biomolecules, such as streptavidin. For example, the headgroup of a Krytox® polymer may be biotinylated with multiple biotins. Streptavidin is then added to the aqueous phase thereby crosslinking different Krytox® polymers together and generating a cross-linked shell at the water/oil interface. These shells can then be dispersed into water directly or, if desired, encapsulated as double emulsions.

Types of Microdroplets

In practicing the methods of the present invention, the composition and nature of the microdroplets may vary. For instance, in certain aspects, a surfactant may be used to stabilize the microdroplets. Accordingly, a microdroplet may involve a surfactant stabilized emulsion. Any convenient surfactant that allows for the desired reactions to be performed in the drops may be used. In other aspects, a microdroplet is not stabilized by surfactants or particles.

The surfactant used depends on a number of factors such as the oil and aqueous phases (or other suitable immiscible phases, e.g., any suitable hydrophobic and hydrophilic phases) used for the emulsions. For example, when using aqueous droplets in a fluorocarbon oil, the surfactant may have a hydrophilic block (PEG-PPO) and a hydrophobic fluorinated block (Krytox FSH). If, however, the oil was switched to be a hydrocarbon oil, for example, the surfactant would instead be chosen so that it had a hydrophobic hydrocarbon block, like the surfactant ABIL EM90. In selecting a surfactant, desirable properties that may be considered in choosing the surfactant may include one or more of the following: (1) the surfactant has low viscosity; (2) the surfactant is immiscible with the polymer used to construct the device, and thus it doesn't swell the device; (3) biocompatibility; (4) the assay reagents are not soluble in the surfactant; (5) the surfactant exhibits favorable gas solubility, in that it allows gases to come in and out; (6) the surfactant has a boiling point higher than the temperature used for MDA or that of any other reactions the droplets will be exposed to; (7) the emulsion stability; (8) that the surfactant stabilizes drops of the desired size; (9) that the surfactant is soluble in the carrier phase and not in the droplet phase; (10) that the surfactant has limited fluorescence properties; and (11) that the surfactant remains soluble in the carrier phase over a range of temperatures.

Other surfactants can also be envisioned, including ionic surfactants. Other additives can also be included in the oil to stabilize the drops, including polymers that increase droplet stability at temperatures above 35° C.

In some embodiments a suitable surfactant is a PEG-PFPE amphiphilic block copolymer surfactant. Such a surfactant may be utilized in a shaken emulsion MDA method. In some embodiments a suitable oil for use in the preparation of microdroplets, e.g., shaken emulsion microdroplets is the fluorinated oil HFE-7500.

In some embodiments, the nucleic acid template molecule may be encapsulated in a multiple-emulsion microdroplet, wherein each multiple-emulsion microdroplet includes a first miscible phase fluid surrounded by an immiscible shell, wherein the multiple-emulsion microdroplet is positioned in a second miscible phase carrier fluid. In some embodiments, the sample may be diluted prior to encapsulation, e.g., so as to encapsulate a controlled number of cells, viruses, and/or nucleic acids in the multiple-emulsion microdroplets. Nucleic acid amplification reagents, e.g., MDA reagents, may be added to the multiple-emulsion microdroplets at the time of encapsulation or added to the multiple-emulsion microdroplets at a later time using one or more of the methods described herein. The multiple-emulsion microdroplets are then subjected to nucleic acid amplification conditions. In some embodiments, a label is added such that if a multiple-emulsion microdroplet contains a nucleic acid template molecule, the multiple-emulsion microdroplet becomes detectably labeled, e.g., fluorescently labeled as a result of a fluorogenic assay, such as Sybr staining of amplified DNA. To recover the amplified nucleic acids, the detectably labeled multiple-emulsion microdroplets may be sorted using microfluidic (e.g., dielectrophoresis, membrane valves, etc.) or non-microfluidic techniques (e.g., FACS).

In some embodiments, the microdroplet includes a nucleic acid template molecule encapsulated or compartmentalized within the microdroplet and an MDA mixture including a DNA polymerase enzyme, a plurality of MDA reagents, and a plurality of MDA primers. In other aspects, the microdroplet may further include a detection component. As described herein, such microdroplets may also include PCR amplification reagents.

In some embodiments, the microdroplet includes a single nucleic acid template molecule. In other embodiments, there may be multiple nucleic acid template molecules compartmentalized in a single microdroplet.

In some embodiments, the microdroplet, prior to the introducing and incubating steps, does not include more than one nucleic acid template molecule. In other embodiments, the microdroplet, prior to introducing and incubating steps, may include multiple nucleic acid template molecules.

In some embodiments, the number of nucleic acid template molecules to be amplified can be varied by controlling the number of microdroplets which are generated. In other embodiments, the size of the microdroplet may be varied in order to obtain a predetermined amount of MDA amplification products derived from the nucleic acid template molecule.

In some embodiments, both microfluidic and non-microfluidic methods may be utilized to generate microdroplets to provide MDA amplification products.

In some embodiments, the starting amount of the nucleic acid template molecule (prior to amplification) is low, e.g., not more than 10 fg (e.g., not more than 5 fg or not more than 1 fg) of the nucleic acid template molecule is encapsulated in the microdroplet. In some embodiments, between about 10 fg and about 1 fg (e.g., between about 5 fg and 1 fg) is encapsulated in the microdroplet prior to amplification. In some embodiments, the microdroplet may also include a detection component, such as a fluorescent reporter. The fluorescent reporter may indicate when a specific microdroplet undergoes amplification.

In some embodiments, the microdroplet may include amplicons produced from the encapsulated nucleic acid template molecule. As described herein, "amplicons" generally refers to an amplification product of products, which are the product of natural or artificial amplification. The term amplicon may refer generally to one or more copies of a genomic sequence, such as an RNA or DNA sequence.

In some embodiments, the internal volume of the microdroplet may be about 0.01 µL or less, about 0.1 µL or less, 1 µL or less, about 5 µL or less, 10 µL or less, 100 µL or less, or 1000 µL or less. In some embodiments, the internal volume of the microdroplet may be about 1 µL or less, about 10 µL or less, or 100 µL or less. In some embodiments, the internal volume of the microdroplet may encompass a liquid volume which ranges between picoliters and femotliters (e.g., about 0.001 µL to about 1000 µL). In some embodiments, the internal volume of the microdroplet extends strictly below the nanoliter level (e.g., strictly picoliter, strictly femtoliter, or combination thereof).

In some embodiments, the initial concentration of the nucleic acid template molecule(s) in the microdroplet is from about 0.001 pg to about 10 pg, e.g., from about 0.01 pg to about 1 pg, or from about 0.1 pg to about 1 pg.

In some examples, the microdroplets may be created as polydisperse microdroplets or monodisperse microdroplets.

Adding Reagents to Microdroplets, Multiple-Emulsion Microdroplets and GUVs

In practicing the subject methods, a number of reagents may need to be added to the microdroplets, in one or more steps (e.g., about 2, about 3, about 4, or about 5 or more steps). The means of adding reagents to the microdroplets may vary in a number of ways depending for example, on the emulsification stage of the microdroplets, e.g., different approaches may be applicable to the addition of reagents to single emulsion microdroplets relative to multiple-emulsion microdroplets, such as double emulsion microdroplets. Approaches of interest include, but are not limited to, those described by Ahn, et al., Appl. Phys. Lett. 88, 264105 (2006); Priest, et al., Appl. Phys. Lett. 89, 134101 (2006); Abate, et al., PNAS, Nov. 9, 2010 vol. 107 no. 45 19163-19166; and Song, et al., Anal. Chem., 2006, 78 (14), pp 4839-4849; the disclosures of which are incorporated herein by reference.

For instance, a reagent may be added to a single emulsion microdroplet by a method involving merging a microdroplet with a second microdroplet that contains the reagent(s). The reagent(s) that are contained in the second microdroplet may be added by any convenient means, specifically including those described herein. This microdroplet may be merged with the first microdroplet to create a microdroplet that includes the contents of both the first microdroplet and the second microdroplet.

One or more reagents may also, or instead, be added to single emulsion microdroplets using techniques such as droplet coalescence, and/or picoinjection. In droplet coalescence, a target microdroplet may be flowed alongside a microdroplet containing the reagent(s) to be added to the target microdroplet. The two microdroplets may be flowed such that they are in contact with each other, but not touching other microdroplets. These microdroplets may then be passed through electrodes or other means of applying an electrical field, wherein the electric field may destabilize the microdroplets such that they are merged together.

In picoinjection, a target microdroplet may be flowed past a channel containing the reagent(s) to be added, wherein the reagent(s) are at an elevated pressure. Due to the presence of the surfactants, however, in the absence of an electric field, the microdroplet will flow past without being injected, because surfactants coating the microdroplet may prevent the fluid(s) from entering. However, if an electric field is applied to the microdroplet as it passes the injector, fluid containing the reagent(s) will be injected into the microdroplet. The amount of reagent added to the microdroplet may be controlled by several different parameters, such as by adjusting the injection pressure and the velocity of the flowing drops, by switching the electric field on and off, and the like.

In other aspects, one or more reagents may also, or instead, be added to a single emulsion microdroplet by a method that does not rely on merging two microdroplets together or on injecting liquid into a microdroplet. Rather, one or more reagents may be added to a microdroplet by a method involving the steps of emulsifying a reagent into a stream of very small drops, and merging these small drops with a target microdroplet. Such methods are referred to herein as "reagent addition through multiple-drop coalescence." These methods take advantage of the fact that due to the small size of the drops to be added compared to that of the target microdroplet, the small drops will flow faster than the target microdroplets and collect behind them. The collection can then be merged by, for example, applying an electric field. This approach can also, or instead, be used to add multiple reagents to a microdroplet by using several co-flowing streams of small drops of different fluids. To enable effective merger of the tiny and target microdroplets, it is important to make the tiny drops smaller than the channel containing the target microdroplets, and also to make the distance between the channel injecting the target microdroplets from the electrodes applying the electric field sufficiently long so as to give the tiny drops time to "catch up" to the target microdroplets. If this channel is too short, not all tiny drops will merge with the target microdroplet and less than the desired amount of reagent may be added. To a certain degree, this can be compensated for by increasing the magnitude of the electric field, which tends to allow drops that are farther apart to merge. In addition to making the tiny drops on the same microfluidic device, they can also, or instead, be made offline using another microfluidic drop maker or through homogenization and then injecting them into the device containing the target microdroplets.

Accordingly, in certain aspects a reagent is added to a microdroplet by a method involving emulsifying the reagent into a stream of droplets, wherein the droplets are smaller than the size of the microdroplet; flowing the droplets together with the microdroplet; and merging a droplet with the microdroplet. The diameter of the droplets contained in the stream of droplets may vary ranging from about 75% or less than that of the diameter of the microdroplet, e.g., the diameter of the flowing droplets is about 75% or less than that of the diameter of the microdroplet, about 50% or less than that of the diameter of the microdroplet, about 25% or less than that of the diameter of the microdroplet, about 15% or less than that of the diameter of the microdroplet, about 10% or less than that of the diameter of the microdroplet, about 5% or less than that of the diameter of the microdroplet, or about 2% or less than that of the diameter of the microdroplet. In certain aspects, a plurality of flowing droplets may be merged with the microdroplet, such as 2 or more droplets, 3 or more, 4 or more, or 5 or more. Such merging may be achieved by any convenient means, including but not limited to by applying an electric field, wherein the electric field is effective to merge the flowing droplet with the microdroplet.

As a variation of the above-described methods, the fluids may be jetting. That is, rather than emulsifying the fluid to be added into flowing droplets, a long jet of this fluid can be formed and flowed alongside the target microdroplet. These two fluids can then be merged by, for example, applying an electric field. The result is a jet with bulges where the microdroplets are, which may naturally break apart into droplets of roughly the size of the target microdroplets before the merger, due to the Rayleigh plateau instability. A number of variants are contemplated. For instance, one or more agents may be added to the jetting fluid to make it easier to jet, such as gelling agents and/or surfactants. Moreover, the viscosity of the continuous fluid could also be adjusted to enable jetting, such as that described by Utada, et al., *Phys. Rev. Lett.* 99, 094502 (2007), the disclosure of which is incorporated herein by reference.

In other aspects, one or more reagents may be added using a method that uses the injection fluid itself as an electrode, by exploiting dissolved electrolytes in solution.

In another aspect, a reagent is added to a microdroplet formed at an earlier time by enveloping the microdroplet to which the reagent is to be added (i.e., the "target microdroplet") inside a drop containing the reagent to be added (the "target reagent"). In certain embodiments such a method is carried out by first encapsulating the target microdroplet in a shell of a suitable hydrophobic phase, e.g., oil, to form a double emulsion. The double emulsion is then encapsulated by a microdroplet containing the target reagent to form a triple emulsion. To combine the target drop with the drop containing the target reagent, the double emulsion is then burst open using any suitable method, including, but not limited to, applying an electric field, adding chemicals that destabilizes the microdroplet interface, flowing the triple emulsion through constrictions and other microfluidic geometries, applying mechanical agitation or ultrasound, increasing or reducing temperature, or by encapsulating magnetic particles in the microdroplet that can rupture the double emulsion interface when pulled by a magnetic field.

Aspects of the above-described methods of adding reagents to microdroplets are described in more detail in International PCT Application Publication No. WO2014/ 028378, the disclosure of which is incorporated by reference herein in its entirety and for all purposes.

While the above methods of adding reagents to microdroplets may be suitable for the addition of reagents to single emulsion microdroplets, one or more of the above methods may not be suitable for the addition of reagents directly to multiple-emulsion microdroplets, such as double emulsion microdroplets, and/or GUVs. This may be the case, for example, where such methods would disrupt the structure of the multiple-emulsion microdroplets and/or GUVs. The above methods may find use, however, in adding reagents to single emulsion microdroplets which are then encapsulated to form multiple-emulsion microdroplets and/or GUVs. Accordingly, additional methods of adding reagents to multiple-emulsion microdroplets and/or GUVs are described below. For example, in some embodiments, reagents, such as detectable labels designed to detectably label a nucleic acid amplification product and/or nucleic acid amplification reagents designed to produce a nucleic acid amplification product, may be added to a multiple-emulsion microdroplet and/or GUV by adding the reagents to a miscible phase carrier fluid, wherein the reagents diffuse from the miscible phase carrier fluid, through the immiscible shell of the multiple-emulsion microdroplet and/or GUV, and into the first miscible phase fluid of the multiple-emulsion microdroplet and/or GUV.

In some embodiments, a multiple-emulsion microdroplet and/or GUV is a second multiple-emulsion microdroplet and/or GUV and a method of adding nucleic acid amplification reagents to the second multiple-emulsion microdroplet and/or GUV includes encapsulating a nucleic acid, e.g., a target nucleic acid, in a first multiple-emulsion microdroplet and/or GUV, encapsulating the amplification reagents and the first multiple-emulsion microdroplet in the second-multiple emulsion microdroplet and/or GUV, and rupturing the first multiple-emulsion microdroplet and/or GUV thereby bringing the nucleic acid into contact with the amplification reagents.

In some embodiments, a multiple-emulsion microdroplet and/or GUV is a second multiple-emulsion microdroplet and/or GUV and a method of adding nucleic acid amplification reagents to the second multiple-emulsion microdroplet and/or GUV includes encapsulating nucleic acid amplification reagents in a first multiple-emulsion microdroplet and/or GUV, encapsulating a nucleic acid, e.g., a target nucleic acid, and the first multiple-emulsion microdroplet and/or GUV in the second-multiple emulsion microdroplet and/or GUV, and rupturing the first multiple-emulsion microdroplet and/or GUV thereby bringing the nucleic acid into contact with the amplification reagents.

In some embodiments, a multiple-emulsion microdroplet and/or GUV is a first multiple-emulsion microdroplet and/or GUV, and a suitable method includes adding a reagent to the first multiple-emulsion microdroplet and/or GUV by encapsulating the first multiple-emulsion microdroplet and/or GUV in a second multiple-emulsion microdroplet and/or GUV including the reagent and rupturing the first multiple-emulsion microdroplet and/or GUV within the second multiple-emulsion microdroplet and/or GUV to bring the reagent into contact with the contents of the first multiple-emulsion microdroplet and/or GUV.

In some embodiments, a multiple-emulsion microdroplet and/or GUV is a second multiple-emulsion microdroplet and/or GUV, and a suitable method includes adding a reagent to the second multiple-emulsion microdroplet and/or GUV by encapsulating a first multiple-emulsion microdroplet and/or GUV including the reagent in the second multiple-emulsion microdroplet and/or GUV and rupturing the first multiple-emulsion microdroplet and/or GUV within the second multiple-emulsion microdroplet and/or GUV to bring the reagent into contact with the contents of the second multiple-emulsion microdroplet and/or GUV.

Detecting PCR Products

In practicing the subject methods, the manner in which nucleic acid amplification products, e.g., PCR products, may be detected may vary. For example, if the goal is simply to count the number of a particular cell type, e.g., tumor cells, present in a population, this may be achieved by using a simple binary assay in which SybrGreen, or any other stain and/or intercalating stain, is added to each multiple-emulsion microdroplet and/or GUV so that in the event a characterizing gene, e.g., an oncogene, is present and PCR products are produced, the multiple-emulsion microdroplet and/or GUV will become fluorescent. The change in fluorescence may be due to fluorescence polarization. The detection component may include the use of an intercalating stain (e.g., SybrGreen).

A variety of different detection components may be used in practicing the subject methods, including using fluorescent dyes known in the art. Fluorescent dyes may typically be divided into families, such as fluorescein and its derivatives; rhodamine and its derivatives; cyanine and its derivatives; coumarin and its derivatives; Cascade Blue and its derivatives; *Lucifer* Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like. Descriptions of fluorophores and their use, can be found in, among other places, R. Haugland, Handbook of Fluorescent Probes and Research Products, 9th ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, Va.

In other aspects, particularly if a goal is to further characterize the nucleic acids present, e.g., oncogenes, additional testing may be needed. For instance, in the case of the multiplex assays this may be achieved by having optical outputs that relate which of the gene(s) are amplified in the multiple-emulsion microdroplet and/or GUV. An alternative approach would be to use a binary output, for example, with an intercalated stain, to determine which multiple-emulsion microdroplets and/or GUVs have any oncogenes. These can then be sorted to recover these microdroplets and/or GUVs so that they could be analyzed in greater detail to determine which oncogenes they contain. To determine the oncogenes present in such a microdroplet and/or GUY, microfluidic techniques or nonmicrofluidic techniques could be used. Using non-microfluidic techniques, a microdroplet and/or GUV identified as containing an oncogene can be placed into a well on a wellplate where it will be diluted into a larger volume, releasing all of the PCR products that were created during the multiplexed PCR reaction. Samples from this well can then be transferred into other wells, into each of which would be added primers for one of the oncogenes. These wells would then be temperature-cycled to initiate PCR, at which point an intercalating stain would be added to cause wells that have matching oncogenes and primers to light up.

In practicing the subject methods, therefore, a component may be detected based upon, for example, a change in fluorescence. In certain aspects, the change in fluorescence is due to fluorescence resonance energy transfer (FRET). In this approach, a special set of primers may be used in which the 5' primer has a quencher dye and the 3' primer has a fluorescent dye. These dyes can be arranged anywhere on the primers, either on the ends or in the middles. Because the primers are complementary, they will exist as duplexes in solution, so that the emission of the fluorescent dye will be quenched by the quencher dye, since they will be in close proximity to one another, causing the solution to appear dark. After PCR, these primers will be incorporated into the long PCR products, and will therefore be far apart from one another. This will allow the fluorescent dye to emit light, causing the solution to become fluorescent. Hence, to detect if a particular oncogene is present, one may measure the intensity of the microdroplet and/or GUV at the wavelength of the fluorescent dye. To detect if different oncogenes are present, this would be done with different colored dyes for the different primers. This would cause the microdroplet and/or GUV to become fluorescent at all wavelengths corresponding to the primers of the oncogenes present in the cell.

Sorting

In practicing the methods of the present disclosure, one or more sorting steps may be employed. Sorting approaches of interest include, but are not necessarily limited to, approaches that involve the use of membrane valves, bifurcating channels, surface acoustic waves, and/or dielectrophoresis. Sorting approaches of interest further include those described by Agresti, et al., PNAS vol. 107, no 9, 4004-4009; the disclosure of which is incorporated herein by reference. A population may be enriched by sorting, in that a population containing a mix of members having or not having a desired property may be enriched by removing those members that do not have the desired property, thereby producing an enriched population having the desired property.

Sorting may be applied before or after any of the steps described herein. Moreover, two or more sorting steps may be applied to a population of microdroplets, e.g., single emulsion microdroplets, multiple-emulsion microdroplets and/or GUVs, e.g., about 2 or more sorting steps, about 3 or more, about 4 or more, or about 5 or more, etc. When a plurality of sorting steps is applied, the steps may be substantially identical or different in one or more ways (e.g., sorting based upon a different property, sorting using a different technique, and the like).

Microdroplets may be sorted based on one or more properties. Properties of interest include, but are not limited to, the size, viscosity, mass, buoyancy, surface tension, electrical conductivity, charge, magnetism, fluorescence, and/or presence or absence of one or more components. In certain aspects, sorting may be based at least in part upon the presence or absence of a cell in the microdroplet. In certain aspects, sorting may be based at least in part based upon the detection of the presence or absence of nucleic acid amplification products, e.g., PCR amplification products, e.g., as indicated by the detection of a fluorescent PCR amplification product.

Microdroplet sorting may be employed, for example, to remove microdroplets in which no cells are present. Encapsulation may result in one or more microdroplets, including a majority of the microdroplets, in which no cell is present. If such empty microdroplets were left in the system, they would be processed as any other microdroplet, during which reagents and time would be wasted. To achieve the highest speed and efficiency, these empty microdroplets may be removed with microdroplets sorting. For example, a drop maker may operate close to the dripping-to-jetting transition such that, in the absence of a cell, 8 μm drops are formed; by contrast, when a cell is present the disturbance created in the flow will trigger the breakup of the jet, forming drops 25 μm in diameter. The device may thus produce a bi-disperse population of empty 8 μm drops and single-cell containing 25 μm drops, which may then be sorted by size using, e.g., a hydrodynamic sorter to recover only the larger, single-cell containing drops.

Passive sorters of interest include hydrodynamic sorters, which sort microdroplets into different channels according to size, based on the different ways in which small and large microdroplets travel through the microfluidic channels. Also of interest are bulk sorters, a simple example of which is a tube containing microdroplets of different mass in a gravitational field. By centrifuging, agitating, and/or shaking the tube, lighter microdroplets that are more buoyant will naturally migrate to the top of the container. Microdroplets that have magnetic properties could be sorted in a similar process, except by applying a magnetic field to the container, towards which microdroplets with magnetic properties will naturally migrate according to the magnitude of those properties. A passive sorter as used in the subject methods may also involve relatively large channels that will sort large numbers of microdroplets simultaneously based on their flow properties.

Picoinjection can also be used to change the electrical properties of single-emulsion microdroplets. This could be used, for example, to change the conductivity of the microdroplets by adding ions, which could then be used to sort them, for example, using dielectrophoresis. Alternatively, picoinjection can also be used to charge the microdroplets, e.g., drops. This could be achieved by injecting a fluid into the microdroplets that is charged, so that after injection, the microdroplets would be charged. This would produce a collection of microdroplets in which some were charged and others not, and the charged microdroplets could then be extracted by flowing them through a region of electric field, which will deflect them based on their charge amount. By injecting different amounts of liquid by modulating the piocoinjection, or by modulating the voltage to inject different charges for affixed injection volume, the final charge on the microdroplets could be adjusted, to produce microdroplets with different charge. These would then be deflected by different amounts in the electric field region, allowing them to be sorted into different containers.

Flow cytometry (FC) may be utilized as an alternative to on-chip microdroplet sorting in any of the methods described herein. Such a method, along with devices which may be utilized in the practice of the method, are described in Lim and Abate, *Lab Chip,* 2013, 13, 4563-4572; the disclosure of which is incorporated herein by reference in its entirety and for all purposes. Briefly, microdroplets may be formed and manipulated, e.g., using techniques like splitting and picoinjection as described herein, resulting in single emulsions. These single emulsions may then be double emulsified, e.g., to provide multiple-emulsion microdroplets and/or GUVs as described herein, e.g., using one or more devices as described herein or in Lim and Abate, *Lab Chip,* 2013, 13, 4563-4572. The double emulsions may then be analyzed via FC, e.g., FACS.

Devices which may be utilized to form double emulsions and/or GUVs suitable for FC analysis and the characterization and application thereof are described in greater detail herein with reference to FIGS. 1, 2, 6 and 8-12. A workflow scheme for an embodiment including sorting via FACS is provided in FIG. 6.

Multiple-emulsion microdroplets, e.g., double emulsions, and/or GUVs, generated using the methods and devices of the present disclosure can be used to conduct a variety of encapsulated chemical and biological reactions including, for example, reactions involving enzymes, such as PCR. In many instances, the result of the reaction may be a product that may be of interest to detect. In addition, it may be of interest to recover multiple-emulsion microdroplets and/or GUVs that have different levels of the product, or a combination of multiple products. This can be accomplished using the invention in a variety of ways. For example, reactions can be partitioned into the multiple-emulsion microdroplet and/or GUV reactors such that different multiple-emulsion microdroplets and/or GUVs react to different levels and have different final product concentrations. The multiple-emulsion microdroplets and/or GUVs can then be interrogated using, for example, spectrographic techniques, such as optical or fluorescent imaging, flow cytometry, Raman spectroscopy, mass-spectrometry, etc. These methods, or combinations thereof, can be used to determine the concentrations of different compounds in the multiple-emulsion microdroplets and/or GUVs. These methods can be combined with a mechanism for sorting multiple-emulsion microdroplets and/or GUVs using, for example, microfluidic based sorting or flow cytometry in the case of double emulsions. The contents of the positively and negatively sorted multiple-emulsion microdroplets and/or GUVs can be analyzed to identify different properties of these sorted pools.

Additionally, in some instances, it may be desirable to load individual positively sorted droplets into isolated wells for further study enabling, for example, additional, detailed individual analysis of each positively sorted droplet. As a non-limiting example, the methods and devices of the present disclosure can be used to interrogate viruses containing a specific nucleic acid sequence. Viruses from a heterogeneous population can, for example, be loaded into multiple-emulsion microdroplets, e.g., double emulsions, and/or GUVs with reagents sufficient for lysis and amplification of target nucleic acids. The multiple-emulsion microdroplets and/or GUVs can then be analyzed and sorted with flow cytometry to detect and recover all droplets that underwent amplification of the target nucleic acids. These droplets can be sorted into a single positive pool or sorted individually into wells on a well plate array, for example. They may even be loaded in specific groups, if desired, so that each well on the array has a desired combination of positive events, which may all be the same or exhibit different amplification targets. The sorted droplets can then be subjected to additional analysis such as, for example, mass spectrometry or next generation sequencing.

In the pooled analysis case, the nucleic acids from all cells loaded into the positive container will be mixed together and analyzed as a whole. However, by loading single droplets into wells, the contents of each well can be analyzed individually such as, for example, by barcoding the nucleic acids in each well before pooling and sequencing. This permits, for example, the lysis of single viral genomes of the target species to not only detect the target species but recover individual genomes so that comparisons between different members of the same species can be obtained. Such an analysis is useful for a variety of applications such as metagenomics or for studying viral diversity.

In some embodiments of the invention, it is desirable to amplify the target molecules in addition to the amplification that is used for detection to enable, for example, additional analyses on sorted target nucleic acids. For example, in some applications, the target will comprise nucleic acids desirable for sequencing, but the quantity of nucleic acids provided by the target will be too small to enable sequencing. In these instances, an amplification procedure, such as a specific PCR and/or non-specific multiple displacement amplification can be applied, before or after sorting of the multiple-emulsion microdroplets and/or GUVs. For example, in the case of a virus with a relatively small, linear genome, such as polio or HIV, a PCR can be performed prior to or post sorting to provide sufficient copies of each genome after sorting to enable sequencing analysis. For example individual genomes may be encapsulated in droplets and subjected to amplification of the whole or a portion of the genome. Simultaneous with or following this reaction, an additional amplification can be performed to identify the genome in the multiple-emulsion microdroplets and/or GUVs, and the multiple-emulsion microdroplets and/or GUVs sorted based on this information. These sorted double emulsions, now containing a large number of copies of the target nucleic acid, may then be more easily subjected to follow-on analyses.

Alternatively, individual genomes can be encapsulated and subjected to the detection amplification such that, for instance, each positive multiple-emulsion microdroplet and/or GUV contains just one copy of the full length target nucleic acid and a large number of the small detection region amplicons. Based on these amplicons, the multiple-emulsion microdroplets and/or GUVs can be recovered as a pool, providing for each positive sorting event one full length copy of the target genome. To prepare a sequencing library, these positive genomes can then be amplified using a PCR that is specific and has primers that flank the regions desired or, alternatively, a non-specific method to amplify the entirety of the genome, such as multiple displacement amplification (MDA) or multiple annealing and looping based amplification cycles (MALBAC). In addition, if the positive multiple-emulsion microdroplets and/or GUVs are not pooled, for example, if the positive multiple-emulsion microdroplets and/or GUVs are sorted into a well plate array, and then subjected to amplification using a PCR that is specific and has primers that flank the region desired, the resulting individual amplicons can be used directly as material for Sanger sequencing.

A powerful advantage of the disclosed methods and devices is its ability to perform a large number of independent, isolated reactions and then apply a variety of spectrographic techniques to detect reaction products and sort to recover specific reactors that underwent a desired reaction. A challenge that may arise in the performance of the disclosed methods is that, in some instances, positive events that are desired for further analysis might be very rare. For example, if the disclosed methods are used to detect a specific virus in a large, diverse pool of viruses, in which the desired virus is present at a very low level, then a large number of individual viruses might need to be analyzed in order to recover the specific virus. And, if it is desirable to recover multiple instances of the species, then an even larger number of total viruses might need to be analyzed. Since the number of reactions that can be performed and sorted with the disclosed methods is finite, there may be instances in which the target is too rare to detect reliably.

In certain instances, the methods of the present disclosure can be used in a tiered sorting process to recover extremely rare events, each sorting round providing an enrichment factor. By performing the sorting on the sample repeatedly, the sample can be enriched for targets so that the total enrichment becomes the multiplicative product of all of the individual enrichments. For example, suppose that a system of the present disclosure is capable of generating, analyzing, and sorting at most 1 million multiple-emulsion microdroplets and/or GUVs. Under ideal conditions, this means that an event that is present at, for example, 1 in a billion is unlikely to be detected with a straightforward usage of the system. However, by performing tiered sorting and enriching the target at each sorting round, such rare events can be recovered.

For example, in a first round, 10 billion entities for testing can be isolated in the million multiple-emulsion microdroplets and/or GUVs such that each multiple-emulsion microdroplet and/or GUV contains about 10,000 entities. If the target entity is present at 1 in 1 billion, then in such a sample there will be at most 10 multiple-emulsion microdroplets and/or GUVs that contain the target and are thus positive. These will be sorted, each providing 10,000 entities, yielding a total number of 100,000 entities in which the 10 desired are mixed. In some instances, this enrichment may be sufficient, but in others, it may be desirable to enrich further, even to 100% purity. In this case, the tiered sorting approach can be used, loading the 100,000 entities into 1 million droplets such that, for example, 1 in 10 droplets contains 1 entity, loading in accordance with a Poisson distribution. In this instance, the majority of droplets that are determined to be positive for the target will contain only that target entity, although due to the random nature of Poisson loading, some will also contain negative off-target entities that happened to be co-encapsulated with a positive.

When the 1 million droplets are analyzed and sorted, 10 will again be determined to contain the target entity and will be recovered with sorting, providing a highly enriched population that is almost completely pure for the target. To enrich further, additional round of sorting can be performed. The power of tiered sorting is that in this instance the final enrichment is the multiplicative product of the individual enrichments. For example, if the method is able to enrich a maximum of $10^3$ in one round, then by performing the sorting twice on the same sample the final enrichment will become $10^3 \times 10^3 = 10^6$, while another round will provide a final enrichment of, for example, $10^9$. Additionally, the enrichments can be similar in each round or different, depending on the desires of the user. For example, a first round with a small number of relations can be used to provide an enrichment of, for instance, $10^3$, and then a more intensive round can be used to perform an enrichment of $10^6$, yielding again a $10^9$ final enrichment. These values can be adjusted as needed to optimize for the particular application but the tiered sorting methods generally provide the very powerful advantage of being able to enrich extremely rare events out of massive populations even with finite enrichment power.

When using the disclosed methods to enrich with PCR activated sorting, special considerations may need to be taken to ensure that each enrichment is successful and increases the concentration of the target in the solution. For example, if the goal is to detect a very rare virus in a large population, then in the first round, amplification primers can be generated against a specific sequence in the viral genome. These will yield many copies of that region which will be collected into the sorted chamber. If this same region is used in additional sorting rounds, then the product amplicons of earlier rounds will be detected and sorted, leading to a large number of positive events that will erode the power of the method for achieving large enrichments. In this instance, the primers in later rounds can be modified so as to not detect amplification products from earlier rounds. This can be achieved in a number of ways including, for example, using a nested PCR approach in which the primers in later rounds amplify from beyond the region that is used in the early rounds so that products from early rounds cannot be amplified in later rounds. Alternatively, completely distinct regions can be targeted in later rounds, such as different portions of the same gene or different genes altogether. Combinations of these methods can also be used to achieve highly enriched samples.

Suitable Subjects and/or Samples

The subject methods may be applied to biological samples taken from a variety of different subjects. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans. The subject methods may be applied to human subjects of both genders and at any stage of development (i.e., neonates, infant, juvenile, adolescent, adult), where in certain embodiments the human subject is a juvenile, adolescent or adult. While the present invention may be applied to a human subject, it is to be understood that the subject methods may also be carried-out on other animal subjects (that is, in "non-human subjects") such as, but not limited to, birds, mice, rats, dogs, cats, livestock and horses. Accordingly, it is to be understood that any subject in need of assessment according to the present disclosure is suitable.

Moreover, suitable subjects include those who have and those who have not been diagnosed with a condition, such as cancer. Suitable subjects include those that are and are not displaying clinical presentations of one or more cancers. In certain aspects, a subject may one that may be at risk of developing cancer, due to one or more factors such as family history, chemical and/or environmental exposure, genetic mutation(s) (e.g., BRCA1 and/or BRCA2 mutation), hormones, infectious agents, radiation exposure, lifestyle (e.g., diet and/or smoking), presence of one or more other disease conditions, and the like.

As described more fully above, a variety of different types of biological samples may be obtained from such subjects. In certain embodiments, whole blood is extracted from a subject. When desired, whole blood may be treated prior to practicing the subject methods, such as by centrifugation, fractionation, purification, and the like. The volume of the whole blood sample that is extracted from a subject may be 100 mL or less, e.g., about 100 mL or less, about 50 mL or less, about 30 mL or less, about 15 mL or less, about 10 mL or less, about 5 mL or less, or about 1 mL or less.

The subject methods and devices provided herein are compatible with both fixed and live cells. In certain embodiments, the subject methods and devices are practiced with live cells. In other embodiments, the subject methods and devices are practiced with fixed cells. Fixing a cellular sample allows for the sample to be washed to extract small molecules and lipids that may interfere with downstream analysis. Further, fixing and permeabilizing cells allows the cells to be stained with antibodies for surface proteins as well as intracellular proteins. Combined with the nucleic amplification methods described herein, such staining can be used to achieve high levels of multiplexing because the antibodies are localized to the cell sample, while the nucleic amplification products are free within a multiple-emulsion microdroplet and/or GUV. Such a configuration allows for dyes of the same color to be used for antibodies and for amplicons produced by nucleic acid amplification. Any suitable method can be used to fix cells, including but not limited to, fixing using formaldehyde, methanol and/or acetone.

Reactions in Multiple-Emulsion Microdroplets and/or GUVs Generally

The methods and devices disclosed herein generally facilitate the performance of a large numbers of compartmentalized reactions and the subsequent reading and sorting of those reactions using a variety of detection methods, such as spectroscopy, chemical techniques, biological techniques, sequencing, etc. Reactions can include organic or inorganic reactions performed without biomolecules, or reactions involving biomolecules and/or cells, such as enzymatic reactions, for example, PCR. Reactions may also involve cellular materials or cell-based extracts, including transcription and translation extracts that can express DNA, RNA, and protein without the use of living cells. This can be used for synthetic biologic applications including, for example, screening a pathway for activity.

For example, a pathway implemented by one or more proteins can be encoded by nucleic acids encapsulated in multiple-emulsion microdroplets, e.g., double emulsions, and/or GUVs with cell-free extracts capable of expressing the one or more pathway proteins. Assay components can also be included, allowing testing of the pathway. Based on the pathway activity and measurements of the assay, the reactors can be sorted to recover multiple-emulsion microdroplets and/or GUVs that happened to encapsulate particularly desirable pathways. After sorting they can be analyzed, amplified, etc., to continue the process, either to perform screens or, alternatively, to perform directed evolution and generate enhanced pathway sequences.

Reactions in the multiple-emulsion microdroplets and/or GUVs can also be used for applications, such as nucleic acid manipulations, including the generation of sequencing libraries with less bias or to combine molecules with specific features. For example, cells expressing specific gene sequences can be encapsulated in the multiple-emulsion microdroplets and/or GUVs and then subjected to the methods of the present disclosure to amplify and link the sequences, generating a single molecule that can be analyzed or used in additional applications. For example, if the cells include human antibody generating cells, then the genes corresponding to the heavy and light chains of the cells can be linked together to create a single molecule that can be analyzed to detect the heavy and light chain pairing or to generate an antibody like molecule, such as an scFv or Fab.

Detecting Proteins or DNA with Enzyme-Linked Probes

The methods and devices described herein can be used in a variety of ways for detecting and sorting entities in a heterogeneous solution. Some embodiments described thus far accomplish this using nucleic acid amplification performed in single emulsion microdroplets or multiple-emulsion microdroplets, e.g., double emulsions, and/or GUVs, but other methods are also enabled by the present disclosure. For example, when the disclosed methods and devices are used to detect nucleic acids, this can be accomplished by, for example, encapsulating individual nucleic acid entities in the single emulsion microdroplets or multiple-emulsion microdroplets and/or GUVs and then subjecting them to amplification with primers specific for target nucleic acids, detecting the target amplicons, and then sorting based on amplification. However, other detectable signals can be generated using other means, such as by binding affinity reagents to the targets. For example, if the target is a nucleic acid, probes specific to the target can be synthesized that can hybridize to the target when present, these probes may be labeled with dyes or, in some cases, catalysts, such as enzyme based or non-enzyme based catalysts. The targets, now bound by their probes, can be subjected to purification to remove unbound probes and, the remaining material can be encapsulated in multiple-emulsion microdroplets and/or GUVs using the methods described herein.

In the case of a catalyst-linked probe, the substrate for the catalyst may also be included in the single emulsion microdroplets or multiple-emulsion microdroplets and/or GUVs. In this instance, single emulsions or multiple emulsions that contain targets will be bound with probes and, thus, will comprise catalysts, resulting in catalysis of the substrate and the generation of a product, which may, for example, be fluorescent. Over time, this will cause the single emulsion microdroplets or multiple-emulsion microdroplets and/or GUVs to fill with fluorescent product. By contrast, single emulsion microdroplets or multiple-emulsion microdroplets and/or GUVs that are empty or that contain off-target molecules will not contain catalysts, resulting in no product generation and, hence no detectable signal. The result of such an approach is a large collection of single emulsion microdroplets or multiple-emulsion microdroplets and/or GUVs, some of which are fluorescent and others dim, enabling recovery of the targets by sorting the encapsulating fluorescent single emulsion microdroplets or multiple-emulsion microdroplets and/or GUVs. This procedure can also be applied to other kinds of targets, such as biomolecules, viruses, cells, etc., that can be bound with affinity reagents, such as antibodies. In this case, affinity reagents would, for example, be bound with a catalyst, and the procedure would be performed as described above for nucleic acid targets bound by nucleic acid probes.

In both of these examples, washing may be implemented to remove unbound catalysts, which would otherwise be encapsulated in single emulsion microdroplets or multiple-emulsion microdroplets and/or GUVs and yield false positives. However, if washing to remove unbound catalysts is not desirable or possible, then an alternative approach would be to use a multiplexed assay in which, for example, the localization of two signals is used to identify a positive event. For example, if the goal is to detect a nucleic acid target that is in a solution, the probes for two different sequences on the target can be synthesized, each bound with a different catalyst that performs, for example, a reaction that yields a fluorescent product. In one embodiment, the fluorescent products for the distinct catalysts can be different colors, for example one yielding a green fluorescent product and the other a red fluorescent product. The probes can be bound to the targets, as normal. In this instance, while there will be many unbound probes in solution, in the majority of instances, the probes corresponding to the first type of catalyst will not be physical bound to the second probe with a different catalyst unless they are both bound to the same target nucleic acid.

The solutions can also be diluted as necessary to perform the hybridization at a high concentration. The concentration can then be reduced such that any given droplet-equivalent volume of solution will contain just one probe or a target with both bound probes. This solution can then be encapsulated with the substrates for the catalysts, incubated, detected, and sorted. In this embodiment, many single emulsion microdroplets or multiple-emulsion microdroplets and/or GUVs will contain just a red or green catalyst, but others will contain both a red and a green—the ones that are bound to the target. This will allow droplets containing the target nucleic acid to be differentiated from those that just contain catalysts by detecting the droplets that emit fluorescence at both wavelengths, without the need to wash.

Again, a false positive may occur when unbound probes of both catalysts happen to be co-encapsulated in the same droplet, but this can be mitigated by diluting the solution sufficiently to ensure that this event is substantially rarer than the presence of the targets, so that the double-positive single emulsion microdroplets or multiple-emulsion microdroplets and/or GUVs identified can most often be associated with the presence of a target. Similar techniques can be applied to other kinds of targets like cells or proteins using different kinds of affinity reagents, such as binding molecules like antibodies, which can again be bound with catalysts of different reactivity, etc.

Detecting Cancer

Methods according to the present disclosure also involve methods for detecting cancer. Such methods may include encapsulating in a multiple-emulsion microdroplet and/or GUV oligonucleotides obtained from a biological sample from the subject, wherein at least one oligonucleotide is present in the multiple-emulsion microdroplet and/or GUV; introducing polymerase chain reaction (PCR) reagents, a detection component, and a plurality of PCR primers into the multiple-emulsion microdroplet and/or GUV and incubating the multiple-emulsion microdroplet and/or GUV under conditions allowing for PCR amplification to produce PCR amplification products, wherein the plurality of PCR primers include one or more primers that each hybridize to one or more oncogenes; and detecting the presence or absence of the PCR amplification products by detection of the detection component, wherein detection of the detection component indicates the presence of the PCR amplification products.

Detection of one or more PCR amplification products corresponding to one or more oncogenes may be indicative that the subject has cancer. The specific oncogenes that are added to the microdroplet may vary. In certain aspects, the oncogene(s) may be specific for a particular type of cancer, e.g., breast cancer, colon cancer, and the like.

Moreover, in practicing the subject methods the biological sample from which the components are to be detected may vary, and may be based at least in part on the particular type of cancer for which detection is sought. For instance, breast tissue may be used as the biological sample in certain instances, if it is desired to determine whether the subject has breast cancer, and the like. In practicing the methods for detecting cancer, any variants to the general steps described herein, such as the number of primers that may be added, the manner in which reagents are added, suitable subjects, and the like, may be made. The above method may also be performed using single emulsion microdroplets in place of multiple-emulsion microdroplets.

Devices

As indicated above, embodiments of the invention employ microfluidics devices. Microfluidics devices of this invention may be characterized in various ways. In certain embodiments, for example, microfluidics devices have at least one "micro" channel. Such channels may have at least one cross-sectional dimension on the order of a millimeter or smaller (e.g., less than or equal to about 1 millimeter). One of skill in the art will understand that for certain applications, this dimension may be adjusted; in some embodiments the at least one cross-sectional dimension is about 500 micrometers or less. In some embodiments, again as applications permit, the cross-sectional dimension is about 100 micrometers or less (or even about 10 micrometers or less—sometimes even about 1 micrometer or less). A cross-sectional dimension is one that is generally perpendicular to the direction of centerline flow, although it should be understood that when encountering flow through elbows or other features that tend to change flow direction, the cross-sectional dimension in play need not be strictly perpendicular to flow. It should also be understood that in some embodiments, a micro-channel may have two or more cross-sectional dimensions such as the height and width of a rectangular cross-section or the major and minor axes of an elliptical cross-section. Either of these dimensions may be compared against sizes presented here. Note that micro-channels employed in this invention may have two dimensions that are grossly disproportionate—e.g., a rectangular cross-section having a height of about 100-200 micrometers and a width on the order or a centimeter or more. Of course, certain devices may employ channels in which the two or more axes are very similar or even identical in size (e.g., channels having a square or circular cross-section).

In some embodiments, microfluidic devices of this invention are fabricated using microfabrication technology. Such technology is commonly employed to fabricate integrated circuits (ICs), microelectromechanical devices (MEMS), display devices, and the like. Among the types of microfabrication processes that can be employed to produce small dimension patterns in microfluidic device fabrication are photolithography (including X-ray lithography, e-beam lithography, etc.), self-aligned deposition and etching technologies, anisotropic deposition and etching processes, self-assembling mask formation (e.g., forming layers of hydrophobic-hydrophilic copolymers), etc.

In view of the above, it should be understood that some of the principles and design features described herein can be scaled to larger devices and systems including devices and systems employing channels reaching the millimeter or even centimeter scale channel cross-sections. Thus, when describing some devices and systems as "microfluidic," it is intended that the description apply equally, in certain embodiments, to some larger scale devices.

When referring to a microfluidic "device" it is generally intended to represent a single entity in which one or more channels, reservoirs, stations, etc. share a continuous substrate, which may or may not be monolithic. A microfluidics "system" may include one or more microfluidic devices and associated fluidic connections, electrical connections, control/logic features, etc. Aspects of microfluidic devices include the presence of one or more fluid flow paths, e.g., channels, having dimensions as discussed herein.

In certain embodiments, microfluidic devices of this invention provide a continuous flow of a fluid medium. Fluid flowing through a channel in a microfluidic device exhibits many interesting properties. Typically, the dimensionless Reynolds number is extremely low, resulting in flow that always remains laminar. Further, in this regime, two fluids joining will not easily mix, and diffusion alone may drive the mixing of two compounds.

Various features and examples of microfluidic device components suitable for use with this invention will now be described.

Substrate

Substrates used in microfluidic systems are the supports in which the necessary elements for fluid transport are provided. The basic structure may be monolithic, laminated, or otherwise sectioned. Commonly, substrates include one or more microchannels serving as conduits for molecular libraries and reagents (if necessary). They may also include input ports, output ports, and/or features to assist in flow control.

In certain embodiments, the substrate choice may be dependent on the application and design of the device. Substrate materials are generally chosen for their compatibility with a variety of operating conditions. Limitations in microfabrication processes for a given material are also relevant considerations in choosing a suitable substrate. Useful substrate materials include, e.g., glass, polymers, silicon, metal, and ceramics.

Polymers are standard materials for microfluidic devices because they are amenable to both cost effective and high volume production. Polymers can be classified into three categories according to their molding behavior: thermoplastic polymers, elastomeric polymers and duroplastic polymers. Thermoplastic polymers can be molded into shapes above the glass transition temperature, and will retain these shapes after cooling below the glass transition temperature. Elastomeric polymers can be stretched upon application of an external force, but will go back to original state once the external force is removed. Elastomers do not melt before reaching their decomposition temperatures. Duroplastic polymers have to be cast into their final shape because they soften a little before the temperature reaches their decomposition temperature.

Among the polymers that may be used in microfabricated device of this invention are poly(dimethylsiloxane) (PDMS), polyamide (PA), polybutylenterephthalate (PBT), polycarbonate (PC), polyethylene (PE), polymethylmethacrylate (PMMA), polyoxymethylene (POM), polypropylene (PP), polyphenylenether (PPE), polystyrene (PS) and polysulphone (PSU). The chemical and physical properties of polymers can limit their uses in microfluidics devices. Specifically in comparison to glass, the lower resistance against chemicals, the aging, the mechanical stability, and the UV stability can limit the use of polymers for certain applications.

Glass, which may also be used as the substrate material, has specific advantages under certain operating conditions. Since glass is chemically inert to most liquids and gases, it is particularly appropriate for applications employing certain solvents that have a tendency to dissolve plastics. Additionally, its transparent properties make glass particularly useful for optical or UV detection.

Surface Treatments and Coatings

Surface modification may be useful for controlling the functional mechanics (e.g., flow control) of a microfluidic device. For example, it may be advantageous to keep fluidic species from adsorbing to channel walls or for attaching antibodies to the surface for detection of biological components.

Polymer devices in particular tend to be hydrophobic, and thus loading of the channels may be difficult. The hydrophobic nature of polymer surfaces also make it difficult to control electroosmotic flow (EOF). One technique for coating polymer surface is the application of polyelectrolyte multilayers (PEM) to channel surfaces. PEM involves filling the channel successively with alternating solutions of positive and negative polyelectrolytes allowing for multilayers to form electrostatic bonds. Although the layers typically do not bond to the channel surfaces, they may completely cover the channels even after long-term storage. Another technique for applying a hydrophilic layer on polymer surfaces involves the UV grafting of polymers to the surface of the channels. First grafting sites, radicals, are created at the surface by exposing the surface to UV irradiation while simultaneously exposing the device to a monomer solution. The monomers react to form a polymer covalently bonded at the reaction site.

Glass channels generally have high levels of surface charge, thereby causing proteins to adsorb and possibly hindering separation processes. In some situations, it may be advantageous to apply a polydimethylsiloxane (PDMS) and/or surfactant coating to the glass channels. Other polymers that may be employed to retard surface adsorption include polyacrylamide, glycol groups, polysiloxanes, glyceroglycidoxypropyl, poly(ethyleneglycol) and hydroxyethylated poly(ethyleneimine). Furthermore, for electroosmotic devices it is advantageous to have a coating bearing a charge that is adjustable in magnitude by manipulating conditions inside of the device (e.g. pH). The direction of the flow can also be selected based on the coating since the coating can either be positively or negatively charged.

Specialized coatings can also be applied to immobilize certain species on the channel surface—this process is known by those skilled in the art as "functionalizing the surface." For example, a polymethylmethacrylate (PMMA) surface may be coated with amines to facilitate attachment of a variety of functional groups or targets. Alternatively, PMMA surfaces can be rendered hydrophilic through an oxygen plasma treatment process.

Devices can be treated with chemical and/or gaseous materials in order to modify surface chemistry. In order to create transient hydrophobic channel junctions, e.g., one or more droplet forming junctions, the device may be incubated at elevated temperatures for extended periods of time. To make a permanent modification the device may be treated with Aquapel. These modifications will facilitate the creation of water-in-oil droplets, e.g., microdroplets. In contrast, in order to create transient hydrophilic channel junctions, e.g., one or more droplet forming junctions, junctions may be exposed to oxygen plasma. To make a more permanent modification the channel junctions may be extracted using solvents as described by Vickers, et al., Anal. Chem, 2006, 78 (21), pp 7446-7452. These modifications will facilitate the pinching off of water-in-oil droplets by an aqueous phase, thus facilitating double emulsion droplet formation.

When using a microfluidic device in the generation of emulsions, it may be necessary to modulate the wettability of the channel walls, however, channel wettability modification can be difficult, requiring additional device fabrication steps such as chemical or UV patterning. In some embodiments, the methods described herein can be used for facile fabrication of microfluidic devices with channel wettability. For example, in certain embodiments, microfluidic devices with channels can be treated such that certain channels receive a larger dose of plasma oxidation than other channels.

For example, a device for generating double emulsions in a two-step process using a hydrophobic first droplet maker and a hydrophilic second droplet making junction can be created by blocking the inlets of the device, for example, with tape, and leaving the outlet of the device open. The device can then be subjected to oxygen plasma treatment. Because the outlet is open, reactive oxygen ions will diffuse into the outlet channel, treating it and making it hydrophilic. Near the outlet of the channel, this will result in a large oxygen plasma dose and, hence, hydrophilic walls, but further up the channel, away from the open outlet, the oxygen will have to diffuse farther, which will result in a lower dosage. This will cause the plasma dosage to vary gradually over the length of the channel, with a high dosage at the outlet and a low dosage far from the outlet, including near all of the blocked inlets. If the plasma oxidation modifies the wettability of the channels, this can be used to achieve spatially patterned wettability in which the wettability near the outlet will be hydrophilic and farther away will be hydrophobic, as necessary to generate double emulsions.

A similar method can be used to modify the chemical properties of the device by, for example, exploiting the different reactivity of surfaces that are plasma oxidized compared to those that are not. For example, using the methods described herein, the channels can be given a spatially-patterned dosage of plasma oxidation. They can then be filled with a reagent that selectively reacts to, for example, the oxidized or non-oxidized portions of the device, thereby reacting in certain regions but not in others. This can be used to enhance chemical properties, such as wettability, or create new surface properties by attaching novel moieties to the channel surface. Features of various types can also be used to guide and modulate plasma dosage, such as long channels with narrow cross section, posts with gaps of different designed sizes, etc.

Spatial Wettability Patterning with Limited-Diffusion Plasma Oxidation

Common methods for patterning wettability rely on methods that can modify surface properties of channels with a high degree of spatial control, such as light-activated polymerization and flow-confinement of chemical treatments. These methods, however, are complex, requiring either highly controlled light patterns to be aligned with the device, or careful control of flow rates. One way to functionalize hydrophobic polymer devices to make them hydrophilic is with plasma oxidation, which has been shown to convert the normally hydrophobic wetting of PDMS with a water-oil contact angle of >90 deg. to fully wetting (contact angle 0 deg.). By spatially controlling where the plasma process is applied, it may be possible to use plasma oxidation to spatially control wettability.

Plasma oxidation relies on the ability to generate oxygen gas ions near the surface of the channels to be oxidized; if gas diffusion was limited to specific regions of the device, it would be possible to treat these regions while leaving others untreated. One way to accomplish this is to connect two reservoirs open to the atmosphere by a long, resistive channel through which gas diffusion between the reservoirs is relatively slow. If the first reservoir is open to the atmosphere and the second reservoir closed, for example by sealing the inlet of the first with a barrier, like tape, then molecules would only be able to diffuse into the second reservoir via the channel connecting it to the first, which would be relatively slow. This provides a method for spatially patterning wettability with plasma oxidation. The device, with the first inlet open and the second inlet tape-sealed, is placed into the plasma oxidizer. The chamber is evacuated and flushed with pure oxygen, as in standard oxygen plasma treatment. This allows the gas originally in the device to be replaced with pure oxygen. The plasma is then switched on, ionizing the oxygen gas and generating radicals that combine with the surface, oxidizing it. For the reaction to continue, the gas in the reservoirs may be replenished with fresh oxygen. While this happens rapidly for the first reservoir, which is connected to the open inlet, replenishment is much slower in the second reservoir, because the fresh oxygen can only enter the second reservoir via the long connecting channel. The result is that the first chamber oxidizes faster than the second chamber; if the treatment time is appropriately controlled, this allows the first chamber to be made hydrophilic while the second remains hydrophobic, generating a device with spatially-patterned wettability. Valves and other methods can be implemented to control the diffusion rate and path to generate patterns with controlled properties.

Spatially-patterning wettability with plasma oxidation may be utilized for double emulsification. Using oxygen plasma spatial wettability patterning, it is possible to functionalize a double emulsification device. To accomplish this, the device is first designed to contain two droplet generators connected via a relatively long and narrow channel that will limit oxygen diffusion during plasma treatment. For W/O/W double emulsions, the first junction may be hydrophobic and the second junction hydrophilic. Because most polymers including PDMS are natively hydrophobic and oxygen plasma treatment makes them hydrophilic, only the second junction needs to be treated. Accordingly, the inlets of the first droplet generator are sealed and those of the second droplet generator and the device outlet are left open. The device is then plasma treated, preferentially treating the second junction and making it hydrophilic, and leaving the first junction hydrophobic. One disadvantage of this method may be that the wettability will convert from hydrophilic to hydrophobic over a relatively long, smeared-out path. However, it is simple, scalable to the parallel patterning of large numbers of devices, and yields robust and reproducible patterns.

Microfluidic Elements

Microfluidic systems can contain a number of microchannels, valves, pumps, reactors, mixers and other components. Some of these components and their general structures and dimensions are discussed below.

Various types of valves can be used for flow control in microfluidic devices of this invention. These include, but are not limited to passive valves and check valves (membrane, flap, bivalvular, leakage, etc.). Flow rate through these valves are dependent on various physical features of the valve such as surface area, size of flow channel, valve material, etc. Valves also have associated operational and manufacturing advantages/disadvantages that should be taken into consideration during design of a microfluidic device.

Micropumps as with other microfluidic components are subjected to manufacturing constraints. Typical considerations in pump design include treatment of bubbles, clogs, and durability. Micropumps currently available include, but are not limited to electric equivalent pumps, fixed-stroke microdisplacement, peristaltic micromembrane and pumps with integrated check valves.

Macrodevices rely on turbulent forces such as shaking and stirring to mix reagents. In comparison, such turbulent forces are not practically attainable in microdevices; mixing in microfluidic devices is generally accomplished through diffusion. Since mixing through diffusion can be slow and inefficient, microstructures are often designed to enhance the mixing process. These structures manipulate fluids in a way that increases interfacial surface area between the fluid regions, thereby speeding up diffusion. In certain embodiments, microfluidic mixers are employed. Such mixers may be provide upstream from (and in some cases integrated with) a microfluidic separation device of this invention.

Micromixers may be classified into two general categories: active mixers and passive mixers. Active mixers work by exerting active control over flow regions (e.g. varying pressure gradients, electric charges, etc.). Passive mixers do not require inputted energy and use only "fluid dynamics" (e.g. pressure) to drive fluid flow at a constant rate. One example of a passive mixer involves stacking two flow streams on top of one another separated by a plate. The flow streams are contacted with each other once the separation plate is removed. The stacking of the two liquids increases contact area and decreases diffusion length, thereby enhancing the diffusion process. Mixing and reaction devices can be connected to heat transfer systems if heat management is needed. As with macro-heat exchangers, micro-heat exchanges can either have co-current, counter-current, or cross-flow flow schemes. Microfluidic devices frequently have channel widths and depths between about 10 μm and about 10 cm. A common channel structure includes a long main separation channel, and three shorter "offshoot" side channels terminating in either a buffer, sample, or waste reservoir. The separation channel can be several centimeters long, and the three side channels usually are only a few millimeters in length. Of course, the actual length, cross-sectional area, shape, and branch design of a microfluidic device depends on the application as well other design considerations such as throughput (which depends on flow resistance), velocity profile, residence time, etc.

Microfluidic devices described herein may include electric field generators to perform certain steps of the methods described herein, including, but not limited to, picoinjection, droplet coalescence, selective droplet fusion, and droplet sorting. In certain embodiments, the electric fields are generated using metal electrodes. In particular embodiments, electric fields are generated using liquid electrodes. In certain embodiments, liquid electrodes include liquid electrode channels filled with a conducting liquid (e.g. salt water or buffer) and situated at positions in the microfluidic device where an electric field is desired. In particular embodiments, the liquid electrodes are energized using a power supply or high voltage amplifier. In some embodiments, the liquid electrode channel includes an inlet port so that a conducting liquid can be added to the liquid electrode channel. Such conducting liquid may be added to the liquid electrode channel, for example, by connecting a tube filled with the liquid to the inlet port and applying pressure. In particular embodiments, the liquid electrode channel also includes an outlet port for releasing conducting liquid from the channel. In particular embodiments, the liquid electrodes are used in picoinjection, droplet coalescence, selective droplet fusion, and/or droplet sorting aspects of a microfluidic device described herein. Liquid electrodes may find use, for example, where a material to be injected via application of an electric field is not charged.

Liquid electrodes as described herein also have applicability outside of the specific microfluidic device applications discussed herein. For example, liquid electrodes may be utilized in a variety of devices in which metal electrodes are generally used. In addition, liquid electrodes may be particularly well suited for use in flexible devices, such as devices that are designed to be worn on the body and/or devices that must flex as a result of their operation.

In certain embodiments, one or more walls of a microfluidic device channel immediately down-stream of a junction with one or more of an input microchannel, pairing microchannel and/or picoinjection microchannel includes one or more ridges. Such ridges in the walls of the microchannel are configured to trap a layer of a suitable phase, e.g., a suitable hydrophobic phase (e.g., oil) and thereby prevent an immiscible phase, e.g., an aqueous phase, from touching the walls of the microchannel, which can cause wetting of the channel walls. Such wetting may be undesirable as it may lead to unpredictable drop formation and/or allow fluids to transfer between drops, leading to contamination. In certain embodiments, the ridges allow for the formation of drops at higher flow rate ratios R ($Q_{aq}/Q_{sum}$).

In certain embodiments, the width of one or more of the microchannels of the microfluidic device (e.g., input microchannel, pairing microchannel, pioinjection microchannel, and/or a flow channel upstream or downstream of one or more of these channels) is 100 microns or less, e.g., 90 microns or less, 80 microns or less, 70 microns or less, 60 microns or less, 50 microns or less, e.g., 45 microns or less, 40 microns or less, 39 microns or less, 38 microns or less, 37 microns or less, 36 microns or less, 35 microns or less, 34 microns or less, 33 microns or less, 32 microns or less, 31 microns or less, 30 microns or less, 29 microns or less, 28 microns or less, 27 microns or less, 26 microns or less, 25 microns or less, 20 microns or less, 15 microns or less, or 10 microns or less. In some embodiments, the width of one or more of the above microchannels is from about 10 microns to about 15 microns, from about 15 microns to about 20 microns, from about 20 microns to about 25 microns, from about 25 microns to about 30 microns, from about 30 microns to about 35 microns, from about 35 microns to about 40 microns, from about 40 microns to about 45 microns, or from about 45 microns to about 50 microns, from about 50 microns to about 60 microns, from about 60 microns to about 70 microns, from about 70 microns to about 80 microns, from about 80 microns to about 90 microns, or from about 90 microns to about 100 microns.

In certain embodiments, the base of each of the one or more ridges is from about 10 microns to about 20 microns in length, e.g., from about 11 to about 19 microns in length, from about 12 to about 18 microns in length, from about 13 to about 17 microns in length, from about 14 to about 16 microns in length, or about 15 microns in length.

In certain embodiments, the peak of each of the one or more ridges has a width of about 1 to about 10 microns, e.g., from about 1 to about 9 microns, from about 2 to about 8 microns, from about 3 to about 7 microns, from about 4 to about 6 microns, or about 5 microns. In certain embodiments, the peak of each of the one or more ridges has a width of from about 1 micron to about 2 microns, from about 2 microns to about 3 microns, from about 3 microns to about 4 microns, from about 4 microns to about 5 microns, from about 5 microns to about 6 microns, from about 6 microns to about 7 microns, from about 7 microns to about 8 microns, from about 8 microns to about 9 microns, or from about 9 microns to about 10 microns.

In certain embodiments, the height of each of the one or more ridges is from about 5 microns to about 15 microns, e.g., about 6 microns to about 14 microns, about 7 microns to about 13 microns, about 8 microns to about 12 microns, about 9 microns to about 11 microns, or about 10 microns.

In certain embodiments, the ratio of the base of each of the one or more ridges to the height of each of the one or more ridges is from about 1.0:0.75 to about 0.75:1.0. In certain embodiments, the ratio of the base of each of the one or more ridges to the width of the peak of each of the one or more ridges is about 1.0:0.5 to about 1.0:0.1, e.g, from about 1.0:0.2, from about 1.0:0.3, or from about 1.0:0.4.

In certain embodiments, the ratio of the base of each of the one or more ridges to the height of each of the one or more ridges to the width of the peak of the one or more ridges is about 1:0.75:0.5.

In certain embodiments, a channel as described herein is provided with a plurality of ridges which extend for a distance along the channel wall. This distance may be, for example, from about 50 microns to about 500 microns, e.g., from about 50 microns to about 450 microns, from about 100 microns to about 400 microns, from about 150 microns to about 350 microns, from about 200 microns to about 300 microns, or about 250 microns. In certain embodiments, a plurality of ridges may be provided which extend for a distance along the channel wall, wherein the ratio between the distance along the channel wall and the width of the channel is from about 10:1 to about 1:2, e.g., about 10:1, about 9:1, about 8:1, about 7:1, about 6:1 about 5:1, about 4:1, about 3:1, about 2:1, about 1:1, or about 1:2.

It should be noted that one or more of the various dimensions discussed above may be scaled up or down as appropriate for a particular application, for example each of the above dimensions may be scaled up or down by a factor of 2, 5, 10 or more as appropriate.

In some embodiments, one or more channel junctions, e.g., one or more droplet forming junctions, such as a picoinjector junction, include a "step-down" structure, wherein the portion of the flow channel at the picoinjector junction and downstream of the picoinjector junction is wider than the portion of the flow channel upstream of the picoinjector junction. This step-down structure facilitates the pinching-off of droplets and thus facilitates droplet formation. The step size may be chosen based on the desired size of the droplet to be formed, with larger steps creating larger droplets. Such structures may also help to avoid dripping of material from the picoinjector following injection from the picoinjector into a droplet. In some embodiments, the width of the flow channel at the picoinjector junction and downstream of the picoinjector junction is from about 5% to about 50% wider than the width of the flow channel immediately upstream of the picoinjector junction, e.g., about 5 to about 10% wider, about 10 to about 20% wider, about 20 to about 30% wider, about 30 to about 40% wider or about 40 to about 50% wider.

In some embodiments, one or more channel junctions, e.g., one or more droplet forming junctions, are treated with oxygen plasma. This treatment will transiently change the natural hydrophobicity of PDMS, facilitating the pinching off of water-in-oil droplets by an aqueous phase, thus facilitating double emulsion droplet formation. Modification can be made "permanent" through use of solvent extraction as described by Vickers, et al., Anal. Chem, 2006, 78 (21), pp 7446-7452.

In some embodiments, a coaxial flow-focusing device may be utilized to prepare double emulsions suitable for use in connection with the methods described herein. The device may include a channel which is, e.g., approximately 50 μm tall, into which single emulsion drops are introduced as a close pack; close packing minimizes interstitial oil, allowing the formation of thin-shelled double emulsions. The double emulsification junction includes a channel taller and wider than the single emulsion channel; aqueous carrier fluid is introduced into the Y-shaped channel, as shown in FIGS. 8-11. The single emulsion channel is centered horizontally and vertically in the carrier phase channel; when the aqueous carrier phase is introduced at a sufficient velocity, this geometry ensures that the oil encapsulating the single emulsion lifts from the walls, forming a "cone" suspended in the flowing aqueous phase, as shown in FIG. 8-11. This nonplanar geometry allows for the formation of double emulsions in a device that is uniformly hydrophobic.

Figure 8:
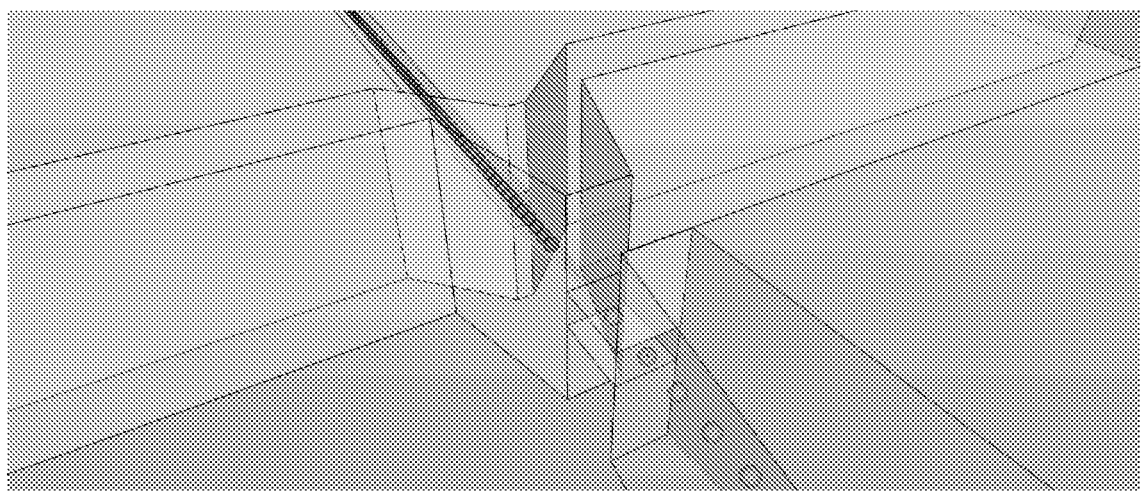
FIG. 8 provides two different views of a three dimensional schematic showing a device which may be used to encapsulate single emulsions in double emulsions. It includes a channel in which the single emulsions, e.g., water in oil droplets, are introduced, which channel opens up into a large channel in which additional miscible phase fluid is added. This focuses the injected drops through an orifice, causing them to be encapsulated in an immiscible phase droplet and forming double emulsions, e.g., water-in-oil-in-water double emulsions.
Figure 8:
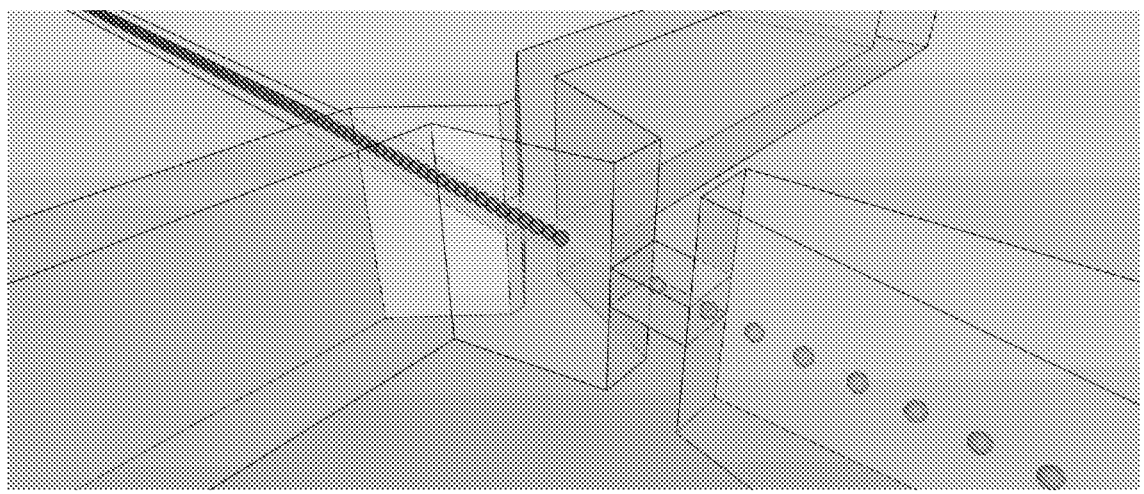
Figure 9:
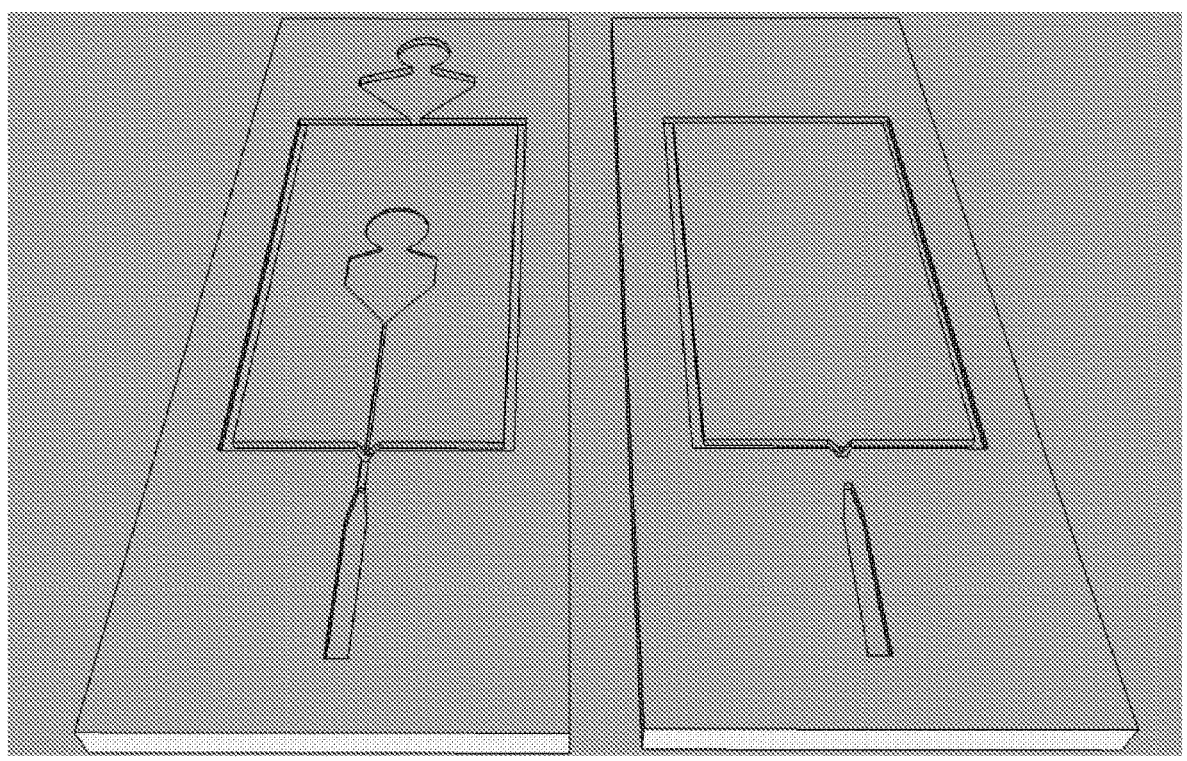
FIG. 9 provides two schematics of PDMS slabs that may be used to construct a double emulsification device. The slab on the left has channels with two heights—short channels for the droplet reinjection and constriction channels (see previous Figure) and tall channels for the aqueous phase and outlets. The slab on the right has only the tall channels. To complete the device, the slabs are aligned and sealed together so that the channels are facing. The devices are bonded using plasma oxidation.
Figure 10:
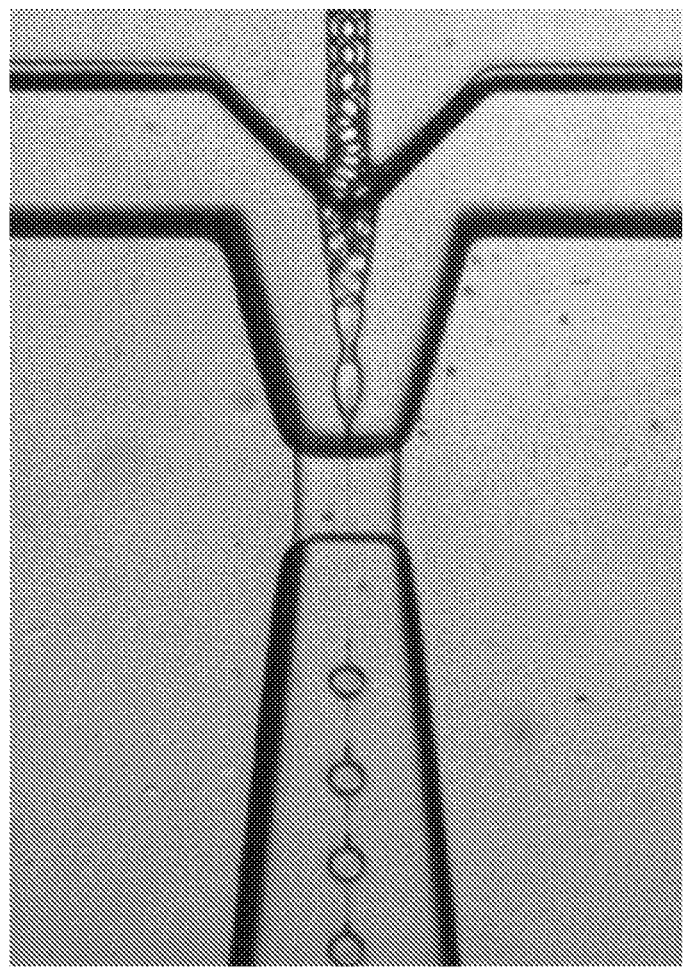
FIG. 10 provides a microscope image of a double emulsification device encapsulating reinjected single emulsions in double emulsions. The reinjected single emulsions enter from above and are encapsulated in the constriction shown in the center of the device. They then exit as double emulsions, four of which are shown towards the bottom of the device.

Downstream of the cone is a constriction centered vertically and horizontally in the channel, as shown in the schematic of FIG. 8. This feature allows for the formation of thin-shelled double emulsions with just one core: as the cone extends into the constriction, it is hydrodynamically focused by the rushing carrier phase; this generates sufficient shear to rip individual drops from the tip of the cone, as illustrated in FIG. 8. Without the constriction, the double emulsions would likely contain multiple cores.

Generating single emulsion microdroplets or multiple-emulsion microdroplets and/or GUVs with microfluidic devices often involves the use of one or more pumps to inject the requisite solutions into the device at the needed flow rates. Pumps are bulky, require power, and may need to be integrated together, often with a controller, to drive correct flow rates. In some instances, it may be desirable to generate droplets without the use of pumps, particularly double emulsions. For example, using methods described herein, it is possible to generate single or multiple emulsions, including double emulsions, without the use of pumps.

In some such embodiments, a device may be fabricated that has channel dimensions set such that fluid flow rate through them, for a specific pressure, is controlled. For example, if it is desirable to flow a particular fluid more slowly through a channel, then the channel can be lengthened or narrowed, increasing its hydrodynamic resistance so that, for the same pressure drop through the channel, the flow rate is reduced. Due to the strong dependence of hydrodynamic resistance on channel diameter (~D^−4) and channel length (~L), it is possible to modulate flow rate over a wide range for constant pressure drop using geometrical control of channel dimensions. This can then be combined with a method for generating a pressure drop across the device channels such as, for example, by pressurizing the inlets with respect to the outlets using an air pressure pump or reservoir with compressed air. Alternatively, the outlet pressure may be reduced via application of a vacuum, generating a pressure drop from the inlet to the outlet.

Another way to generate a pressure drop is using gravitational potential energy. For example, one method is to increase the heights of the fluids at the inlets of the device compared to the outlets. Other double emulsion forming geometries can also be used, such as glass capillary geometries, two-step and one-step formation with wettability patterning, and even geometries configured for the generation of higher order multiple emulsions.

Methods of Fabrication

Microfabrication processes differ depending on the type of materials used in the substrate and the desired production volume. For small volume production or prototypes, fabrication techniques include LIGA, powder blasting, laser ablation, mechanical machining, electrical discharge machining, photoforming, etc. Technologies for mass production of microfluidic devices may use either lithographic or master-based replication processes. Lithographic processes for fabricating substrates from silicon/glass include both wet and dry etching techniques commonly used in fabrication of semiconductor devices. Injection molding and hot embossing typically are used for mass production of plastic substrates.

Glass, Silicon and Other "Hard" Materials (Lithography, Etching, Deposition)

The combination of lithography, etching and deposition techniques may be used to make microcanals and microcavities out of glass, silicon and other "hard" materials. Technologies based on the above techniques are commonly applied in for fabrication of devices in the scale of 0.1-500 micrometers.

Microfabrication techniques based on current semiconductor fabrication processes are generally carried out in a clean room. The quality of the clean room is classified by the number of particles <4 μm in size in a cubic inch. Typical clean room classes for MEMS microfabrication are 1000 to 10000.

In certain embodiments, photolithography may be used in microfabrication. In photolithography, a photoresist that has been deposited on a substrate is exposed to a light source through an optical mask. Conventional photoresist methods allow structural heights of up to 10-40 μm. If higher structures are needed, thicker photoresists such as SU-8, or polyimide, which results in heights of up to 1 mm, can be used.

After transferring the pattern on the mask to the photoresist-covered substrate, the substrate is then etched using either a wet or dry process. In wet etching, the substrate—area not protected by the mask—is subjected to chemical attack in the liquid phase. The liquid reagent used in the etching process depends on whether the etching is isotropic or anisotropic. Isotropic etching generally uses an acid to form three-dimensional structures such as spherical cavities in glass or silicon. Anisotropic etching forms flat surfaces such as wells and canals using a highly basic solvent. Wet anisotropic etching on silicon creates an oblique channel profile.

Dry etching involves attacking the substrate by ions in either a gaseous or plasma phase. Dry etching techniques can be used to create rectangular channel cross-sections and arbitrary channel pathways. Various types of dry etching that may be employed including physical, chemical, physico-chemical (e.g., RIE), and physico-chemical with inhibitor. Physical etching uses ions accelerated through an electric field to bombard the substrate's surface to "etch" the structures. Chemical etching may employ an electric field to migrate chemical species to the substrate's surface. The chemical species then reacts with the substrate's surface to produce voids and a volatile species.

In certain embodiments, deposition is used in microfabrication. Deposition techniques can be used to create layers of metals, insulators, semiconductors, polymers, proteins and other organic substances. Most deposition techniques fall into one of two main categories: physical vapor deposition (PVD) and chemical vapor deposition (CVD). In one approach to PVD, a substrate target is contacted with a holding gas (which may be produced by evaporation for example). Certain species in the gas adsorb to the target's surface, forming a layer constituting the deposit. In another approach commonly used in the microelectronics fabrication industry, a target containing the material to be deposited is sputtered with using an argon ion beam or other appropriately energetic source. The sputtered material then deposits on the surface of the microfluidic device. In CVD, species in contact with the target react with the surface, forming components that are chemically bonded to the object. Other deposition techniques include: spin coating, plasma spraying, plasma polymerization, dip coating, casting and Langmuir-Blodgett film deposition. In plasma spraying, a fine powder containing particles of up to 100 μm in diameter is suspended in a carrier gas. The mixture containing the particles is accelerated through a plasma jet and heated. Molten particles splatter onto a substrate and freeze to form a dense coating. Plasma polymerization produces polymer films (e.g. PMMA) from plasma containing organic vapors.

Once the microchannels, microcavities and other features have been etched into the glass or silicon substrate, the etched features are usually sealed to ensure that the microfluidic device is "watertight." When sealing, adhesion can be applied on all surfaces brought into contact with one another. The sealing process may involve fusion techniques such as those developed for bonding between glass-silicon, glass-glass, or silicon-silicon.

Anodic bonding can be used for bonding glass to silicon. A voltage is applied between the glass and silicon and the temperature of the system is elevated to induce the sealing of the surfaces. The electric field and elevated temperature induces the migration of sodium ions in the glass to the glass-silicon interface. The sodium ions in the glass-silicon interface are highly reactive with the silicon surface forming a solid chemical bond between the surfaces. The type of glass used should ideally have a thermal expansion coefficient near that of silicon (e.g. Pyrex Corning 7740).

Fusion bonding can be used for glass-glass or silicon-silicon sealing. The substrates are first forced and aligned together by applying a high contact force. Once in contact, atomic attraction forces (primarily van der Waals forces) hold the substrates together so they can be placed into a furnace and annealed at high temperatures. Depending on the material, temperatures used ranges between about 600 and 1100° C.

Polymers/Plastics

A number of techniques may be employed for micromachining plastic substrates in accordance with embodiments of this invention. Among these are laser ablation, stereolithography, oxygen plasma etching, particle jet ablation, and microelectro-erosion. Some of these techniques can be used to shape other materials (glass, silicon, ceramics, etc.) as well.

To produce multiple copies of a microfluidic device, replication techniques are employed. Such techniques involve first fabricating a master or mold insert containing the pattern to be replicated. The master is then used to mass-produce polymer substrates through polymer replication processes.

In the replication process, the master pattern contained in a mold is replicated onto the polymer structure. In certain embodiments, a polymer and curing agent mix is poured onto a mold under high temperatures. After cooling the mix, the polymer contains the pattern of the mold, and is then removed from the mold. Alternatively, the plastic can be injected into a structure containing a mold insert. In micro-injection, plastic heated to a liquid state is injected into a mold. After separation and cooling, the plastic retains the mold's shape.

PDMS (polydimethylsiloxane), a silicon-based organic polymer, may be employed in the molding process to form microfluidic structures. Because of its elastic character, PDMS is well suited for microchannels between about 5 and 500 μm. Specific properties of PDMS make it particularly suitable for microfluidic purposes:

1) It is optically clear which allows for visualization of the flows;
2) PDMS when mixed with a proper amount of reticulating agent has elastomeric qualities that facilitates keeping microfluidic connections "watertight;"
3) Valves and pumps using membranes can be made with PDMS because of its elasticity;
4) Untreated PDMS is hydrophobic, and becomes temporarily hydrophilic after oxidation of surface by oxygen plasma or after immersion in strong base; oxidized PDMS adheres by itself to glass, silicon, or polyethylene, as long as those surfaces were themselves exposed to an oxygen plasma.
5) PDMS is permeable to gas. Filling of the channel with liquids is facilitated even when there are air bubbles in the canal because the air bubbles are forced out of the material. But it's also permeable to non polar-organic solvents.

Microinjection can be used to form plastic substrates employed in a wide range of microfluidic designs. In this process, a liquid plastic material is first injected into a mold under vacuum and pressure, at a temperature greater than the glass transition temperature of the plastic. The plastic is then cooled below the glass transition temperature. After removing the mold, the resulting plastic structure is the negative of the mold's pattern.

Yet another replicating technique is hot embossing, in which a polymer substrate and a master are heated above the polymer's glass transition temperature, Tg (which for PMMA or PC is around 100-180° C.). The embossing master is then pressed against the substrate with a preset compression force. The system is then cooled below Tg and the mold and substrate are then separated.

Typically, the polymer is subjected to the highest physical forces upon separation from the mold tool, particularly when the microstructure contains high aspect ratios and vertical walls. To avoid damage to the polymer microstructure, material properties of the substrate and the mold tool may be taken into consideration. These properties include: sidewall roughness, sidewall angles, chemical interface between embossing master and substrate and temperature coefficients. High sidewall roughness of the embossing tool can damage the polymer microstructure since roughness contributes to frictional forces between the tool and the structure during the separation process. The microstructure may be destroyed if frictional forces are larger than the local tensile strength of the polymer. Friction between the tool and the substrate may be important in microstructures with vertical walls. The chemical interface between the master and substrate could also be of concern. Because the embossing process subjects the system to elevated temperatures, chemical bonds could form in the master-substrate interface. These interfacial bonds could interfere with the separation process. Differences in the thermal expansion coefficients of the tool and the substrate could create addition frictional forces.

Various techniques can be employed to form molds, embossing masters, and other masters containing patterns used to replicate plastic structures through the replication processes mentioned above. Examples of such techniques include LIGA (described below), ablation techniques, and various other mechanical machining techniques. Similar techniques can also be used for creating masks, prototypes and microfluidic structures in small volumes. Materials used for the mold tool include metals, metal alloys, silicon and other hard materials.

Laser ablation may be employed to form microstructures either directly on the substrate or through the use of a mask. This technique uses a precision-guided laser, typically with wavelength between infrared and ultraviolet. Laser ablation may be performed on glass and metal substrates, as well as on polymer substrates. Laser ablation can be performed either through moving the substrate surface relative to a fixed laser beam, or moving the beam relative to a fixed substrate. Various micro-wells, canals, and high aspect structures can be made with laser ablation.

Certain materials such as stainless steel make very durable mold inserts and can be micromachined to form structures down to the 10-μm range. Various other micromachining techniques for microfabrication exist including μ-Electro Discharge Machining (μ-EDM), μ-milling, focused ion beam milling. μ-EDM allows the fabrication of 3-dimensional structures in conducting materials. In μ-EDM, material is removed by high-frequency electric discharge generated between an electrode (cathode tool) and a workpiece (anode). Both the workpiece and the tool are submerged in a dielectric fluid. This technique produces a comparatively rougher surface but offers flexibility in terms of materials and geometries.

Electroplating may be employed for making a replication mold tool/master out of, e.g., a nickel alloy. The process starts with a photolithography step where a photoresist is used to defined structures for electroplating. Areas to be electroplated are free of resist. For structures with high aspect ratios and low roughness requirements, LIGA can be used to produce electroplating forms. LIGA is a German acronym for Lithographic (Lithography), Galvanoformung (electroplating), Abformung (molding). In one approach to LIGA, thick PMMA layers are exposed to x-rays from a synchrotron source. Surfaces created by LIGA have low roughness (around 10 nm RMS) and the resulting nickel tool has good surface chemistry for most polymers.

As with glass and silicon devices, polymeric microfluidic devices must be closed up before they can become functional. Common problems in the bonding process for microfluidic devices include the blocking of channels and changes in the physical parameters of the channels. Lamination is one method used to seal plastic microfluidic devices. In one lamination process, a PET foil (about 30 µm) coated with a melting adhesive layer (typically 5-10 µm) is rolled with a heated roller, onto the microstructure. Through this process, the lid foil is sealed onto the channel plate. Several research groups have reported a bonding by polymerization at interfaces, whereby the structures are heated and force is applied on opposite sides to close the channel. But excessive force applied may damage the microstructures. Both reversible and irreversible bonding techniques exist for plastic-plastic and plastic-glass interfaces. One method of reversible sealing involves first thoroughly rinsing a PDMS substrate and a glass plate (or a second piece of PDMS) with methanol and bringing the surfaces into contact with one another prior to drying. The microstructure is then dried in an oven at 65° C. for 10 min. No clean room is required for this process. Irreversible sealing is accomplished by first thoroughly rinsing the pieces with methanol and then drying them separately with a nitrogen stream. The two pieces are then placed in an air plasma cleaner and oxidized at high power for about 45 seconds. The substrates are then brought into contact with each other and an irreversible seal forms spontaneously.

Other available techniques include laser and ultrasonic welding. In laser welding, polymers are joined together through laser-generated heat. This method has been used in the fabrication of micropumps. Ultrasonic welding is another bonding technique that may be employed in some applications.

It should be noted that while the nucleic acid amplification techniques described herein are frequently described with reference to polymerase chain reaction (PCR) amplification techniques, such description is not intended to be limiting. In certain embodiments, non-PCR amplification techniques may be employed such as various isothermal nucleic acid amplification techniques; e.g., real-time strand displacement amplification (SDA), rolling-circle amplification (RCA) and multiple-displacement amplification (MDA). Accordingly, wherever technically feasible, one or more suitable non-PCR amplification techniques, e.g., one or more isothermal nucleic acid amplification techniques, may be substituted for one or more of the PCR amplification techniques described herein.

Regarding PCR amplification modules, it will be necessary to provide to such modules at least the building blocks for amplifying nucleic acids (e.g., ample concentrations of four nucleotides), primers, polymerase (e.g., Taq), and appropriate temperature control programs). The polymerase and nucleotide building blocks may be provided in a buffer solution provided via an external port to the amplification module or from an upstream source. In certain embodiments, the buffer stream provided to the sorting module contains some of all the raw materials for nucleic acid amplification. For PCR in particular, precise temperature control of the reacting mixture is extremely important in order to achieve high reaction efficiency. One method of on-chip thermal control is Joule heating in which electrodes are used to heat the fluid inside the module at defined locations. The fluid conductivity may be used as a temperature feedback for power control.

In certain aspects, the single emulsion microdroplets or multiple-emulsion microdroplets and/or GUVs containing the PCR mix may be flowed through a channel that incubates the droplets under conditions effective for PCR. Flowing the microdroplets through a channel may involve a channel that snakes over various temperature zones maintained at temperatures effective for PCR. Such channels may, for example, cycle over two or more temperature zones, wherein at least one zone is maintained at about 65° C. and at least one zone is maintained at about 95° C. As the microdroplets move through such zones, their temperature cycles, as needed for PCR. The precise number of zones, and the respective temperature of each zone, may be readily determined by those of skill in the art to achieve the desired PCR amplification.

In other embodiments, incubating the single emulsion microdroplets or multiple-emulsion microdroplets and/or GUVs may involve the use of a Megadroplet Array. In such a device, an array consists of channels in which the channel ceilings are indented with millions of circular traps that are about 25 µm in diameter. Single emulsion microdroplets or multiple-emulsion microdroplets and/or GUVs are distributed into the trapping channels using distribution plates—large channels connecting the inlets of the trapping channels. Due to the large size of the distribution channels compared to the trapping channels—the distribution channels are about 100×500 µm in height and width, compared to only about 15×100 µm for the single emulsion microdroplets or multiple-emulsion microdroplets and/or GUVs trapping channels—the hydrodynamic resistance of the distribution channels is ~1500 times lower than that of the trapping channels; this ensures that the distribution channel fills with single emulsion microdroplets or multiple-emulsion microdroplets and/or GUVs before the trapping channels begin to fill, allowing even distribution of the single emulsion microdroplets or multiple-emulsion microdroplets and/or GUVs into the trapping channels. When the drops flow into the trapping channels, they are slightly pancaked in shape because the vertical height of the channel is 15 µm, or 10 µm shorter than the drops. When a single emulsion microdroplet or multiple-emulsion microdroplet and/or GUV nears a trap, its interface adopts a larger, more energetically favorable radius of curvature. To minimize its surface energy, the single emulsion microdroplet or multiple-emulsion microdroplet and/or GUV entirely fills the trap, allowing it to adopt the lowest, most energetically favorable, average radius of curvature. After a trap is occupied by a single emulsion microdroplet or multiple-emulsion microdroplet and/or GUV, no other single emulsion microdroplet or multiple-emulsion microdroplets and/or GUVs are able to enter because the trap is large enough to fit only one single emulsion microdroplet or multiple-emulsion microdroplet and/or GUVs; additional single emulsion microdroplet or multiple-emulsion microdroplets and/or GUVs are diverted downstream, to occupy the first vacant trap they encounter. Because the array is filled using a close-packed emulsion, every trap will be occupied by a multiple-emulsion microdroplet and/or GUV, since this is the most energetically favorable state under low flow conditions. After the droplet array is filled, oil is injected to remove excess drops and the array is thermal cycled and imaged.

A variety of different ways can be used to fill the traps of the device. For instance, buoyancy effects and centrifugation can also be used to fill and empty the traps by flipping the device with respect to the earth's gravitational field, since the droplet density is 63% that of the fluorocarbon carrier oil. That is, if the single emulsion microdroplets or multiple-emulsion microdroplets and/or GUVs were heavier than the oil phase, then the wells could be imprinted into the "floor" of the device so that when the emulsion was flowed over it, the single emulsion microdroplets or multiple-emulsion microdroplets and/or GUVs would sink into the wells. The flow rate of the emulsion could be adjusted to optimize this and the drop size would be made to be approximately the same size as the well so that the well could only fit a single drop at a time. In other aspects, the single emulsion microdroplets or multiple-emulsion microdroplets and/or GUVs could also, or instead, be stored in a large chamber with no wells.

The device may achieve thermal cycling using a heater consisting of a Peltier plate, heat sink, and control computer. The Peltier plate allows heating and/or cooling the chip above or below room temperature by controlling the applied current. To ensure controlled and reproducible temperature, a computer monitors the temperature of the array using integrated temperature probes, and adjusts the applied current to heat and cool as needed. A metallic (e.g., copper) plate allows uniform application of heat and dissipation of excess heat during cooling cycles, enabling cooling from 95° C. to 60° C. in under 1 min execution. In order to image microdroplets, certain embodiments may incorporate a scanner bed. In certain aspects, the scanner bed is a Canoscan 9000F scanner bed.

In order to effectively amplify nucleic acids from target components, the microfluidics system may include a cell lysing or viral protein coat-disrupting module to free nucleic acids prior to providing the sample to an amplification module. Cell lysing modules may rely on chemical, thermal, and/or mechanical means to effect cell lysis. Because the cell membrane consists of a lipid double-layer, lysis buffers containing surfactants can solubilize the lipid membranes. Typically, the lysis buffer will be introduced directly to a lysis chamber via an external port so that the cells are not prematurely lysed during sorting or other upstream process. In cases where organelle integrity is necessary, chemical lysis methods may be inappropriate. Mechanical breakdown of the cell membrane by shear and wear is appropriate in certain applications. Lysis modules relying mechanical techniques may employ various geometric features to effect piercing, shearing, abrading, etc. of cells entering the module. Other types of mechanical breakage such as acoustic techniques may also yield appropriate lysate. Further, thermal energy can also be used to lyse cells such as bacteria, yeasts, and spores. Heating disrupts the cell membrane and the intracellular materials are released. In order to enable subcellular fractionation in microfluidic systems a lysis module may also employ an electrokinetic technique or electroporation. Electroporation creates transient or permanent holes in the cell membranes by application of an external electric field that induces changes in the plasma membrane and disrupts the transmembrane potential. In microfluidic electroporation devices, the membrane may be permanently disrupted, and holes on the cell membranes sustained to release desired intracellular materials released.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-81 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A nucleic acid amplification method including:
   encapsulating a nucleic acid and amplification reagents in a multiple-emulsion microdroplet, the multiple-emulsion microdroplet including a first miscible phase fluid surrounded by an immiscible shell, wherein the multiple-emulsion microdroplet is positioned in a second miscible phase carrier fluid; and
   subjecting the multiple-emulsion microdroplet to amplification conditions sufficient to result in amplification of the nucleic acid; and
   detecting an amplification product resulting from the amplification of the nucleic acid.
2. The method of 1, wherein the second miscible phase carrier fluid is a buffered aqueous phase carrier fluid.
3. The method of 1, wherein the first and second miscible phase fluids are the same.
4. The method of any one of 1-3, wherein subjecting the multiple-emulsion microdroplet to amplification conditions includes subjecting the multiple-emulsion microdroplet to polymerase chain reaction (PCR) conditions.
5. The method of any one of 1-3, wherein subjecting the multiple-emulsion microdroplet to amplification conditions includes subjecting the multiple-emulsion microdroplet to isothermal amplification conditions.
6. The method of 5, wherein the isothermal amplification conditions are selected from loop-mediated isothermal amplification (LAMP), strand displacement amplification (SDA), helicase-dependent amplification (HDA), and nicking enzyme amplification reaction (NEAR).
7. The method of any one of 1-6, including detectably labeling the amplification product subsequent to amplification.
8. The method of any one of 1-6, wherein the amplification reagents include detectably labeled primers and/or probes.
9. The method of any one of 1-8, including detectably labeling the amplification product with a fluorescent label and sorting the multiple-emulsion microdroplet via fluorescence activating cell sorting (FACS).
10. The method of any one of 1-9, including adjusting the composition of the first miscible phase fluid by adjusting the composition of the second miscible phase fluid.
11. The method of any one of 1-10, including detectably labeling the amplification product by adding a detectable label to the second miscible phase carrier fluid, wherein the detectable label diffuses from the second miscible phase carrier fluid, through the immiscible shell, and into the first miscible phase fluid.
12. The method of any one of 1-11, wherein the multiple-emulsion microdroplet is a second multiple-emulsion microdroplet and the encapsulating includes encapsulating the nucleic acid in a first multiple-emulsion microdroplet, encapsulating the amplification reagents and the first multiple-emulsion microdroplet in the second-multiple emulsion microdroplet, and rupturing the first multiple-emulsion microdroplet thereby bringing the nucleic acid into contact with the amplification reagents.

13. The method of any one of 1-11, wherein the multiple-emulsion microdroplet is a second multiple-emulsion microdroplet and the encapsulating includes encapsulating the amplification reagents in a first multiple-emulsion microdroplet, encapsulating the nucleic acid and the first multiple-emulsion microdroplet in the second-multiple emulsion microdroplet, and rupturing the first multiple-emulsion microdroplet thereby bringing the nucleic acid into contact with the amplification reagents.
14. The method of any one of 1-11, wherein the multiple-emulsion microdroplet is a first multiple-emulsion microdroplet, and the method includes adding a reagent to the first multiple-emulsion microdroplet, wherein the adding includes encapsulating the first multiple-emulsion microdroplet in a second multiple-emulsion microdroplet including the reagent and rupturing the first multiple-emulsion microdroplet within the second multiple-emulsion microdroplet to bring the reagent into contact with the contents of the first multiple-emulsion microdroplet.
15. The method of any one of 1-11, wherein the multiple-emulsion microdroplet is a second multiple-emulsion microdroplet, and the method includes adding a reagent to the second multiple-emulsion microdroplet, wherein the adding includes encapsulating a first multiple-emulsion microdroplet including the reagent in the second multiple-emulsion microdroplet and rupturing the first multiple-emulsion microdroplet within the second multiple-emulsion microdroplet to bring the reagent into contact with the contents of the second multiple-emulsion microdroplet.
16. A nucleic acid amplification method including:
    encapsulating a plurality of nucleic acids suspected of containing a target nucleic
    acid with amplification reagents in a plurality of multiple-emulsion microdroplets, such that each multiple-emulsion microdroplet includes amplification reagents and zero or one nucleic acid encapsulated therein, wherein each multiple-emulsion microdroplet includes a first miscible phase fluid surrounded by an immiscible shell, and wherein each multiple-emulsion microdroplet is positioned in a second miscible phase carrier fluid; and
    subjecting the multiple-emulsion microdroplets to amplification conditions sufficient to result in amplification of the target nucleic acid when present; and
    detecting an amplification product resulting from the amplification of the target nucleic acid when present.
17. The method of 16, wherein the second miscible phase carrier fluid is a buffered aqueous phase carrier fluid.
18. The method of 16, wherein the first and second miscible phase fluids are the same.
19. The method of any one of 16-18, wherein subjecting the multiple-emulsion microdroplets to amplification conditions includes subjecting the multiple-emulsion microdroplets to polymerase chain reaction (PCR) conditions.
20. The method of any one of 16-18, wherein subjecting the multiple-emulsion microdroplets to amplification conditions includes subjecting the multiple-emulsion microdroplets to isothermal amplification conditions.
21. The method of 20, wherein the isothermal amplification conditions are selected from loop-mediated isothermal amplification (LAMP), strand displacement amplification (SDA), helicase-dependent amplification (HDA), and nicking enzyme amplification reaction (NEAR).
22. The method of any one of 16-21, including detectably labeling the amplification product when present subsequent to amplification.
23. The method of any one of 16-21, wherein the amplification reagents include detectably labeled primers and/or probes.
24. The method of any one of 16-23, including detectably labeling the amplification product when present with a fluorescent label and sorting the multiple-emulsion microdroplets via fluorescence activating cell sorting (FACS) to identify multiple-emulsion microdroplets containing the target nucleic acid when present.
25. The method of any one of 16-24, including adjusting the composition of the first miscible phase fluid by adjusting the composition of the second miscible phase carrier fluid.
26. The method of any one of 16-25, including detectably labeling the amplification product when present by adding a detectable label to the second miscible phase carrier fluid, wherein the detectable label diffuses from the second miscible phase carrier fluid, through the immiscible shell, and into the first miscible phase fluid.
27. The method of any one of 16-26, wherein the multiple-emulsion microdroplets are second multiple-emulsion microdroplets and the encapsulating includes encapsulating the plurality of nucleic acids in a plurality of first multiple-emulsion microdroplets, encapsulating the amplification reagents and the first multiple-emulsion microdroplets in the second-multiple emulsion microdroplets, and rupturing the first multiple-emulsion microdroplets in the second multiple-emulsion microdroplets thereby bringing the nucleic acids into contact with the amplification reagents.
28. The method of any one of 16-26, wherein the multiple-emulsion microdroplets are second multiple-emulsion microdroplets and the encapsulating includes encapsulating the amplification reagents in first multiple-emulsion microdroplets, encapsulating the plurality of nucleic acids and the first multiple-emulsion microdroplets in the second-multiple emulsion microdroplets, and rupturing the first multiple-emulsion microdroplets in the second multiple-emulsion microdroplets thereby bringing the nucleic acids into contact with the amplification reagents.
29. The method of any one of 16-26, wherein the multiple-emulsion microdroplets are first multiple-emulsion microdroplets, and the method includes adding a reagent to the first multiple-emulsion microdroplets, wherein the adding includes encapsulating the first multiple-emulsion microdroplets in second multiple-emulsion microdroplets including the reagent and rupturing the first multiple-emulsion microdroplets within the second multiple-emulsion microdroplets to bring the reagent into contact with the contents of the first multiple-emulsion microdroplets.
30. The method of any one of 16-26, wherein the multiple-emulsion microdroplets are second multiple-emulsion microdroplets, and the method includes adding a reagent to the second multiple-emulsion microdroplets, wherein the adding includes encapsulating first multiple-emulsion microdroplets including the reagent in the second multiple-emulsion microdroplets and rupturing the first multiple-emulsion microdroplets within the second multiple-emulsion microdroplets to bring the reagent into contact with the contents of the second multiple-emulsion microdroplets.

31. A nucleic acid amplification method including:
    flowing a miscible phase fluid solution of nucleic acids and amplification reagents in a channel of a microfluidic device;
    contacting the miscible phase fluid solution of nucleic acids and amplification reagents with an immiscible phase fluid, wherein the contacting of the miscible phase fluid solution of nucleic acids and amplification reagents with the immiscible phase fluid results in the formation of miscible phase microdroplets surrounded by the immiscible phase fluid;
    flowing the miscible phase microdroplets surrounded by the immiscible phase fluid in a channel of a microfluidic device;
    contacting the miscible phase microdroplets surrounded by the immiscible phase fluid with a miscible phase carrier fluid, wherein the contacting of the miscible phase microdroplets surrounded by the immiscible phase fluid with the miscible phase carrier fluid results in the formation of multiple-emulsion microdroplets, each multiple-emulsion microdroplet including a miscible phase microdroplet surrounded by the immiscible phase fluid, wherein the immiscible phase fluid is surrounded by the miscible phase carrier fluid;
    subjecting the multiple-emulsion microdroplets to amplification conditions sufficient to result in amplification of a target nucleic acid when present in the miscible phase fluid solution of nucleic acids; and
    detecting an amplification product resulting from the amplification of the target nucleic acid when present in the miscible phase fluid solution of nucleic acids.
32. The method of 31, wherein the miscible phase carrier fluid is a buffered aqueous phase carrier fluid.
33. The method of 31, wherein the miscible phase fluid of the miscible phase fluid solution and the miscible phase carrier fluid are the same.
34. The method of any one of 31-33, wherein subjecting the multiple-emulsion microdroplets to amplification conditions includes subjecting the multiple-emulsion microdroplets to polymerase chain reaction (PCR) conditions.
35. The method of any one of 31-33, wherein subjecting the multiple-emulsion microdroplets to amplification conditions includes subjecting the multiple-emulsion microdroplets to isothermal amplification conditions.
36. The method of 35, wherein the isothermal amplification conditions are selected from loop-mediated isothermal amplification (LAMP), strand displacement amplification (SDA), helicase-dependent amplification (HDA), and nicking enzyme amplification reaction (NEAR).
37. The method of any one of 31-36, including detectably labeling the amplification product subsequent to amplification.
38. The method of any one of 31-36, wherein the amplification reagents include detectably labeled primers and/or probes.
39. The method of any one of 31-38, including detectably labeling the amplification product with a fluorescent label and sorting the multiple-emulsion microdroplets via fluorescence activating cell sorting (FACS).
40. The method of any one of 31-39, including adjusting the composition of the miscible phase fluid solution by adjusting the composition of the miscible phase carrier fluid.
41. The method of any one of 31-40, including detectably labeling the amplification product by adding a detectable label to the miscible phase carrier fluid, wherein the detectable label diffuses from the miscible phase carrier fluid, through the immiscible phase fluid, and into the miscible phase fluid solution.
42. The method of any one of 31-41, wherein the multiple-emulsion microdroplets are first multiple-emulsion microdroplets, and the method includes adding a reagent to the first multiple-emulsion microdroplets, wherein the adding includes encapsulating the first multiple-emulsion microdroplets in second multiple-emulsion microdroplets including the reagent and rupturing the first multiple-emulsion microdroplets within the second multiple-emulsion microdroplets to bring the reagent into contact with the contents of the first multiple-emulsion microdroplets.
43. The method of any one of 31-41, wherein the multiple-emulsion microdroplets are second multiple-emulsion microdroplets, and the method includes adding a reagent to the second multiple-emulsion microdroplets, wherein the adding includes encapsulating first multiple-emulsion microdroplets including the reagent in the second multiple-emulsion microdroplets and rupturing the first multiple-emulsion microdroplets within the second multiple-emulsion microdroplets to bring the reagent into contact with the contents of the second multiple-emulsion microdroplets.
44. A nucleic acid amplification method including:
    flowing a miscible phase fluid solution of nucleic acids and amplification reagents in a channel of a microfluidic device;
    contacting the miscible phase fluid solution of nucleic acids and amplification reagents with an immiscible phase fluid, wherein the contacting of the miscible phase fluid solution of nucleic acids and amplification reagents with the immiscible phase fluid results in the formation of miscible phase microdroplets surrounded by the immiscible phase fluid, wherein each miscible phase microdroplet includes amplification reagents and zero or one nucleic acid encapsulated therein;
    flowing the miscible phase microdroplets surrounded by the immiscible phase fluid in a channel of a microfluidic device;
    contacting the miscible phase microdroplets surrounded by the immiscible phase fluid with a miscible phase carrier fluid, wherein the contacting of the miscible phase microdroplets surrounded by the immiscible phase fluid with the miscible phase carrier fluid results in the formation of multiple-emulsion microdroplets, each multiple-emulsion microdroplet including a miscible phase microdroplet surrounded by the immiscible phase fluid, wherein the immiscible phase fluid is surrounded by the miscible phase carrier fluid;
    subjecting the multiple-emulsion microdroplets to amplification conditions sufficient to result in amplification of a target nucleic acid when present in the miscible phase solution of nucleic acids; and detecting an amplification product resulting from the amplification of the target nucleic acid when present in the miscible phase solution of nucleic acids.

45. The method of 44, wherein the miscible phase carrier fluid is a buffered aqueous phase carrier fluid.

46. The method of 44, wherein the miscible phase fluid of the miscible phase fluid solution and the miscible phase carrier fluid are the same.

47. The method of any one of 44-46, wherein subjecting the multiple-emulsion microdroplets to amplification conditions includes subjecting the multiple-emulsion microdroplets to polymerase chain reaction (PCR) conditions.

48. The method of any one of 44-46, wherein subjecting the multiple-emulsion microdroplets to amplification conditions includes subjecting the multiple-emulsion microdroplets to isothermal amplification conditions.

49. The method of 48, wherein the isothermal amplification conditions are selected from loop-mediated isothermal amplification (LAMP), strand displacement amplification (SDA), helicase-dependent amplification (HDA), and nicking enzyme amplification reaction (NEAR).

50. The method of any one of 44-49, including detectably labeling the amplification product subsequent to amplification.

51. The method of any one of 44-49, wherein the amplification reagents include detectably labeled primers and/or probes.

52. The method of any one of 44-51, including detectably labeling the amplification product with a fluorescent label and sorting the multiple-emulsion microdroplets via fluorescence activating cell sorting (FACS).

53. The method of any one of 44-52, including adjusting the composition of the miscible phase fluid solution by adjusting the composition of the miscible phase carrier fluid.

54. The method of any one of 44-53, including detectably labeling the amplification product by adding a detectable label to the miscible phase carrier fluid, wherein the detectable label diffuses from the miscible phase carrier fluid, through the immiscible phase fluid, and into the miscible phase fluid solution.

55. The method of any one of 44-54, wherein the multiple-emulsion microdroplets are first multiple-emulsion microdroplets, and the method includes adding a reagent to the first multiple-emulsion microdroplets, wherein the adding includes encapsulating the first multiple-emulsion microdroplets in second multiple-emulsion microdroplets including the reagent and rupturing the first multiple-emulsion microdroplets within the second multiple-emulsion microdroplets to bring the reagent into contact with the contents of the first multiple-emulsion microdroplets.

56. The method of any one of 44-54, wherein the multiple-emulsion microdroplets are second multiple-emulsion microdroplets, and the method includes adding a reagent to the second multiple-emulsion microdroplets, wherein the adding includes encapsulating first multiple-emulsion microdroplets including the reagent in the second multiple-emulsion microdroplets and rupturing the first multiple-emulsion microdroplets within the second multiple-emulsion microdroplets to bring the reagent into contact with the contents of the second multiple-emulsion microdroplets.

57. A nucleic acid amplification method including:
flowing a miscible phase fluid solution of nucleic acids in a channel of a microfluidic device;
contacting the miscible phase fluid solution of nucleic acids with an immiscible phase fluid, wherein the contacting of the miscible phase fluid solution of nucleic acids with the immiscible phase fluid results in the formation of miscible phase microdroplets surrounded by the immiscible phase fluid;
flowing the miscible phase microdroplets surrounded by the immiscible phase fluid in a channel of a microfluidic device;
contacting the miscible phase microdroplets surrounded by the immiscible phase fluid with a miscible phase carrier fluid including amplification reagents, wherein the contacting of the miscible phase microdroplets surrounded by the immiscible phase fluid with the miscible phase carrier fluid including amplification reagents results in the formation of multiple-emulsion microdroplets, each multiple-emulsion microdroplet including a miscible phase microdroplet surrounded by the immiscible phase fluid, wherein the immiscible phase fluid is surrounded by the miscible phase carrier fluid, and wherein amplification reagents diffuse from the miscible phase carrier fluid, through the immicible phase fluid, and into the miscible phase microdroplets;
subjecting the multiple-emulsion microdroplets to amplification conditions sufficient to result in amplification of a target nucleic acid when present in the miscible phase fluid solution of nucleic acids; and
detecting an amplification product resulting from the amplification of the target nucleic acid when present in the miscible phase fluid solution of nucleic acids.

58. A nucleic acid amplification method including:
encapsulating a cell in a multiple-emulsion microdroplet, the multiple-emulsion microdroplet including a first miscible phase fluid surrounded by an immiscible shell, wherein the multiple-emulsion microdroplet is positioned in a second miscible phase carrier fluid;
subjecting the multiple-emulsion microdroplet to conditions sufficient to effect lysis of the cell in the multiple-emulsion microdroplet;
subjecting the multiple-emulsion microdroplet to conditions sufficient to deactivate or remove one or more materials which have an inhibitory effect on nucleic acid amplification;
introducing nucleic acid amplification reagents into the multiple-emulsion microdroplet;
subjecting the multiple-emulsion microdroplet to amplification conditions sufficient to result in amplification of a target nucleic acid when present; and
detecting an amplification product resulting from the amplification of the target nucleic acid when present.

59. The method of 58, wherein the introducing of the amplification reagents into the multiple-emulsion microdroplet includes introducing the amplification reagents into the second miscible phase carrier fluid, wherein the amplification reagents diffuse from the second miscible phase carrier fluid, through the immiscible shell, and into the first miscible phase fluid.

60. The method of 58, wherein the multiple-emulsion microdroplet does not include more than one cell.

61. The method of any one of 58-60 including detectably labeling the amplification product, when present, with a fluorescent label and sorting the multiple-emulsion microdroplet via fluorescence activating cell sorting (FACS).

62. A nucleic acid amplification method including:
    flowing a cell in a first miscible phase fluid in a channel of a microfluidic device;
    contacting the first miscible phase fluid with an immiscible phase fluid, wherein the contacting of the first miscible phase fluid with the immiscible phase fluid results in the formation of a miscible phase microdroplet including the cell and surrounded by the immiscible phase fluid;
    flowing the miscible phase microdroplet surrounded by the immiscible phase fluid in a channel of a microfluidic device;
    contacting the miscible phase microdroplet surrounded by the immiscible phase fluid with a second miscible phase fluid, wherein the contacting of the miscible phase microdroplet surrounded by the immiscible phase fluid with the second miscible phase fluid results in the formation of a multiple-emulsion microdroplet including the miscible phase microdroplet surrounded by the immiscible phase fluid, wherein the immiscible phase fluid is surrounded by the second miscible phase fluid;
    subjecting the multiple-emulsion microdroplet to conditions sufficient to effect lysis of the cell in the multiple-emulsion microdroplet;
    subjecting the multiple-emulsion microdroplet to conditions sufficient to deactivate or remove one or more materials which have an inhibitory effect on nucleic acid amplification;
    introducing nucleic acid amplification reagents into the multiple-emulsion microdroplet;
    subjecting the multiple-emulsion microdroplet to amplification conditions sufficient to result in amplification of a target nucleic acid when present; and
    detecting an amplification product resulting from the amplification of the target nucleic acid when present.

63. The method of 62, wherein the introducing of the amplification reagents into the multiple-emulsion microdroplet includes introducing the amplification reagents into the second miscible phase fluid, wherein the amplification reagents diffuse from the second miscible phase fluid, through the immiscible phase fluid, and into first miscible phase fluid.

64. The method of 62, wherein the multiple-emulsion microdroplet does not include more than one cell.

65. The method of any one of 62-64, including detectably labeling the amplification product, when present, with a fluorescent label and sorting the multiple-emulsion microdroplet via fluorescence activating cell sorting (FACS).

66. A microfluidic device including:
    a sample receiving channel including a miscible phase fluid;
    a single emulsion droplet maker in fluid communication with the sample receiving channel, the single emulsion droplet maker including one or more channels including an immiscible phase carrier fluid, wherein the single emulsion droplet maker brings the immiscible phase carrier fluid into contact with the miscible phase fluid forming single emulsion droplets;
    a double emulsion droplet maker in fluid communication with the single emulsion droplet maker, wherein the double emulsion droplet maker includes one or more channels including a miscible phase carrier fluid, wherein the double emulsion droplet maker brings the miscible phase carrier fluid into contact with the single emulsion droplets forming double emulsion droplets;
    a thermalcycler in fluid communication with the double emulsion droplet maker, wherein the thermalcycler receives the double emulsion droplets and thermalcycles the double emulsion droplets.

67. The microfluidic device of 64 including a detector, wherein the detector detects the presence or absence of a nucleic acid amplification product in the double emulsion droplets.

68. The microfluidic device of 66 or 68, including a microfluidic sorter in fluid communication with the thermalcycler.

69. A system including the microfluidic device of any one of 64-68 and a Fluorescence Activated Cell Sorter (FACS), wherein the FACS receives and sorts the double emulsion droplets based on the presence or absence of a nucleic acid amplification product in the double emulsion droplets.

70. A method according to any of the aspects described above, wherein the amplification reagents include both multiple displacement amplification (MDA) reagents and polymerase chain reaction (PCR) reagents, and wherein subjecting the multiple-emulsion microdroplet to amplification conditions comprises subjecting the multiple emulsion microdroplet to both MDA amplification conditions and PCR amplification conditions.

71. A nucleic acid amplification method comprising:
    a) encapsulating a nucleic acid and amplification reagents in an emulsion microdroplet, wherein the amplification reagents comprise non-specific amplification reagents and PCR amplification reagents;
    b) subjecting the emulsion microdroplet to amplification conditions sufficient to result in non-specific amplification of the nucleic acid to provide amplification products;
    c) subjecting the emulsion microdroplet to amplification conditions sufficient to result in PCR amplification from the amplification products of step b) to provide PCR amplification products; and
    d) detecting a PCR amplification product resulting from step c).

72. The method of claim 71, wherein the non-specific amplification reagents comprise Multiple Displacement Amplification (MDA) reagents.

73. The method of claim 72, wherein MDA reagents comprise a polymerase which is active under buffer conditions under which Taq DNA polymerase is active.

74. The method of claim 73, wherein the polymerase is a Bst polymerase.

75. The method of any one of claims 71-74, wherein the PCR amplification reagents comprise Taq DNA polymerase.

76. The method of any one of claims 71-75, wherein the emulsion microdroplet is a multiple-emulsion microdroplet comprising a first miscible phase fluid surrounded by an immiscible shell, wherein the multiple-emulsion microdroplet is positioned in a second miscible phase carrier fluid.

77. The method of claim 76, wherein the second miscible phase carrier fluid is a buffered aqueous phase carrier fluid.

78. The method of claim 77, wherein the first and second miscible phase fluids are the same.

79. The method of any one of claims 71-78, comprising detectably labeling the PCR amplification product subsequent to amplification.

80. The method of any one of claims 71-79, wherein the PCR amplification reagents comprise detectably labeled primers and/or probes.

81. The method of any one of claims 71-80, comprising detectably labeling the PCR amplification product with a fluorescent label and sorting the multiple-emulsion microdroplet via fluorescence activating cell sorting (FACS).

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); and the like.

Example 1: Detection of Nucleic Acids Using Double Emulsion PCR

Materials and Methods

Microfluidic chips were fabricated using standard photolithography techniques in poly(dimethylsiloxane) (PDMS). To produce a master, a layer of SU-8 photoresist (Microchem) was spun onto a silicon wafer, and then expose to UV light from a Blakray device under a mylar mask (Fineline Imaging). The wafer was then baked at 95° C. on a hotplate for 1 min and then developed in Propylene glycol monomethyl ether acetate (PGMEA). PDMS polymer and cross-linker mixed in an 11:1 ratio was then poured over the master and then baked at 75° C. for 4 hours. The device was then peeled from the master and holes were punched using a 0.75 mm biopsy coring needle. After that, the device was bonded to a glass slide following oxygen plasma treatment. To make the device channels hydrophobic, Aquapel was flushed into the channels, after which the device was baked in an oven for 20 mins at 65° C. The thickness of the photoresist was maintained at 25 µm while the channel widths at the flow-focusing junctions were 20 µm.

A mixture including DNA molecules derived from heat-lysed *E. Coli*, 2% Polyethylene Glycol 6K (Invitrogen), 2% Tween®-20, TolA detection primers, and a PCR Master Mix (Phusion HF Flex 2×MM) was prepared. Primers were used at a working concentration of 1 µM and were as follows: TolA Forward 5'-GTTGATTCAGGTGCGGTAGTT-3' (SEQ ID NO:1), TolA Reverse 5'-GCCTGCTGTTCCTT-CATCTT-3' (SEQ ID NO:2). The mixture was loaded into a 1 ml syringe back-filled with HFE-7500 oil.

The mixture was introduced into a planar flow-focusing device with a 20 µm nozzle at 400 µL hr$^{-1}$. The carrier oil phase, including HFE-7500 fluorinated oil to which a biocompatible fluorinated surfactant was added at 2% by weight, was introduced at 400 µL hr$^{-1}$. The biocompatible surfactant can include a PEG600 or similar molecular weight molecule bound to a Krytox® FSH. Alternatively, the ionic form of Krytox® can be added to the oil phase and Jeffamine® to the aqueous phase, generating an ionic bond at the interface that stabilizes the double emulsion vesicles.

Using these flow rates and device dimensions, monodisperse single emulsions ~25 µm in diameter were generated. The single emulsion drops were collected into a 1 mL polycarbonate syringe and allowed to cream for 2 min. To generate double emulsion microdroplets, the creamed single emulsion was introduced into another planar-flow focusing device with a 25 µm nozzle at a flow rate of 200 µL hr$^{-1}$. Simultaneously, the carrier aqueous phase was introduced at 400 µL hr$^{-1}$. The carrier phase is thickened with 10% polyethylene glycol (molecular weight 35K), which allowed for higher shear rates for these flow rates, enabling improved double emulsification. The carrier phase also contained Pluronic F-68 at 1% by weight, to stabilize the double emulsions generated.

The double emulsion microdroplets were collected into PCR tubes and centrifuged at 3000 rpm for 5 minutes to concentrate them. They were then resuspended in 1× HF detergent-free buffer, and 1% Pluronic F-68. This suspension was thermalcycled on a T100 thermocycler (Bio-Rad), using the following conditions: 10 min at 95° C., 35 cycles of 10 s at 95° C., 30 s at 55° C. and 15 s at 72° C. The double emulsion microdroplets were then concentrated by centrifugation at 3000 rpm before resuspension into a 1×SYBR green (Invitrogen) solution before imaging.

Results

Figure 7:
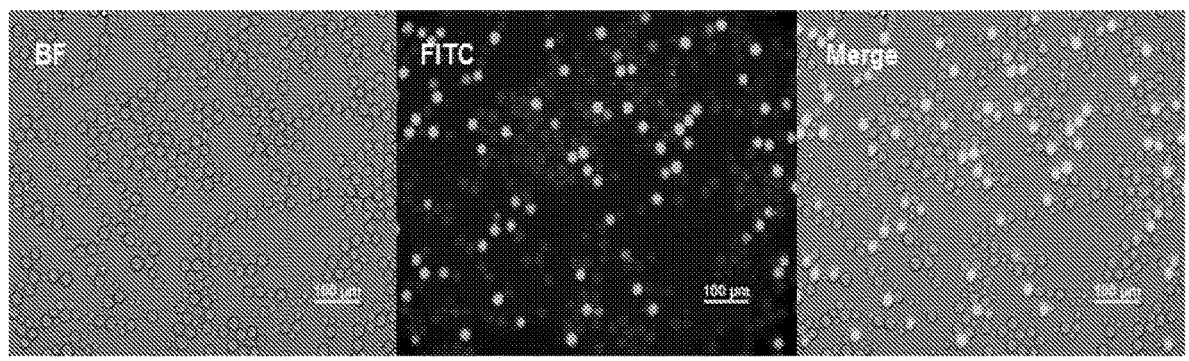
FIG. 7 provides a double emulsion PCR fluorescence readout for *E. coli* that have been heat-lysed and assayed for a TolA genomic region as described in Example 1.

The imaging results for the double emulsion PCR described above are provided in FIG. 7. Because the initial loading of the target molecules was random, some double emulsion microdroplets are fluorescent, seeded by at least one target molecule, and others are not, devoid of a target. By fitting the fluorescence statistics to a Poisson distribution, it was possible to correct for multiple encapsulations and obtain an accurate target molecule concentration. These data show that double emulsion microdroplets are thermostable at 25 µm and can be utilized for digital PCR.

Example 2: Prophetic Example of FACS Analysis of Double Emulsions

Double emulsion microdroplets may be sorted via FACS. Exemplary conditions for such sorting are as follows: Double emulsion microdroplets are diluted with PBS in a 1:1 ratio and transferred to a 12×75 mm round bottom tube for analysis with a FACSAria IIu (BD Biosciences). PBS is used as the sheath fluid and events are run with a flow rate that corresponded to 200 events s$^{-1}$. The cytometer is maintained at a temperature of 4° C. and the tube is rotated at a speed of 300 rpm during event recording. For detection of FITC and TaqMan® probes, FITC-BSA and the TaqMan® probe are excited with a 488 nm laser and their emission passed through a 530±30 nm bandpass filter with a 505 nm low-pass filter in series.

Example 3: Prophetic Example of Nucleic Acid Detection Via PCR in Giant Unilamellar Vesicles (GUV)

Demonstrating Microfluidic Generation and FACS Sorting of Thermostable Femtoliter GUVs Giant Unilamellar Vesicles (GUVs) are sacs of membrane-bound aqueous fluid suspended in a miscible aqueous phase. Like droplets, they can encapsulate regents and thus act as compartments for biological reactions. Depending on the chemistry of the membrane, GUVs can be made selectively permeable, trapping macromolecules like DNA and RNA, but allowing small molecules, like nucleotides and ATP, to pass freely through their membrane. This selective permeability makes reactions in GUVs more efficient than in emulsion droplets because, as the reaction progresses, new reagents can diffuse in. The challenge to performing reactions in GUVs, however, is that they are fragile, consisting of a membrane a few molecular layers thick that can easily rupture due to mechanical stress or heat. To perform PCR in GUVs, a membrane composition must be identified that can withstand repeated thermalcycling up to 95° C. The use of GUVs would allow reactors to be made much smaller than those used in digital droplet PCR, saving reagent, increasing throughput, and allowing more reactions. This, in turn, would increase the sensitivity of dPCR, allowing it to detect and quantitate DNA with greater accuracy.

Molecules and PCR reagents are introduced into a microfluidic device and loaded into GUVs. The concentrations of the molecules are fixed such that, on average, 1 in 10 GUVs contains a single molecule, and the others are empty. The GUVs, suspended in an aqueous phase, are centrifuged to concentrate them, the supernatant removed, and PCR buffer containing reagents essential for the reaction added. The GUVs are then thermocycled in a PCR machine. During thermocycling, GUVs containing single molecules undergo amplification, whereas those that are empty do not. Depending on the detection method used, this makes the amplified GUVs fluorescent either by unquenching dyes attached to the PCR probes or by allowing intercalating dyes like SYBR Green to diffuse into the cores and stain the amplicons. By this point the GUVs are ready for FACS quantitation and sorting. The thermocycled GUVs are concentrated a second time and resuspended into FACS buffer. During FACS, all GUVs are detected using forward and side scattering and, simultaneously, fluorescence values for channels appropriate to the PCR dyes are monitored. The FACS records the proportion of GUVs that are fluorescent, providing a measurement of the concentration of the target DNA in the original solution and, if sorting is turned on, sorts the GUVs falling within the specified gating parameters. The sorted GUVs are ruptured by mixing the suspension with perfluorooctanol and vortexing, and then a nucleic acid prep is used to recover the original target molecules and discard amplicons.

Microfluidic Methods for Generating GUTS.

GUVs will be generated by first generating double emulsions and then inducing the double emulsions to undergo dewetting. In dewetting, the immiscible phase of the double emulsion, e.g., oil, is expunged from the shell, leaving behind a membrane of surfactant, with a small immiscible phase droplet adhered to the outside of the membrane. The size of the resulting GUV is governed by the size of the double emulsion from which it is borne: if the double emulsions are monodisperse, then the resulting GUVs are monodisperse as well. In preliminary experiments, the ability to generate extremely monodisperse double emulsions down to 10 μm in diameter (FIG. 11) has been demonstrated. These double emulsions can be used to form monodisperse GUVs of the same size.

Identify Microfluidic Nozzle Size to Achieve 100 kHz Production of GUVs.

Figure 11:
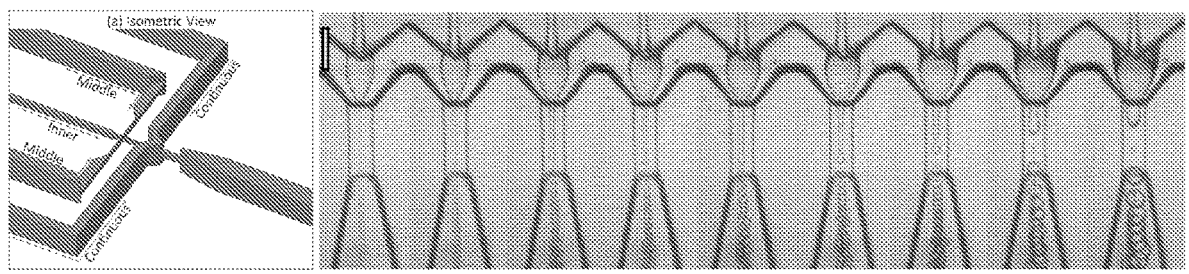
FIG. 11 shows a schematic (left) and image (right) of a coaxial flow focusing double emulsification device which may be utilized to produce double emulsion microdroplets in connection with the disclosed methods, systems and devices. The inner, middle, and carrier phases merge at the junction which, due to an expansion of height and the high flow rate of the carrier phase, generates a coaxial cone of the inner and middle phases. The cone is flow focused through a constriction, ripping off monodisperse double emulsions. Varying the ratio of flow rates of the three phases allows small (left) and large (right) double emulsions to be formed. The scale bar is 50 µm.
Figure 12:
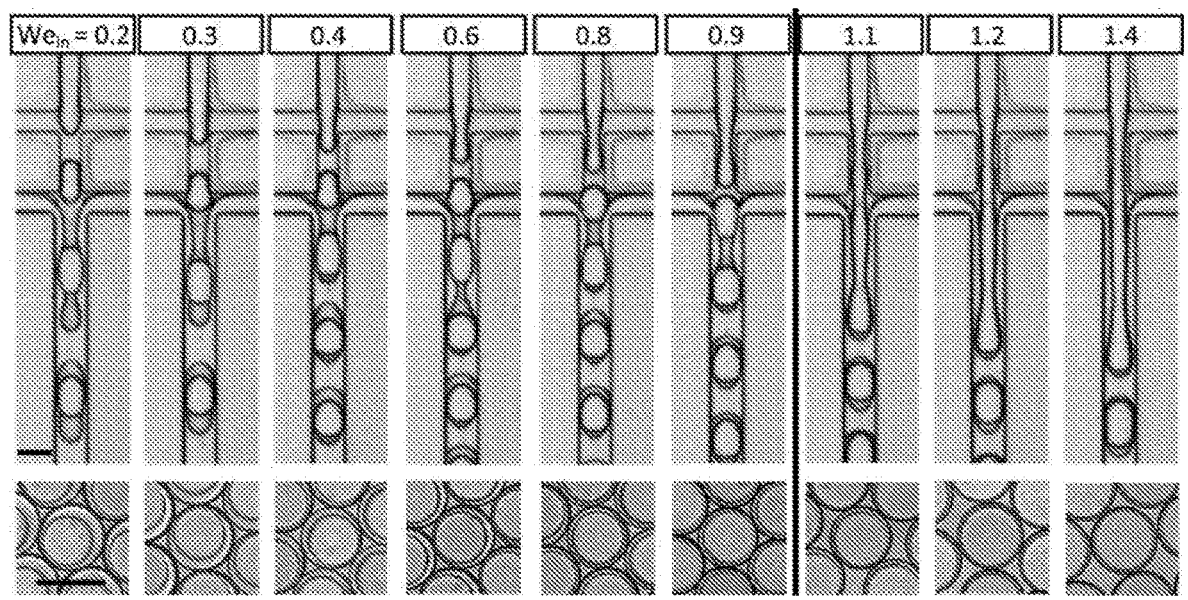
FIG. 12 shows an image of a double emulsion droplet maker using planar, spatially-patterned microfluidics. The device is chemically patterned to be hydrophobic in its top half and hydrophilic in its bottom half, allowing water-in-oil droplet generation in the upper junction and oil-in-water double emulsification in the lower junction.

In microfluidic generation of GUVs, production rate increases as GUVs get smaller. Therefore, GUV production will be monitored and modified to identify a size that enables the generation of 1 billion in a few hours. In coaxial flow focusing and plugging-based generation, GUV size depends on the dimensions and geometry of the shearing nozzle. Accordingly, different nozzle dimensions and geometries appropriate for forming 5 μm GUVs at 100 kHz will be tested. A coaxial flow focusing device as shown in FIG. 11, which has been shown to make double emulsions down to 10 μm, will be utilized. This device has the benefits of being simple, forming the double emulsions rapidly in a one step process, and also requiring no wettability patterning, making the fabrication easy. If coaxial flow focusing is not adequate, flow focusing in planar, wettability patterned devices, will be tested, which have been shown to generate monodisperse double emulsions (FIG. 12). In this method, the microfluidic channels are spatially patterned to be hydrophobic in certain regions, enabling formation of aqueous-in-oil emulsions, and hydrophilic in others, allowing encapsulation of the aqueous droplet in an oil droplet, and generation of a water-in-oil-in-water double emulsion. The primary advantage of this method is that it allows the double emulsions to be generated with less carrier fluid, making it more cost effective. However, it is unable to produce droplets as rapidly as coaxial flow focusing, because it is limited to plugging-based droplet generation, whereas coaxial flow focusing can operate in the much faster jetting regime.

Adjust Chemical Formulation as Necessary to Produce Thermostable GUVs at 100 kHz.

The formulation of the shell and carrier phases of the GUVs will be adjusted as needed by including different surfactants (e.g., Tween® 20, Span® 80, Pluronic, etc.) and/or different thickening agents (e.g., PEG, alginate, glycerol, etc.) in the carrier phase. Surfactants should be chosen carefully because they affect the generation rate and stability of the GUVs. The viscosity of the carrier phase should also be chosen to match the surfactant since, in the droplet generation process, size and rate depend on the capillary number which, itself, depends on the interfacial tensions of the fluids (and thus the surfactants) and the shear rate of the carrier phase (and thus the thickeners). A combination that is likely to work once a suitable nozzle geometry is identified is one which includes Pluronic surfactant in the carrier phase, Tween® and Jeffamine® in the inner phase to shield unbound carboxylates in our fluorinated polyether PEG surfactant, and thickeners in the carrier phase including high molecular weight PEG, BSA, and glycerol. The chemistries of the emulsions may need to be adjusted to optimize for 5 μm GUVs, which have a higher curvature than 40 μm GUVs. This can be done by synthesizing surfactants with different hydrophilic-hydrophobic block sizes and with additives included in the carrier phase.

Identify Additional Block-Copolymer Surfactants for Generating Thermostable GUVs.

To generate thermostable vesicles, block-copolymer surfactants that have high melting temperature when assembled into vesicles in aqueous phases will be tested. The melting temperature of a vesicle membrane depends on its solubility in the carrier phase which, in turn, depends on its chemistry and molecular weight. Accordingly, high molecular weight, fluorinated surfactants will be tested. These will include fluorine end-capped homopolymers of hexafluoropropylene epoxide-polyethylene-glycol surfactants with varying molecular weights for the hydrophobic-hydrophilic blocks. The relative molecular weights of these blocks are important because they determine the geometry and packing of the molecule on the vesicle membrane which, in turn, influences dewetting, melting temperature, and the natural membrane curvature that is most stable. Molecular weights of 6,000-10,000 for the hexafluoropropylene epoxide blocks and 600-800 for the PEG block are effective at yielding thermostable GUVs 40 μm diameter. These weights may need to be varied to stabilize much smaller 5 μm GUVs by making the PEG blocks smaller. There are a wide range of molecular weights commercially available for hexafluoropropylene epoxide (Krytox) and PEG (Jeffamine). PEG blocks not capped by polyethylene oxide, which can influence the geometry of the surfactant and impact GUV thermostability and size, will be tested. The use of additives to bind dangling carboxylates left over from incomplete synthesis of the surfactants which are difficult to remove via purification will be tested, including BSA and other proteins.

Measure Maximum FACS Detection and Sorting of GUVs.

GUVs are membrane-bound sacs of aqueous fluid dispersed in an aqueous phase. To a FACS, they thus appear as cells, with a similar composition and size as cells. As a result, FACS sorting GUVs is identical to sorting cells and can be performed on any commercially available system without modification to the instrument or process. When FACS sorting GUVs, the sorting rate depends on the flow injection rate and the GUV concentration. 40 μm GUVs can be FACS analyzed at the maximum flow rate (75 psi, FACSAria) and they survive sorting intact. It is anticipated that this will be the case for 5 μm GUVs as well, since the robustness of a GUV against breakup depends on its Laplace pressure, $p=2\lambda/r$, where r is the GUV radius, which increases as the GUVs get smaller as 1/r. It will be confirmed that 5 μm GUVs can be FACS sorted at these rates and, if they cannot, different formulations will be tested to identify those with increased resistance to shear. To increase the sorting rate still further, the sample may be concentrated. 40 GUVs can be concentrated with centrifugation and then re-suspended to a working concentration by adding an appropriate amount of FACS buffer. Concentration via centrifugation of the smaller 5 μm GUVs, which may be harder to spin-down due to their smaller gravitational mass, will be tested. The parameters to adjust will be the spin speed and time. Concentration via ultracentrifugation may also be tested. The viscosity of the GUV carrier phase will be varied since the settling velocity is governed by the ratio of gravitational forces to viscous drag, $mg/\eta v$. 40 μm GUVs survive centrifugation easily and therefore it is expected that 5 μm GUVs will survive as well since their higher Laplace pressure should make them even more robust to shear and compression forces. The maximum packing density achieved will likely be 64% which, for randomly-close packed spheres, is the jamming transition. Above this density the suspension will have an elastic modulus, which will likely cause the FACS nozzle to clog.

Characterize Sorting Error Rate.

As the sample becomes more concentrated to increase the sorting rate of the FACS, the probability that two GUVs enter at the same time increases. Consequently, if one of the GUVs is flagged for sorting, the other will be sorted too. The statistics that govern this are described by a Poisson distribution and predict that increasing sample density will increase positive sorting errors. This phenomenon will be monitored and queuing statistics will be used to model the error process. It is expected that the model will break down as the flow becomes non-Newtonian due to thickeners in the carrier phase, interactions between GUVs, and jamming effects. Accordingly, these parameters will be varied to test the validity of the model and determine what the absolute maximum sorting rate is and how error rate scales with system parameters.

Implement Tiered Sorting to Highly Enrich for Very Rare Positive GUVs.

Because the majority of FACS sorting errors result from the entrance of two or more GUVs into the sorter simultaneously, most sorting errors are positive errors: nearly all positive GUVs are recovered, but so are many negative ones. This type of sorting error is amenable to tiered sorting to continuously enrich for the population of interest. For example, for a conservative enrichment of 100× per sorting round, 1 billion GUVs can be sorted in ~3 hrs to yield 10 million GUVs, in which the positives are enriched by 100×. Slowing the sorting to 1 kHz results in near perfect sorting, allowing the remaining 10 million GUVs to be sorted in an additional 3 hrs to recover an essentially pure solution of positive GUVs. Using tiered sorting, it should be possible to detect and recover tens of positive GUVs in a population of billions with ~6 hrs of sorting. This will make the disclosed methods useful for detecting and recovering molecules, viruses, or cells present at extremely low abundance in a diverse population.

FACS Sorting of Single GUVs into Wells.

Because GUVs are treated by the FACS as cells, like cells, they can be individually sorted into wells. Methods of accomplishing this will be tested and optimizes. GUVs can be ruptured with perfluorooctanol and, using methods described below, we should be able to remove contaminating amplicons generated during the GUV-PCR. After this point, the molecule can be amplified with nonspecific methods (MDA, MALBAC), the amplicons barcoded, and the barcoded reads sequenced. This should allow for the recovery and sequencing of molecules as large as chromosomes, and the number of such molecules is limited only by the number of wells that can be FACS-loaded (e.g., 384 per plate) and the amount of sequencing capacity available. This will be valuable for screening large and diverse populations to identify, recover, and sequence rare molecules, viruses, or eukaryotic cells. The terms "nucleic acid barcode sequence", "nucleic acid barcode", "barcode", and the like as used herein refer to a nucleic acid having a sequence which can be used to identify and/or distinguish one or more first molecules to which the nucleic acid barcode is conjugated from one or more second molecules. Nucleic acid barcode sequences are typically short, e.g., about 5 to 20 bases in length, and may be conjugated to one or more target molecules of interest or amplification products thereof. Nucleic acid barcode sequences may be single or double stranded.

Optimize and Characterize GUV-PCR and Benchmark Efficiency Against Aqueous Droplets As the size of a droplet is reduced, the efficiency of a reaction performed inside it goes down. Reaction inhibition is a consequence of two factors: As droplets get smaller, their volume reduces with the cube of the diameter, so that droplets half the size have $\frac{1}{8}^{th}$ the volume. This rapid reduction in volume means that for very small droplets, reagents can be limiting. Another source of inhibition is that the oil-water interface of droplets can denature enzymes due to their amphiphilic composition. Because the surface-to-volume ratio goes up as droplets get smaller, interfacial inhibition becomes more prevalent. For these reasons, even though it is possible to generate droplets below 5 µm in diameter, the practical lower limit for most droplet-based reactions is ~50 µm. GUV formulations will be tested to identify those that afford higher biocompatibility than droplets to enable reactor size to be reduced to 5 µm, a 1000× reduction in volume. This will enable the performance of 1000× more reactions with the same volume of reagent.

Optimize PCR in 5 µm GUVs.

5 µm GUVs will be generated and the effect of different chemical formulations on their stability and PCR efficiency will be determined. To perform PCR in the GUVs, known concentrations of plasmids containing a BRAF gene will be dispersed so that they are present at an average of 0.1 per drop with DNA polymerase, dNTPs, PCR buffer, and pre-designed primers that amplify a hundred base fragment of the gene. The initial plasmid concentration will be determined fluorometrically using a Qubit 2.0 fluorometer. The GUVs will then be thermocycled and SYBR green added to the carrier phase, which chemically partitions through the GUV membrane and specifically stains GUVs that undergo amplification. To quantify GUV-PCR efficiency, the GUVs will be imaged to measure the fraction that are fluorescent and the average and standard deviations of the endpoint values. To benchmark the efficiency of this process against droplet reactions, this experiment will be repeated with a QX100 digital droplet PCR machine (Bio-Rad). The GUVs and droplets from the QX100 control experiments will be ruptured with perfluorooctanol and DNA recovered and analyzed with gel electrophoresis and fluorometry to estimate yields. This workflow will be performed for all mix combinations. Because this is a multi-parameter optimization, all data will be stored in an array format relating mix composition to droplet fluorescence statistics and DNA yields, allowing for the use of multiple regression to predict optimal mix combinations, which will be independently tested.

Investigate Effect of Additives on GUV Stability and PCR Efficiency.

Known emulsion stabilizers and PCR additives will be tested to investigate their effect on GUV-PCR, including polyetheramines that can bind to the carboxylate groups of surfactant and thus suppress enzyme adsorption to the interface; this should markedly increase reaction efficiency in GUVs. Jeffamine® ED-600, ED-900, and ED-2003 will also be tested at molar ratios of 0.1, 1, and 10 to surfactant. Bovine serum albumin (BSA) will also be tested, which adsorbs to amphiphilic interfaces and generates a biocompatible "skin" that shields enzymes from denaturation. BSA concentrations of 0.5, 1, and 2% (w/v) will be tested in the PCR mixes. The carrier phase will also be supplemented with different concentrations of dNTPs (starting at 200 µM) and $MgCl_2$ (1.5 mM), which can chemically partition into the GUVs and improve efficiency as reagents are consumed by the reaction.

Characterize Chemical Partitioning Through Vesicle Membrane and Identify Methods to Control it.

The permeability of GUV membranes will be investigated and methods for attenuating it will be identified. Macromolecules, like DNA and proteins, remain well-encapsulated in GUVs, but small molecules, like SYBR green, are able to diffuse into them over time. Membrane permeability will be characterized as a function of temperature, small molecule size and chemical properties utilizing different molecular weight FITC-dextrans (5, 10, 20, 30, 40, 50 kDa). At the low-molecular weight scale, Xanthine family dyes (fluorescein, rhodamine), cyanine family dyes (indocarbocyanine, oxycarbocyanine), and coumarin derivatives (4-hydroxycoumarin) will be utilized. These results will be compared with the release profile of fluorescein at comparable concentrations. After permeability for these molecules has been characterized, different methods of attenuating the permeability will be tested, including the addition of 5% BSA (w/v) to the carrier phase, which greatly slows the rate of SYBR partitioning in 40 µm GUVs. The smaller proteins ovalbumin, β-casein and t4 gene protein 32 will also be tested at different concentrations. In addition to proteins, polymers will be investigated (Jeffamine® ED-600, ED-900, and ED-2003) at molar ratios of 0.1, 1, and 10 to surfactant. Polyglycols (Dow), which can be functionalized with amines and have been shown to form massive dendritic polymers that better shield hydrophobic interfaces than linear ones like PEG, will also be investigated.

Explore Methods to Multiplex PCR.

Multiplexed TaqMan® PCR is valuable for applications in which two or more sequences must be correlated within a single sample. With GUV-PCR, this will enable the mapping of mutations on the same chromosome, or the identification of microbes having a specific combination of genes, to name just two examples. Multiplexed TaqMan® PCR relies on the ability to label the TaqMan® probes with dyes of different spectra, allowing the amplification of several regions to be measured simultaneously with spectrophotometric techniques. TaqMan® PCR utilizes probes labeled with a fluorophore and quencher, and accompanying primer sets. During amplification, the probes anneal to regions between the primers and are cleaved by the 5'-3' exonuclease activity of certain DNA polymerases; cleavage releases the fluorophore, allowing it to fluoresce and providing an optical readout of amplification. TaqMan® probes will be designed and tested using the QX100 as a control—a commercial product that is validated for multiplexed single emulsion PCR. Three non-overlapping regions in the plasmid pUC19 will be targeted and amplification efficiency will be measured in a Stratagene Mx3005p qPCR machine. After validation, the probes will be retested in the QX100 to confirm that they work in digital formats as well; this is an important test because probes that are effective in conventional qPCR do not always perform adequately in droplet PCR, yielding heterogeneous endpoint fluorescence values that do not provide an accurate measurement of DNA concentration. If a probe set performs poorly in the droplet format, a new probe set with modified recognition sequences will be tested. Some probes are more effective in droplet formats than others and because probe suppliers do not generally spec their DNA for these formats, the only way to validate a probe set is with a droplet PCR experiment. Nevertheless, it is generally possible to identify a good probe set for a specific region in 2-3 attempts.

Molecular Beacons.

Molecular beacons are PCR probes with higher hybridization specificity than linear probes like TaqMan®, due to their use of secondary structure to increase the entropy of hybridization. These probes include a hairpin-loop and stem structure with the reporter and quencher on the end of the stem. Like TaqMan®, PCR causes the reporter and quencher to separate, yielding an increase in fluorescence. Other benefits of these probes are that they do not require a polymerase with exonuclease activity and also remain intact through the reaction, resulting in only macromolecules at the end of the PCR that are well retained in the GUVs. Like the TaqMan® experiment, three regions of pUC19 will be targeted with different probes and all probes will be validated with qPCR and droplet PCR before testing in GUVs.

Scorpion Probes.

Like Molecular Beacons, scorpion probes are bi-labelled hairpin-loop probes that utilize dye-quencher separation to yield fluorescence under amplification. However, these ~25 nucleotide probes unfold and the loop region then binds to the target region of the amplicon. An advantage of this strategy is that the probe remains bound to the amplicon, again making it part of a macromolecular structure that will be well confined in the GUVs. In addition, because enzymatic cleavage of the hairpin is not required and the probes are part of the primer amplicons, the reaction tends to be more efficient than Molecular Beacon or TaqMan® PCR. Like the Molecular Beacon and TaqMan® experiments, three non-overlapping probe sets will be tested on pUC19.

Optimize Methods to Rupture GUVs.

One of the principal benefits of GUVs is that they will allow the FACS sorting of individual DNA molecules detected with digital PCR. To fully exploit this, methods for robustly recovering molecules out of the GUVs for downstream sequencing are needed. In preliminary experiments, the controlled rupture of 40 μm GUVs with a buffer consisting of 1:1 (v/v) HFE-7500 to perfluorooctanol has been demonstrated. This breaking buffer ruptures GUVs by solubilizing the perfluorinated bilayer membrane. Because the GUV rupture is chemical in nature, it is anticipated that it will work equally well for 5 μm GUVs. If this is not the case and it is found that 5 μm GUVs are more difficult to rupture, mechanical methods to enhance rupture will be tested, including flowing GUVs through 1 μm filters, using high-shear homogenization at 50 Hz with bead beating, and ultrasonication at 20-100 kHz. The use of flow through microfluidic channels with a high-voltage AC field applied may also be tested, which has been shown in preliminary experiments to rupture GUVs. These methods will also be combined with chemical techniques designed to destabilize the GUVs, including adding chloroform that solubilizes the PEG moiety of the surfactant. The use of osmotic shock via the addition of hypertonic or hypotonic solutions, which have been shown to crush or explode GUVs, respectively, will also be tested. Yet another approach which can be tested, if necessary, is the use of high and low pH, which have been shown to be effective in rupturing emulsions.

Develop Protocol to Remove GUV-PCR Amplicons from Recovered DNA.

In preliminary experiments, it has been confirmed by qPCR, DNA sequencing, and gel-electrophoresis that target molecules >1 megabase survive digital PCR. However, at the conclusion of the process, these target molecules will be mixed in with thousands of short amplicons in the GUVs. These amplicons, after sorting, represent DNA contaminants that should be removed before sequencing. As a test system, one region of pUC19 will be amplified using dUTPs instead of dTTPs, so that all amplicons generated in the GUV-PCR will have uracil in place of thymine. These amplicons can then be selectively digested using uracil DNA glycosylase, which catalyzes the hydrolysis of the N-glycosidic bond between uracil and its sugar, leaving only the original target molecules lacking in uracil. An alternative method will be to use biotinylated primers so that amplicons can be selectively removed with streptavidin-conjugated agarose beads. qPCR will be used to estimate the concentration of contaminating amplicons after these purifications.

Demonstrate 1000× Greater Sensitivity than Competing Platforms by Performing Over 1 Billion Digital GUV-PCRs, and Recovery of Positive Molecules with FACS The objective of this experiment is to demonstrate that GUV-PCR can be used to quantitate DNA with 1000× greater sensitivity than the best commercial alternatives and also to demonstrate the ability to selectively recover molecules with FACS sorting. As proof-of-principal demonstrations, synthetic DNA samples and patient samples will be screened. The goal with the patient sample screen will be to show that GUV-PCR enables detection of cancer DNA at lower concentrations and with greater accuracy than existing commercial products and published droplet techniques. This example is not intended to be limiting: the same workflow without modification can be applied to detect DNA in the blood from other sources (fetus, pathogens), to screen large and diverse genomic fragment libraries to enrich for regions of interest, to sort chromosomes, and to recover, in a cultivation-free manner, uncultivable viruses and microbes in native ecologies.

Synthetic DNA Spike-in Experiment.

A spike-in experiment will be performed to demonstrate the utility of GUV-PCR for detecting and recovering extremely rare DNA variants. A rare mutant allele of BRAF, a proto-oncogene, will be used as the model rare molecule. This variant of BRAF, V600E, will be cloned into a pUC19 vector. Wild type BRAF will also be cloned into pUC19 to provide a background molecule. Probes will be designed to detect the variant so that upon thermalcycling only GUVs with the mutant allele fluoresce. After transforming electrocompetent E. coli with plasmids for these two variants of BRAF, the DNA will be extracted and quantified with a Qubit fluorometer. A protocol has been developed that transforms without pre-amplifying sorted DNA and recovers as few as 10 sorted molecules. This will be used to calculate the molecular concentration of plasmid molecules in the two DNA preparations. Using these numbers, spike-ins of mutant-to-wild type will be prepared at $10^{-9}$ to $10^{-4}$. Based on the anticipated throughput with microfluidic generation of 5 μm GUVs, it should be possible to detect and sort several mutants present at as few as 1 in 100 million for a Poisson loading of 0.1. After thermalcycling, the GUVs will be subject to FACS at a rate of 50 kHz, allowing for the sorting of 1 billion GUVs in ~5 hrs. The sorted GUVs will be ruptured using the protocol discussed above and qPCR will be used to quantitate the relative amounts of amplicon to original template. To confirm the enrichment of the mutant allele, PCR amplification followed by cloning into a TOPO-TA vector, transformation into E. coli, DNA prep, and Sanger sequencing will be performed. This process will be repeated varying spike in ratios, DNA concentrations, GUV loading rates, and FACS parameters to characterize the sensitivity of the approach and the limit of detection and sorting of rare molecules.

Detect, Recover, and Sequence Bcr/Abl Transcripts in Blood Obtained from Patients with Chronic Myelogeneous Leukemia.

The majority of patients with chronic myelogeneous leukemia (CML) have a translocation of the long arms of chromosomes 9 and 22, which transposes the c-abl oncogene from chromosome 9q34 to the BCR gene on chromosome 22q11. This fusion provides specific markers for monitoring disease progression of CML. qPCR techniques are currently used to detect this marker but their limited sensitivity and precision prevent monitoring in many circumstances, particularly early in the disease when the DNA is present at very low concentrations. In this experiment, the utility of GUV-PCR for this diagnostic application will be demonstrated, enabling the detection of these cancer markers at 1000× lower concentration and even recovery and sequencing by direct sorting of the positive molecules. Bone marrow samples will be procured from patients and other unaffected donors. RNA will be extracted with kits from Qiagen, quantified with the Qubit fluorometer, and subjected to reverse transcription with the Quantitect Reverse Transcription kit. Primers will amplify Bcr/abl transcripts only if they are fused. Total cDNA will be encapsulated with PCR reagents as discussed herein and the GUV workflow and FACS sorting will be performed, providing an absolute quantitation of total bcr/abl molecules. The positive GUVs will be individually FACS sorted into wells on a 384-well plate using FACSAria, the GUVs ruptured, and the sequences amplified with primers specific to bcr and abl. The resulting PCR products will be cloned into a TOPO-TA vector, transformed into electrocompetent E. coli, and the extracted DNA Sanger sequenced to quantify the statistics of Bcr/abl fusion in the patient (i.e. b2/a2, b3/a2, etc.).

Example 4: Prophetic Example of Passive Generation of Double Emulsions Using a Hand-Pressure Pump Double emulsions can be generated passively using a constant pressure applied by a hand pump, such as a syringe. For this method, the inlet reservoirs are loaded with the solutions to be double emulsified and the inlets sealed within a pressure-holding vessel. The outlet is maintained open to the atmosphere. The air within the inlet pressure reservoir is then compressed by a controlled amount, generating a controlled pressure and pressure differential through the device, by compressing the piston of a reservoir connected to the inlet, such as a syringe. This pressure differential pumps the fluids through the double emulsifier, generating double emulsion droplets.

The channel dimensions, fluid properties, and applied pressure may be selected so as to ensure proper formation of the desired double emulsions. Because the volumes of the pressure reservoir can be large compared to the device and inlets and the compression volume controlled using mechanical locks or graduation marks, this method allows steady, long-lived, and controlled application of pressure and generation of double emulsions.

Example 5: Preparation of Device for Double Emulsion Production

To produce a master for single-device double emulsion production, a layer of SU-8 photoresist was spun onto a silicon wafer, followed by exposure to UV light in the presence of a mylar mask. The wafer was then baked at 135° C. for 1 minute. A second layer of SU-8 photoresist was spun onto the exposed PDMS and exposed to UV light in the presence of a second mylar mask followed by a second bake at 95° C. for 1 minute. The wafer was then developed in Propylene glycol monomethyl ether acetate. PDMS polymer and crosslinker mixed in an 11:1 ratio was then poured over the master and baked at 75° C. for 4 hours. The device was then peeled from the master and holes were punched using a 0.75 mm biopsy coring needle followed by oxygen plasma treatment and bonding to a layer of PDMS. To make the device channels hydrophobic, the PDMS chip was incubated at 75° C. for 2 days. The channel dimensions were 15×15 µm for the first inlet and 30×30 µm for the second junction. To create a hydrophilic junction at a second junction while maintaining the hydrophobic qualities at the first junction, the oil inlet and aqueous inlet were blocked while the second aqueous inlet and the outlet remained exposed. The device was then treated with oxygen plasma for 2 minutes. To create a more permanent modification of the surface chemistry, the device can be treated with solvent prior to oxygen plasma treatment as described in Vickers, et al., Anal. Chem, 2006, 78 (21), pp 7446-7452.

Example 6: DNA Amplification and Detection in Double Emulsions Using Single-Device Double Emulsion Preparation DNA molecules derived from lambda phage were amplified and analyzed using a single-device double emulsion preparation device prepared according to Example 5 and a method as described below.

Materials and Methods

DNA molecules derived from lambda phage were systematically diluted by a factor of 2. A mixture including lambda phage DNA dilutions, 4% polyethylene glycol 6K, 4% Tween-20, lambda detection primers, and a PCR Master Mix was prepared. Primers were used at a working concentration of 1 µM and were as follows: 5'-CTTT-GAATGCTGCCCTTCTTC (SEQ ID NO:3) and 5'-CAGA-TAACCATCTGCGGTGATA (SEQ ID NO:4).

The mixture was loaded into a 1 ml syringe back-filled with HFE-7500 oil. The mixture was introduced into a planar flow-focusing device with a 20 µm nozzle at 90 µL hr-1. An immiscible phase, including HFE-7500 fluorinated oil to which a biocompatible fluorinated surfactant was added at 2% by weight, was introduced at 80 µL hr-1. A carrier phase, containing Pluronic F-68 at 1%, as-well-as Tween-20 at 4% and PEG35K at 10%, was introduced at 250 hr-1. Double Emulsions were collected in 0.2 mL PCR tubes.

Resulting double emulsions were incubated using the following conditions: 2 min at 95° C., 40 cycles of 30 s at 95° C., 1.5 min at 60° C. and 20 s at 72° C. The cycled emulsions were treated with 1×SYBR Green. Stained emulsions were injected onto a FACS Aria2, where positive fluorescence was determined as compared to negative controls.

Results

Figure 15:
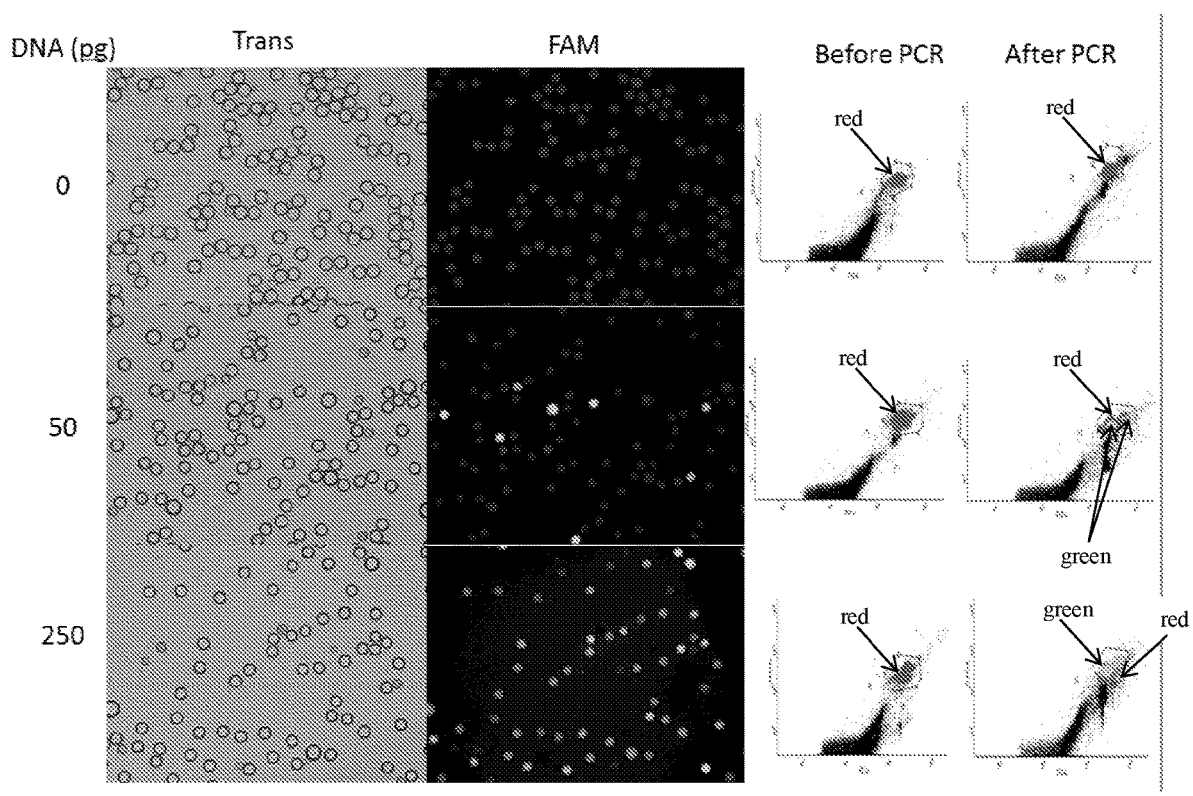
FIG. 15. Digital PCR in double emulsions. Left panels shown brightfield and fluorescence images of double emulsions used to perform digital PCR, right panels show FACS plots of the double emulsions plotted as side scatter vs. forward scatter, with gating parameters shown. Red events denote double emulsions with fluorescence below the minimum fluorescence gate (not shown) while green events denote double emulsions with intensities above this threshold. The rows correspond to samples with different target DNA concentration in picograms, as labeled. Before PCR, no fluorescence positive events are detected but post PCR, many fluorescence positive events are detected, in which the number of events scales with the target DNA concentration.

For double emulsion digital droplet PCR (3DPCR) to be effective for quantitating nucleic acid target molecules, the proportion of droplets that are fluorescent should scale as a function of the concentration of the target molecules in solution, such that measurements of the fraction of fluorescent droplets can be used to infer the original concentration of molecules. To illustrate this, three samples of nucleic acids were generated at different concentrations of target molecules, 0, 50, and 250 pg, FIG. 15. The samples were subjected to 3DPCR analysis as depicted in FIG. 14, and imaged in brightfield and fluorescent modes (FIG. 15). As expected, the proportion of fluorescent droplets increased with increasing concentration of the target. To quantify these findings, the droplets were scanned with a FACS instrument. The double emulsions are relatively large objects that scatter strongly on the FACS. As a result, when the data is used to plot the measured side scattering as a function of forward scattering for each event, multiple populations are observed, a large population of small scattering objects, likely oil droplets and particulate, and a smaller population of large scattering events, which are the double emulsions and appear in the red gated population in FIG. 15, right. Before PCR, it was observed that all of the double emulsions were dim and fell below the defined fluorescence threshold of being PCR positive, but after thermal cycling, a fraction of the double emulsions appeared brightly fluorescent and fell above the threshold. As a result, with increasing target concentration, a population of positive droplets appeared (green points, FIG. 15, right) in which the fraction of positive droplets increased with higher target concentrations.

Figure 13:
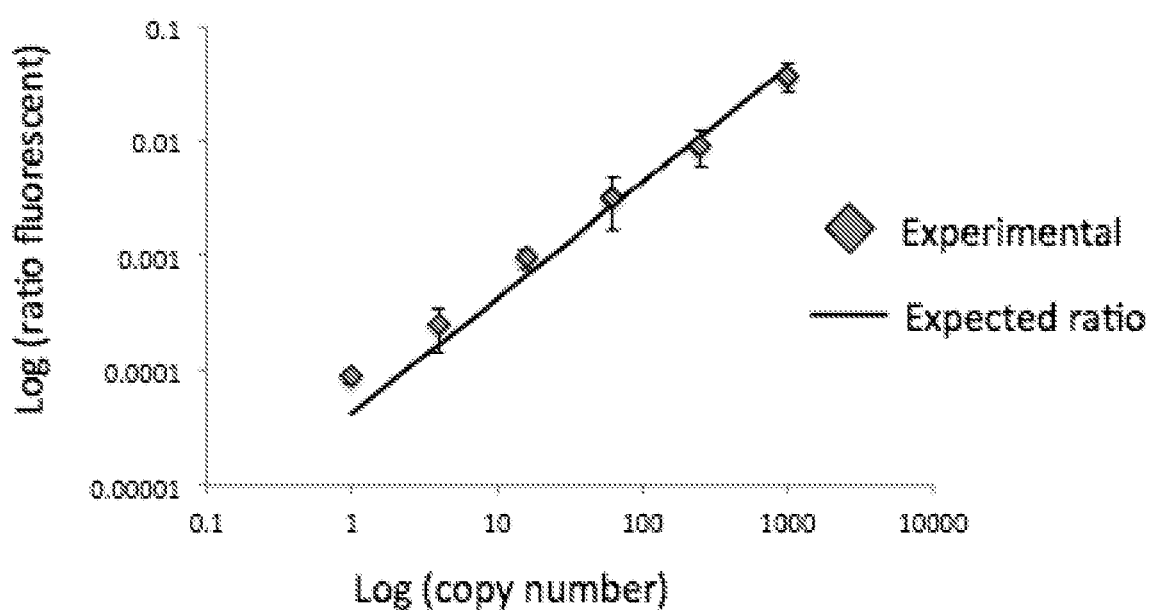
FIG. 13 shows a dose response curve using the double emulsions generator in connection with digital PCR. Lambda DNA was diluted 1:2 from an expected range of 950 copies of DNA per µL to 0.928 copies of DNA per µL, encapsulated, and brought through the dPCR technique described (n=3; error bars=standard deviation).

Using the FACS data, the precise fraction of positive and negative droplets can be measured for samples at different, known target concentrations. When this fraction is plotted as a function of the target concentration, it is roughly linear over 3-4 orders of magnitude and in good agreement with the expected ratio based on a Poisson distribution for droplet loading, as shown in FIG. 13. This shows that by measuring the fraction of positive double emulsion droplets using FACS, the concentration of the target molecule can be accurately estimated.

Figure 16:
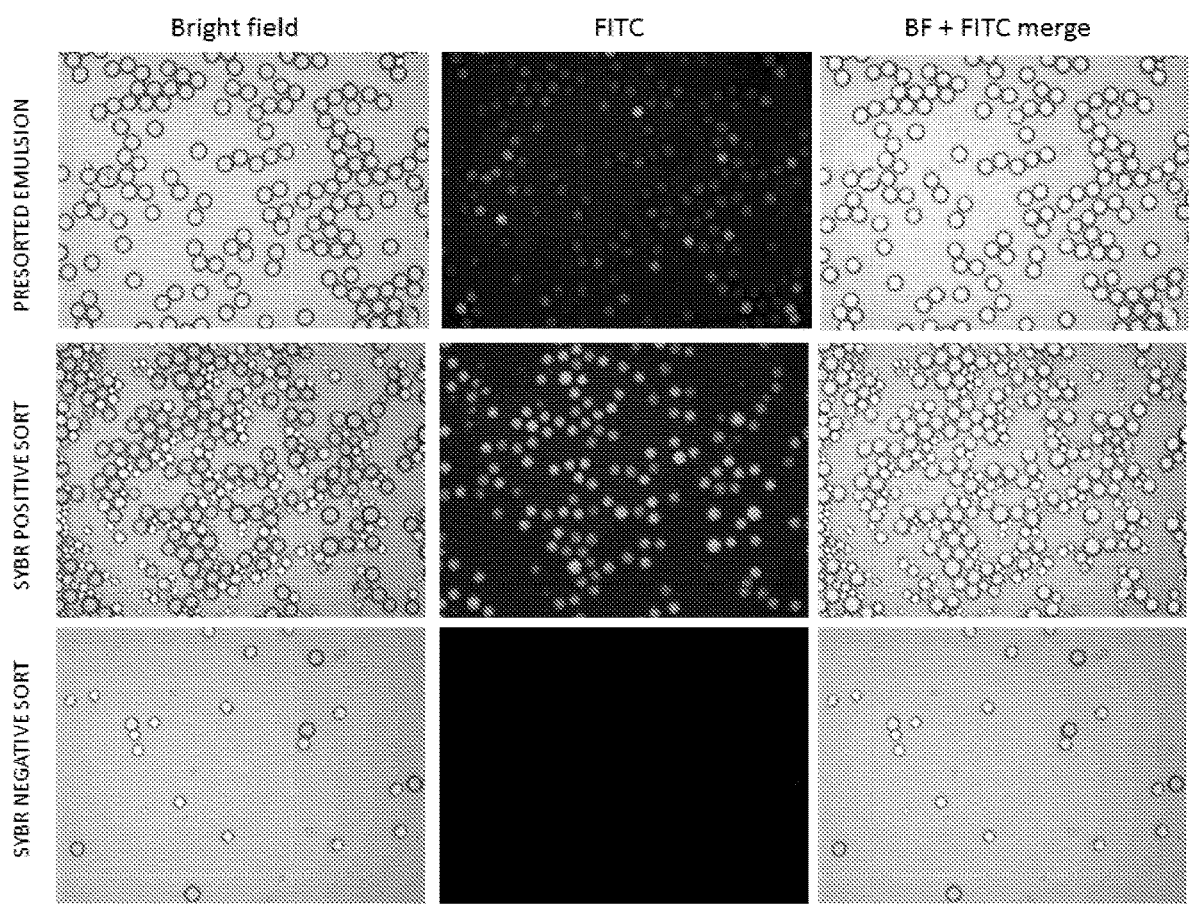
FIG. 16. provides images of double emulsions used to performed digital droplet PCR presorting (upper panel) and post sorting for the positive collection channel (middle panel) and the negative collection channel (lower). Presorting the population consists of a mixture of bright and dim droplets, but post sorting the positive collection contains nearly all bright droplets and the negative collection early all dim droplets.

FACS instruments have the additional capability of sorting fluorescent entities at extremely high speeds—some instruments reporting maximum sorting speeds of 100 kHz. When combined with 3DPCR, this provides an effective method for enriching target molecules out of a heterogeneous sample. This approach allows the sorting of single target molecules to recover all target molecules in a sample and discard off-target molecules. To illustrate this, a sample comprising target molecules at a specific concentration was generated. At this concentration, rare instances of positive double emulsions were observed mixed into a much larger population of dim double emulsions, as shown in FIG. 16, upper. After FACS sorting the double emulsions, however, it was observed that the collection container of positive events had droplets that were nearly all fluorescent, while the container for negative events had droplets that were nearly all dim, FIG. 16. This demonstrated that, using FACS, it is possible to sort 3DPCR droplets based on fluorescence which, when combined with PCR, enables sequence specific sorting of DNA molecules to perform MESA enrichment.

Example 7: Prophetic Example of Using Multiplexed Digital PCR in Double Emulsions to Measure Genome Size Distribution The genome size distribution of a sample can be measured with multiplexed digital PCR reactions in double emulsions. Generally, TaqMan® probes are designed for regions spaced along the genome. The probe on one end of the genome has a first color dye, and all of the other TaqMan® probes have a second dye. Multiplexed digital PCR reactions are performed in double emulsions, e.g., double emulsions prepared as described herein, with every pair of probes. The genome size distribution of the sample can be measured by comparing the number of double positive double emulsion droplets for each pair of TaqMan® probes as a function of distance between the probes.

As a specific example, TaqMan® probes can be designed to evaluate the size distribution of a lambda phage sample. A first TaqMan® probe labeled with a first dye (e.g., Cy5) is designed to hybridize at one end of the genome, and additional TaqMan® probes labeled with a second dye (e.g., FAM) are designed to hybridize at various additional points spanning the genome.

The double emulsions are prepared in a single device. PCR mix, e.g., Platinum Multiplex Master Mix, primers and target DNA are encapsulated first by HFE with a fluorinated surfactant, which is in turn encapsulated by a second aqueous layer including PEG, Tween, Pluronic S-68, KCl, $MgCl_2$. Emulsions are collected in PCR reaction vessels containing KCl and $MgCl_2$. These reaction vessels are then directly cycled for PCR amplification. Digital PCR samples are prepared for every pair of TaqMan® probes. For example, for a lambda phage genome ~48.5 kb in length with the first probe hybridized at 1 kb and the remaining probes hybridized at 4 kb, 18 kb, 35 kb and 46 kb, four separate digital PCR reactions would be prepared:
1. Cy5 probe at 1 kb with the FAM probe at 4 kb
2. Cy5 probe at 1 kb with the FAM probe at 18 kb
3. Cy5 probe at 1 kb with the FAM probe at 35 kb
4. Cy5 probe at 1 kb with the FAM probe at 46 kb The double emulsions are thermocycled according to the cycling parameters specified for the PCR mix and the samples are tested in triplicate. A fluorescence microscope can be used to image the thermocycled double emulsion droplets. Four populations of double emulsion droplets are identifiable: empty droplets with no signal, droplets with signal from one TaqMan® probe, droplets with signal from the other TaqMan® probe, and droplets with signal from both TaqMan® probes. The numbers of droplets that fall into these four populations are quantified using imaging analysis software. As an alternative to using microscopy and imaging analysis, microfluidic detectors or FACS can be used for analyzing the double emulsion droplet fluorescence.

If a double emulsion droplet is positive for both labeled TaqMan® probes, then the genomic sample was intact and contained the genomic regions targeted by both TaqMan® probes. Similarly, if a double emulsion droplet is positive for only one TaqMan® probe, then that encapsulated sample was fragmented and did not contain the genomic region targeted by the other probe.

The fraction of double positive double emulsion droplets is plotted as a function of distance between the probes on the genome. If a sample is perfectly intact, then all of the droplets that are positive will be positive for both TaqMan® probes regardless of how far apart the TaqMan® probes are spaced along the genome. If a sample has some amount of fragmentation or degradation, then the number of double positive double emulsion droplets will decrease as the distance between the TaqMan® probes increases. Samples that are more extensively degraded will have a greater decrease in the number of double positive droplets as a function of increased distance between the probes. Using this method, multiplexed digital PCR can be used to measure the genome size distribution of DNA and RNA samples.

Figure 17:
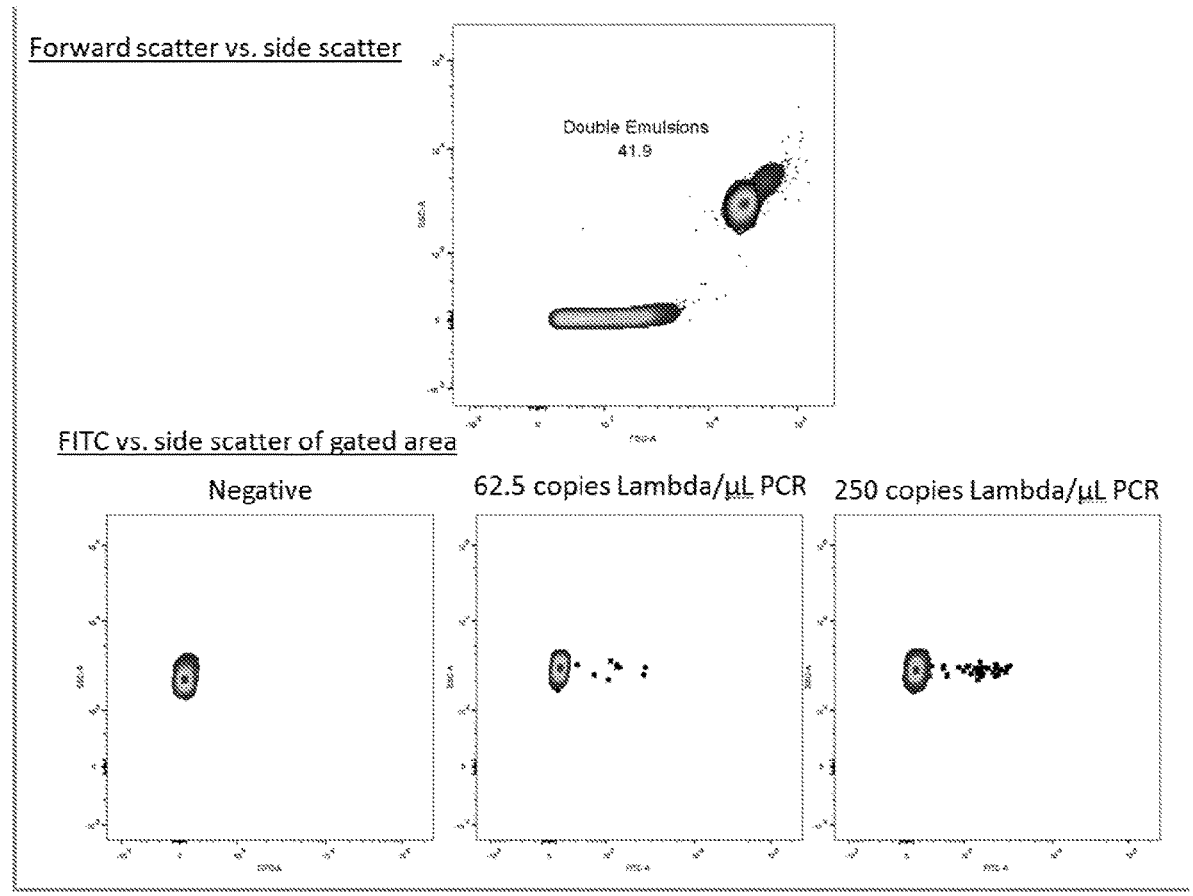
FIG. 17 provides FACS data of double emulsions used to detect and enrich Lambda virus genomes out of a sample.

Example 8: Double-Emulsion MESA for the Enrichment of HIV Provirus from Human Genomic DNA As an illustration of the ability to sort viral genomes with FACS, an experiment was performed in which lambda virus was loaded into a sample at different concentrations, and each sample was sorted using MESA and FACS, FIG. 17. A distinct population of strongly scattering droplets was observed (FIG. 17, upper). When gated on large scattering events and plotted as a function of side scattering versus fluorescence intensity, the negative population devoid of lambda produced no positive events, while the population with 62.5 copies per microliter produced positive events and the sample at 250 copies per microliter produced even more positive events, as shown in FIG. 17, lower panels. This demonstrated that 3DPCR/MESA can be used to detect viral genomes in solution, that the detection is quantitative, and that by using the sorting capabilities of the instrument, it should be possible to recover the viral genomes.

The MESA methodology described herein provides a powerful method for enriching target nucleic acids for sequencing analysis. Compared to other methods like oligo hybridization capture, MESA uses far less information (e.g., <100 bp of known sequence) to specifically recover far larger molecules (megabases) or, if within cells or viruses, even whole genomes. To illustrate this, MESA was used to sequence the proviral HIV repertoire in an infected individual undergoing antiretroviral (ART) therapy. Patients successfully treated with ART often have few symptoms of infection, since the virus is prevented from replicating in high numbers. Correspondingly, the patient's T cells may only be infected at a rate of 1 in 1000 cells. This means that without enrichment or PCR amplification, recovering the genomic sequences of one HIV provirus requires sequencing 1000 human genomes equivalent of DNA—something that is often cost prohibitive. Sequencing a repertoire of just 1000 HIV variants, on the other hand, would require the sequencing of over a million human genomes equivalent DNA, which is impractical. Methods for enriching the provirus out of human genomic DNA are often ineffective because the viral genome is small, embedded in unknown locations within the human genome, and present at extremely low levels. In addition, PCR enrichment tends to selectively amplify short genomes that contain deletions, which are less likely to be of biological relevance since the corresponding viruses are often defective.

MESA provides a way to obtain the HIV provirus repertoire in an infected individual. In this experiment, primer sets specific to four different genes in HIV, regions of gag, pol, env, and the 3'LTR, as illustrated in FIG. 18, were generated. Gag and env probes were used for MESA sorting and the pol and 3'LTR probes were reserved for downstream qPCR confirmation of enrichment. Because HIV is present at such an extremely low level, the number of nucleic acids molecules that need to be sorted is extremely high. For example, at a conservative infection rate of 1 in 2000 human T cells, and fragmenting the genome into 100 kb molecules, ~120 trillion molecules would have to be sorted to recover 1000 HIV genomes. Since current production is at about ~10 million droplets, ~12,000 genomic fragments need to be loaded into each double emulsion, one of which may contain a proviral genome. After sorting for several hours to recover all 1000 expected positive droplets, ~12,000,000 100 kb molecules were recovered, in which it is estimated that HIV is present at about 0.008%. This is ~10,000× enrichment compared to the starting concentration, but still relatively low. To make sequencing practical, a second enrichment is performed. This time, the sorted output from the first MESA is taken and run and diluted such that each of the 10 million droplets contains 1.2 molecules on average. Sorting for several hours, ~1200 100 kb molecules were recovered. Of these recovered molecules, it is expected that 83% will contain a proviral genome, enriching the sample by another 10,000×.

The enrichment power of performing multiple MESA sorts back to back comes at a cost, which is that even if a large amount of material is used at the beginning, very little material is recovered at the end so that it may not be possible to directly sequence the material, which often requires nanogram quantities. To address this issue, the sorted material was amplified using non-specific multiple displacement amplification (MDA), for which 100 kb molecules are a good substrate and lead to accurate amplification. This allows for the production of sufficient material to generate sequencing libraries.

To quantitate the results of the double MESA sort and post-sort MDA, qPCR analysis was utilized. The sample was split into four reactions. Each was diluted by 100-fold, and combined with one of the primer sets for gag, pol, env, or 3'LTR, FIG. 19. A comparison sample was also created which consisted of the original, un-enriched human genomic DNA at a concentration such that the provirus was expected to be present at 10 copies. The 100× dilution ensures that the MESA sorted and comparison samples are at the same DNA concentration, allowing direct relation between the measured Ct values and the number of copies of provirus in the sorted samples. Performing qPCR analysis, it was found that the MESA sorted samples rise between 15-20 thermal cycles, while the standards rise at around 30 thermal cycles. This corresponds to an average Ct shift of ~12.5 cycles, which, when combined with the 100× dilution, corresponds to a $10^5$-$10^7$ fold enrichment over the starting concentration. This demonstrates that MESA, particularly when performed serially on the same sample, can be used to highly enrich for nucleic acids containing the target sequence.

To illustrate the general applicability of the process, it was used to enrich T4 virus out of a sample, FIG. 20. As in standard single emulsion digital PCR (FIG. 20, panel A), digital droplet fluorescence was observed with 3DPCR (FIG. 20, panel B). However, a powerful advantage of the double emulsions used in 3DPCR is that the positive droplets can be recovered by sorting the droplets with FACS, as shown in FIG. 20, panel C. Again, a clear population of large scatterers was observed, which are the double emulsions, FIG. 20, panel D and, when the intensity histogram of the double emulsions was plotted, it was bimodal, having a large population of dim droplets and a smaller population (10.6%) of fluorescent droplets, as shown in FIG. 20, panel E. Combined with the data for Lambda virus and HIV, these results demonstrate the general applicability of MESA for enriching nucleic acids containing viral sequences, as well as any other sequence detectable with a PCR assay.

Example 9: Combined Multiple-Displacement Amplification and PCR in an Emulsion Microdroplet In order to test whether Multiple Displacement Amplification (MDA) would increase the initial quantity of encapsulated DNA sufficiently to allow for the efficient construction of next generation sequencing libraries, a 3-step protocol was tested, which included generally (1) the encapsulation of DNAs of interest in double emulsions containing all reagents necessary for both MDA and TaqMan®, followed by (2) a non-specific amplification of all DNA present in the partitioned sample, and then (3) the use of a TaqMan® PCR reaction to identify the emulsions containing DNAs of interest.

Purified buffered DNA from *S. cerevisiae* was first heated in a thermocycler to 86° C. for 5 minutes in the presence of random hexamers and primers specific to a region of chromosome XIV targeted for enrichment. After cooling to room temperature, denatured DNA was mixed with BSA, dNTPs, Bst2.0, Taq DNA polymerase, and probe DNA specific to the target region prior to encapsulation using a double emulsion microfluidics chip as described herein. Samples were then allowed to go through 5 cycles of MDA incubation (25° C. for 5 minutes, followed by incubation at 42° C. for 25 minutes), followed immediately by temperature conditions specific for the TaqMan® reaction (86° C. for 2 minutes, followed by 35 cycles of 86° C. for 30 sec, 60° C. for 1:30, and 20° C. for 20 seconds).

After the TaqMan® reaction, samples were sorted using a flow cytometer based upon the absolute FITC fluorescence of the emulsions, followed by library construction utilizing Illumina® protocols. Libraries were then sequenced using the MiSeq® system.

FIG. 21 shows results obtained from these experiments. FIG. 21 shows the gated scatter plot where sufficient initial *S. cerevisiae* was loaded to obtain ~1% positive emulsions. As shown, after the MDA and TaqMan® reactions there were about 1% FITC positive emulsions (circle). Approximately 10K positive emulsions, as well as a similar number of unsorted emulsions, were collected and made into libraries that were sequenced using the MiSeq® system. The subsequent sequences were assembled into contigs. While the unsorted sequencing data (Figure. 22, bottom map) showed a lack of large contigs that map to chromosome XIV, the sorted sequencing data (Figure. 22, top map) showed a large sequenced region centered around the probed region of interest.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A nucleic acid amplification method comprising:
   (a) encapsulating a target nucleic acid and amplification reagents in an emulsion microdroplet, wherein the amplification reagents comprise non-specific amplification reagents and PCR amplification reagents;
   (b) non-specifically amplifying the target nucleic acid, thereby producing a non-specific amplification product in the emulsion microdroplet;
   (c) amplifying the non-specific amplification product of (b) by PCR amplification, thereby producing a PCR amplification product in the emulsion microdroplet; and
   (d) detecting the PCR amplification product of (c).

2. The method of claim 1, wherein non-specifically amplifying the nucleic acid comprises amplifying the nucleic acid by Multiple Displacement Amplification (MDA).

3. The method of claim 2, wherein the MDA comprises amplification of the nucleic acid with a polymerase which is active under buffer conditions under which Taq DNA polymerase is active.

4. The method of claim 3, wherein the polymerase is a Bst polymerase.

5. The method of claim 1, wherein the PCR amplification reagents comprise Taq DNA polymerase.

6. The method of claim 1, wherein the emulsion microdroplet is a multiple-emulsion microdroplet comprising a first miscible phase fluid surrounded by an immiscible shell, wherein the multiple-emulsion microdroplet is positioned in a second miscible phase carrier fluid.

7. The method of claim 6, wherein the second miscible phase carrier fluid is a buffered aqueous phase carrier fluid.

8. The method of claim 6, wherein the first and second miscible phase fluids are the same.

9. The method of claim 1, further comprising labeling the PCR amplification product with a detectable label prior to (d).

10. The method of claim 1, wherein the PCR amplification reagents comprise detectably labeled primers and/or probes.

11. The method of claim 9, wherein the detectable label is a fluorescent label, and wherein the method further comprises sorting emulsion microdroplets via fluorescence activating cell sorting (FACS).

12. The method of claim 11, further comprising pooling nucleic acid sequences from the sorted emulsion microdroplets, thereby providing an enriched pool of target nucleic acid sequences.

13. The method of claim 1, wherein (a) comprises encapsulating a single cell comprising the nucleic acid in an emulsion microdroplet, and wherein the method further comprises lysing the single cell prior to (b).

14. The method of claim 1, wherein no more than 10 fg of the target nucleic acid is present the emulsion microdroplet prior to (b).

15. The method of claim 1, further comprising sequencing the PCR amplification product.

16. The method of claim 1, wherein the PCR amplification reagents comprise one or more primers that hybridize to the non-specific amplification product.

17. The method of claim 1, wherein the target nucleic acid comprises a nucleic acid sequence that is not present in the PCR amplification product.

18. The method of claim 6, wherein encapsulating the amplification reagents comprises introducing the non-specific amplification reagents into the second miscible phase carrier fluid, wherein the non-specific amplification reagents diffuse from the second miscible phase carrier fluid through the immiscible shell and into the first miscible phase fluid of the multiple-emulsion microdroplet.

19. The method of claim 1, wherein the emulsion microdroplet comprises monodisperse microdroplets.

20. The method of claim 6, wherein encapsulating the amplification reagents comprises introducing the PCR amplification reagents into the second miscible phase carrier fluid, wherein the PCR amplification reagents diffuse from the second miscible phase carrier fluid through the immiscible shell and into the first miscible phase fluid of the multiple-emulsion microdroplet.

\* \* \* \* \*

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
gttgattcag gtgcggtagt t                                              21

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
gcctgctgtt ccttcatctt                                                20

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
ctttgaatgc tgcccttctt c                                              21

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
cagataacca tctgcggtga ta                                             22
```